US010450570B2

(12) United States Patent
Simons et al.

(10) Patent No.: US 10,450,570 B2
(45) Date of Patent: Oct. 22, 2019

(54) COMPOSITIONS AND METHODS FOR CONTROLLING VASCULATURE

(71) Applicant: YALE UNIVERSITY, New Haven, CT (US)

(72) Inventors: Michael Simons, Hamden, CT (US); Pengchun Yu, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/830,420

(22) Filed: Dec. 4, 2017

(65) Prior Publication Data

US 2018/0163210 A1 Jun. 14, 2018

Related U.S. Application Data

(60) Provisional application No. 62/430,698, filed on Dec. 6, 2016.

(51) Int. Cl.
| | | |
|---|---|---|
| *C12N 15/113* | (2010.01) | |
| *A61P 35/00* | (2006.01) | |
| *A61K 31/7105* | (2006.01) | |
| *C12Q 1/48* | (2006.01) | |
| *A61K 45/06* | (2006.01) | |
| *A61P 9/00* | (2006.01) | |
| *G01N 33/68* | (2006.01) | |

(52) U.S. Cl.
CPC ...... *C12N 15/1137* (2013.01); *A61K 31/7105* (2013.01); *A61K 45/06* (2013.01); *A61P 9/00* (2018.01); *A61P 35/00* (2018.01); *C12Q 1/48* (2013.01); *C12Q 1/485* (2013.01); *G01N 33/6893* (2013.01); *C12N 15/113* (2013.01); *C12N 15/1138* (2013.01); *C12N 2310/14* (2013.01); *G01N 2333/912* (2013.01); *G01N 2800/32* (2013.01); *G01N 2800/52* (2013.01); *G01N 2800/7014* (2013.01)

(58) Field of Classification Search
CPC ..... A61P 9/00; A61K 31/7105; C12N 15/113; C12N 15/115; C12N 2310/14
See application file for complete search history.

(56) References Cited

U.S. PATENT DOCUMENTS

2008/0145313 A1* 6/2008 Watson .................... B82Y 5/00
424/9.2

OTHER PUBLICATIONS

Wolf et al. J. Exp. Med. 208, 313-326 (Year: 2008).*
McCommis et al. J Am Heart Assoc. 2:e000355, pp. 1-13 (Year: 2013).*
Cao, et al.,"Mouse corneal lymphangiogenesis model," Nat Protoc. 6(6) ,Jun. 2011 ,817-826 (abstract only).

Chen, et al.,FGF regulates TGF-β signaling and endothelial-to-mesenchymal transition via control of let-7 miRNA expression, Cell Rep. 2(6) ,Dec. 2012 ,1684-1696.
Dahlman, et al.,In vivo endothelial siRNA delivery using polymeric nanoparticles with low molecular weight, Nat Nanotechnol. 9(8) , Aug. 2014 ,648-655.
Foster, et al.,Comprehensive evaluation of canonical versus Dicer-substrate siRNA in vitro and in vivo., RNA. 18 (3) ,Mar. 2012 , 557-568.
Kim, et al.,Hypoxia-inducible factor 1 and dysregulated c-Myc cooperatively induce vascular endothelial growth factor and metabolic switches hexokinase 2 and pyruvate dehydrogenase kinase 1, Mol Cell Biol. 27(21) ,Nov. 2007 ,7381-7393.
Lanza, et al.,"Targeted antiproliferative drug delivery to vascular smooth muscle cells with a magnetic resonance imaging nanoparticle contrast agent: implications for rational therapy of restenosis," Circulation.106(22) ,Nov. 2002 ,2842-2847 (abstract only).
Srinivasan, et al.,Lineage tracing demonstrates the venous origin of the mammalian lymphatic vasculature, Genes Dev. 21(19) ,Oct. 2007 ,2422-2432.
Wilhelm, et al.,FOXO1 couples metabolic activity and growth state in the vascular endothelium, Nature 529(7585) , Jan. 2016 ,216-220.
Bono, et al.,Inhibition of tumor angiogenesis and growth by a small-molecule multi-FGF receptor blocker with allosteric properties, Cancer Cell. 23(4) ,Apr. 2013 ,477-488.
Chittenden, et al.,nEASE: a method for gene ontology subclassification of high-throughput gene expression data, Bioinformatics. 28(5) ,Mar. 2012 ,726-728.
De Bock, et al.,Role of PFKFB3-driven glycolysis in vessel sprouting, Cell. 154(3) ,Aug. 2013 ,651-663.
Herbert, et al.,Molecular mechanism of SSR128129E, an extracellularly acting, small-molecule, allosteric inhibitor of FGF receptor signaling, Cancer Cell. 23(4) ,Apr. 2013 ,489-501.
Tammela, et al.,Lymphangiogenesis: Molecular mechanisms and future promise, Cell. Feb. 19, 2010;140(4) , Feb. 2010 ,460-476.
Tang, et al.,A mouse model of the cornea pocket assay for angiogenesis study, J Vis Exp. (54) ,Aug. 2011 ,3077.

(Continued)

*Primary Examiner* — Brian Whiteman

(74) *Attorney, Agent, or Firm* — Saul Ewing Arnstein & Lehr LLP; Kathryn Doyle; Justin Crotty

(57) ABSTRACT

The invention relates to compositions and methods for reducing excessive vascular development and treat related disorders. In one aspect, the invention provides methods for treating, reducing or inhibiting vascular development in a subject in need thereof. The methods of the invention comprises administering to the subject an effective amount of a HK2 depleting agent that decreases the level of expression and/or activity of HK2. In some embodiments, the level of expression and/or activity of fibroblast growth factor receptor (FGFR), FGF ligand and/or FGF signaling is/are decreased. The invention also includes methods for diagnosing excessive vascular development and for measuring the efficacy of a treatment for an excessive vascular development in a subject in need thereof. The invention further includes a pharmaceutical composition for treating or reducing angiogenesis or lymphangiogenesis, comprising a HK2 depleting agent and a pharmaceutical acceptable carrier.

15 Claims, 41 Drawing Sheets

Specification includes a Sequence Listing.

(56) References Cited

OTHER PUBLICATIONS

Wilson, et al., Isozymes of mammalian hexokinase: structure, subcellular localization and metabolic function, J Exp Biol. 206(Pt 12), Jun. 2003, 2049-2057.

Young, et al., Gene ontology analysis for RNA-seq: accounting for selection bias, Genome Biol. 11(2), 2010, R14.

Zheng, et al., Lymphangiogenic factors, mechanisms, and applications, J Clin Invest. 124(3), Mar. 2014, 878-887.

\* cited by examiner

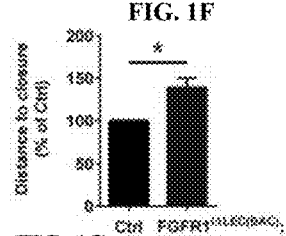
FIG. 1F
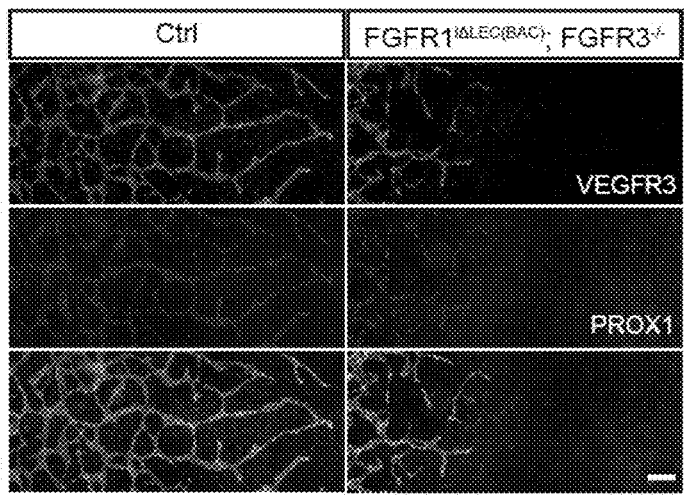
FIG. 1H
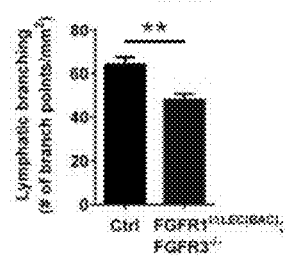
FIG. 1G
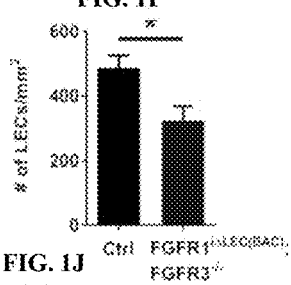
FIG. 1I
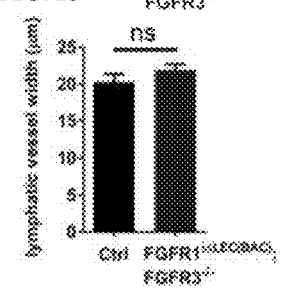
FIG. 1J
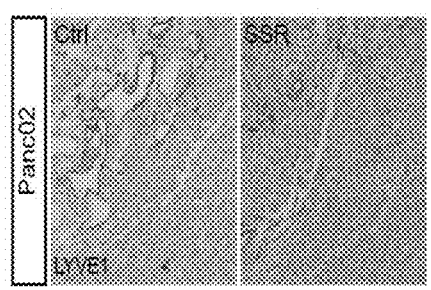
FIG. 1K
FIG. 1L

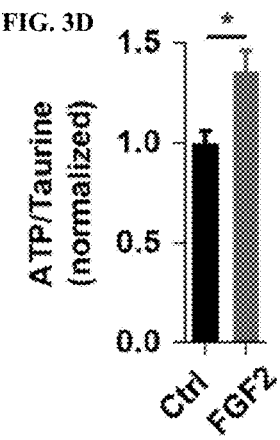
FIG. 3D
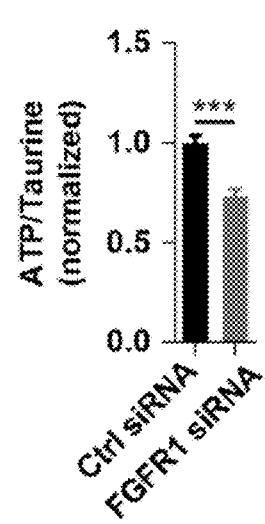
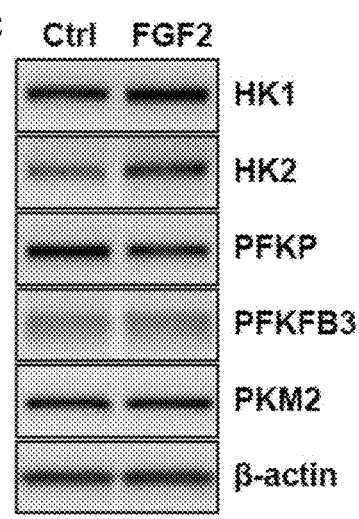
FIG. 3E
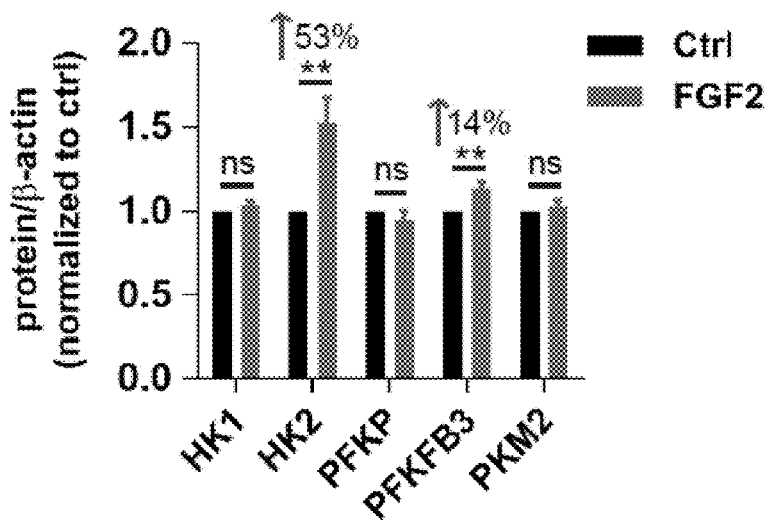
FIG. 3F

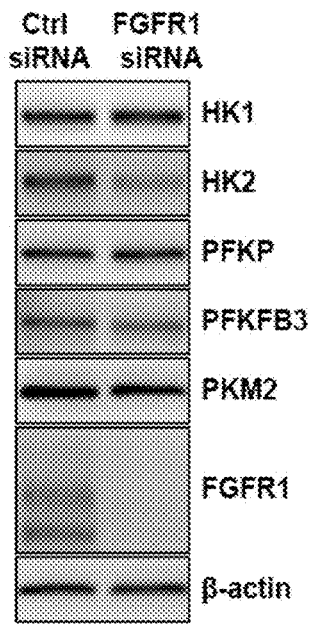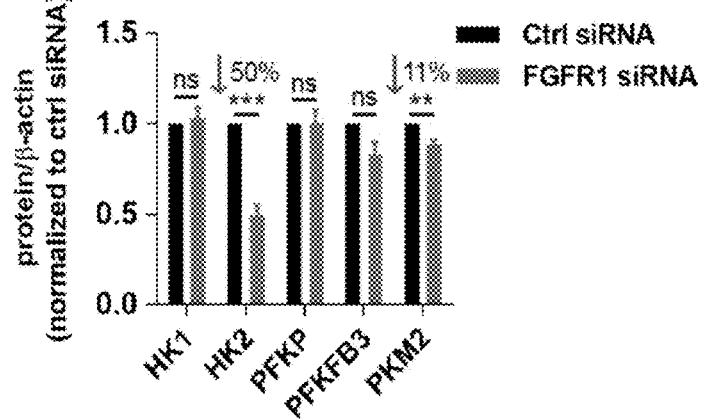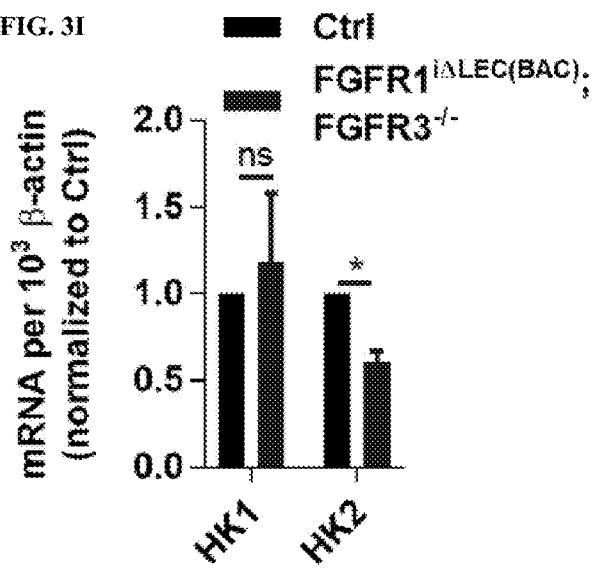

FIG. 4A
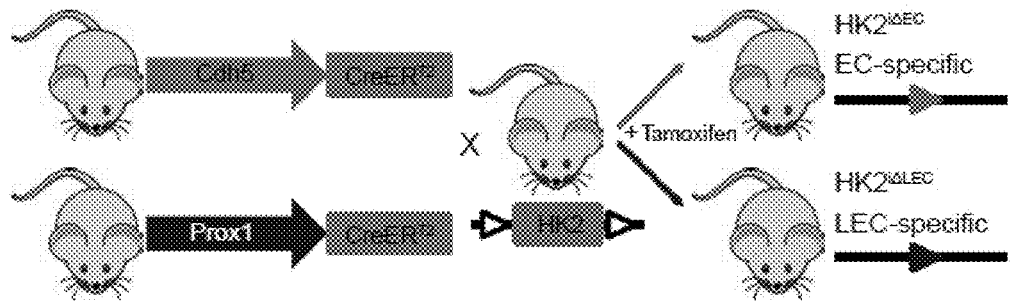
FIG. 4B
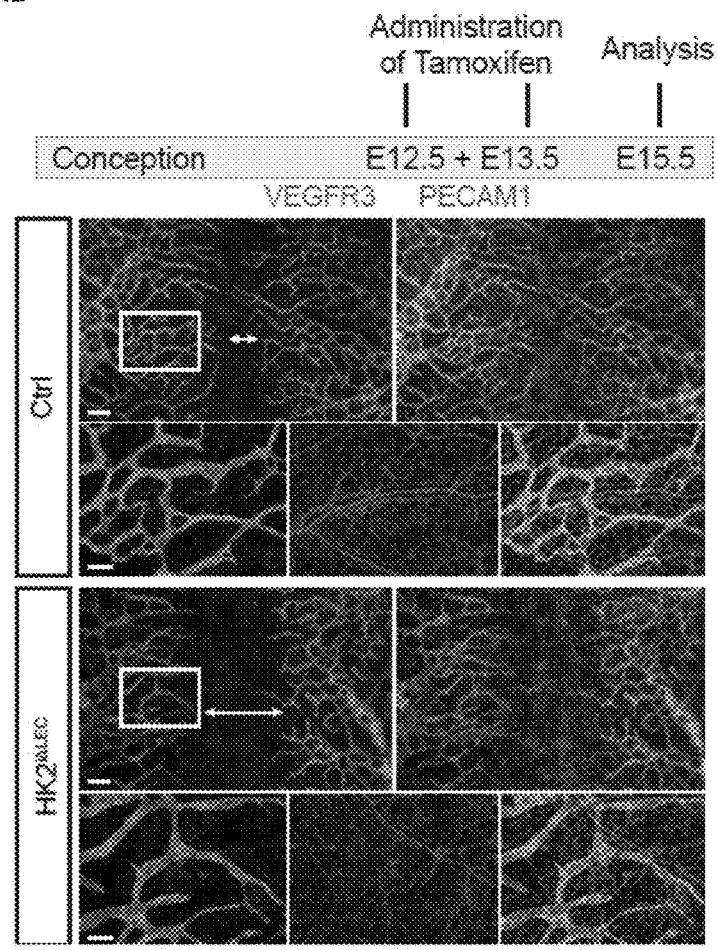
FIG. 4C

ChIP-qPCR to assess
Myc binding to the E-boxes of *hk2*

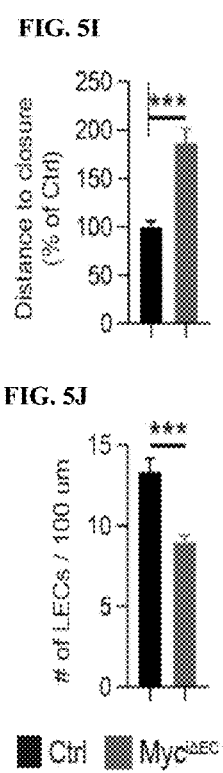
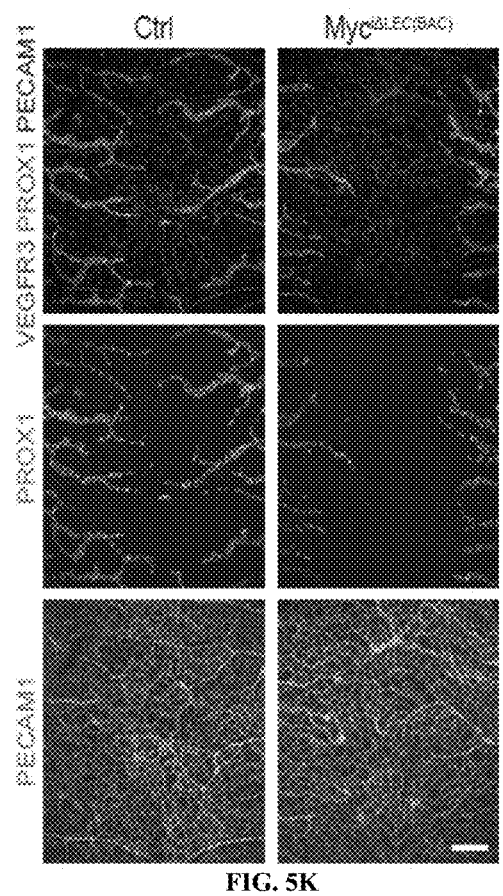
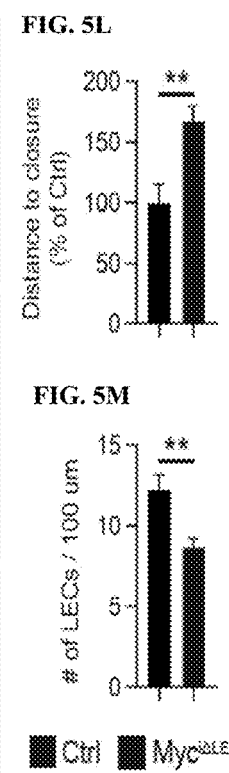
FIG. 5I
FIG. 5J
FIG. 5K
FIG. 5L
FIG. 5M

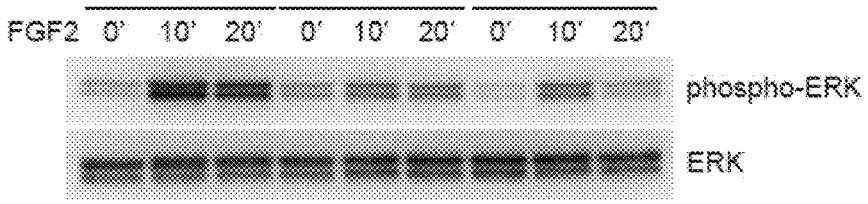
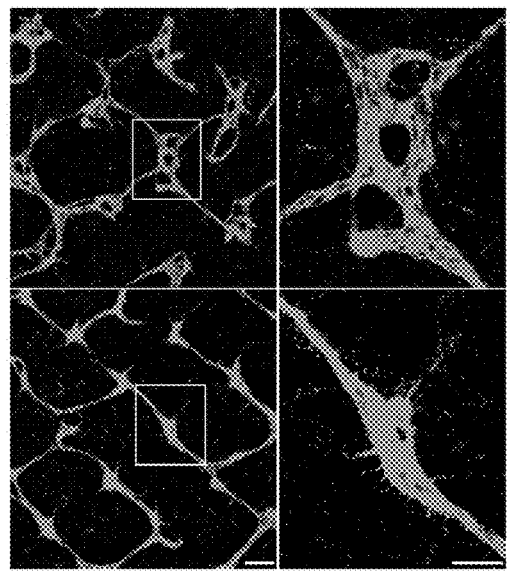
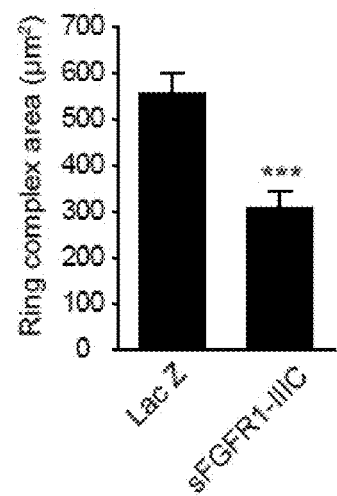

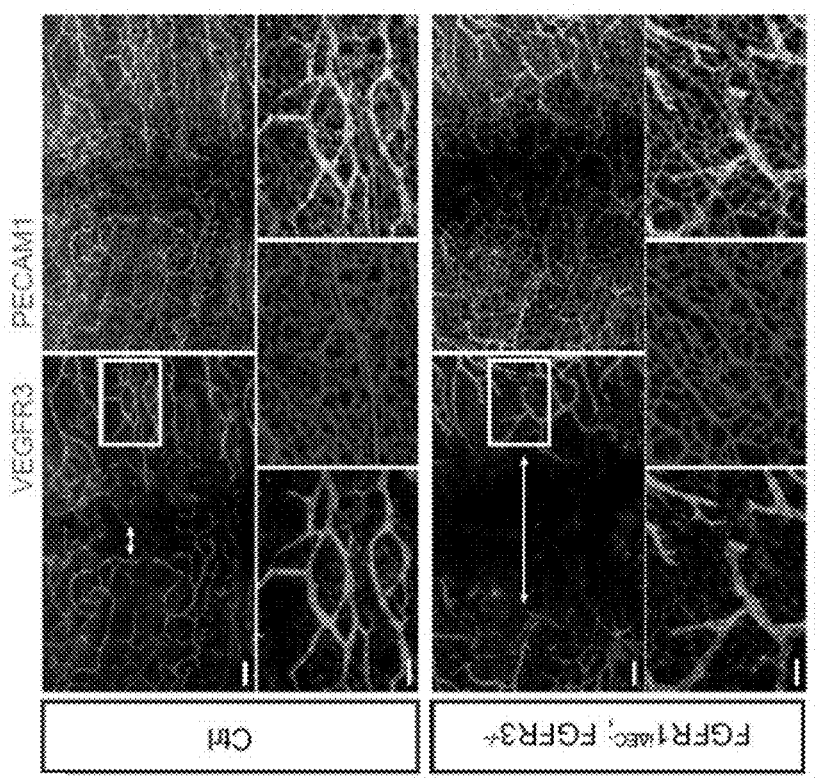
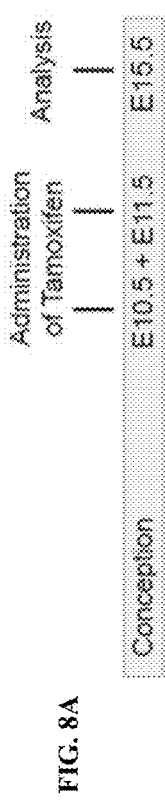
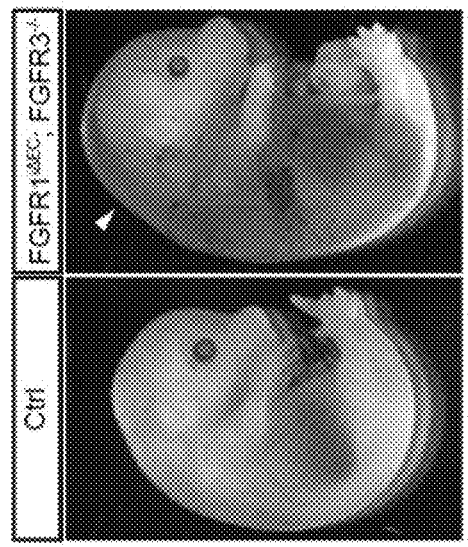
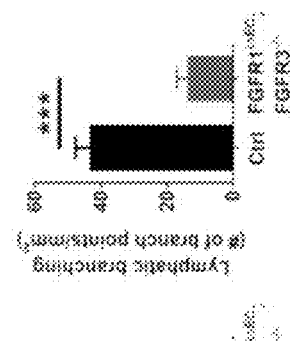
FIG. 8A
FIG. 8B
FIG. 8C
FIG. 8D
FIG. 8E

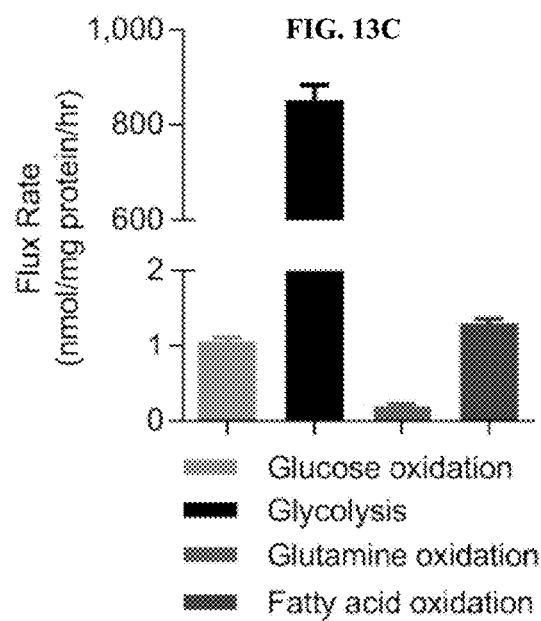
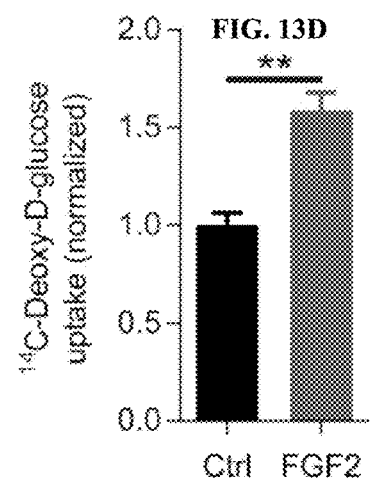
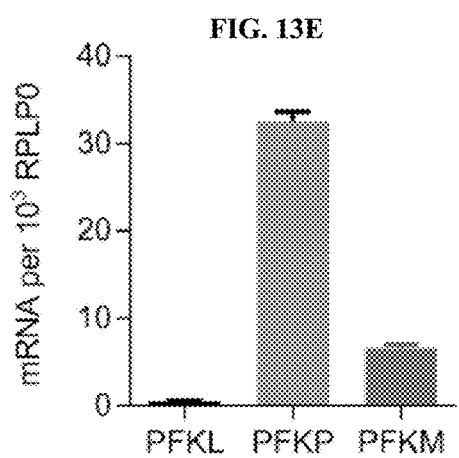
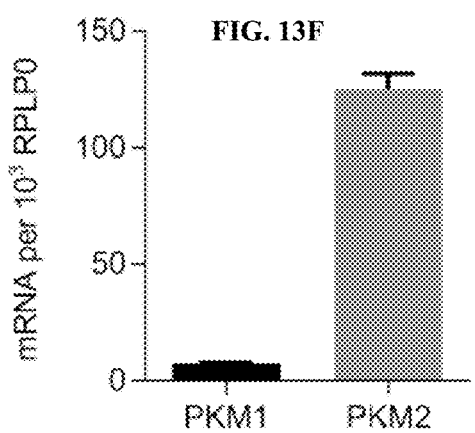

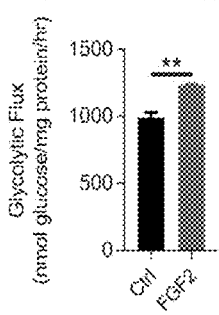
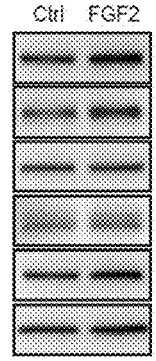
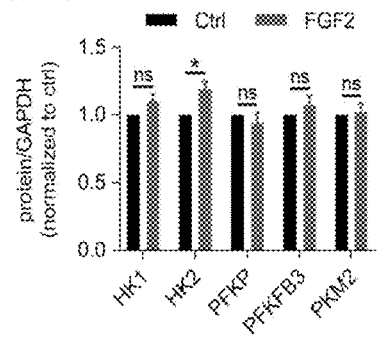
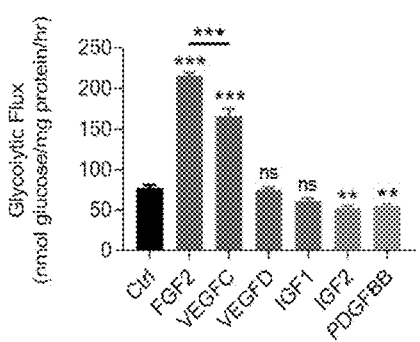
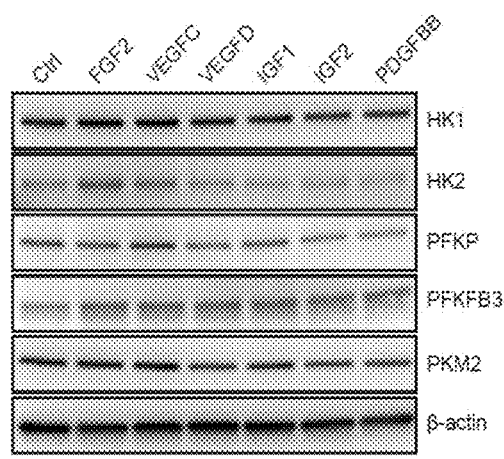
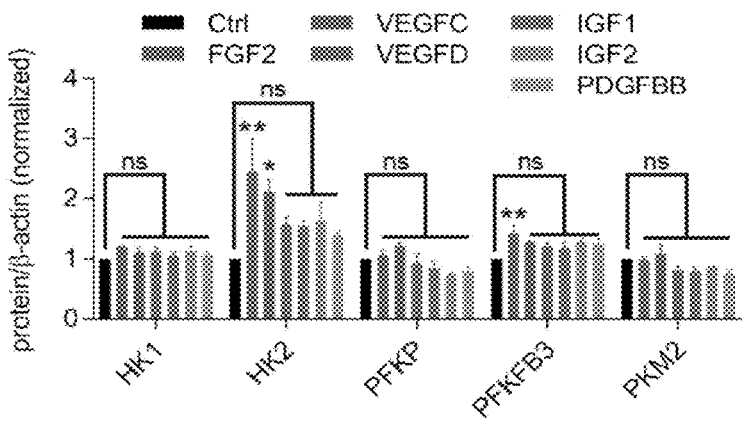

FIG. 18D
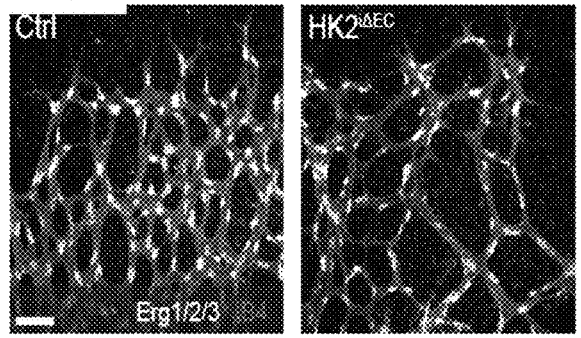
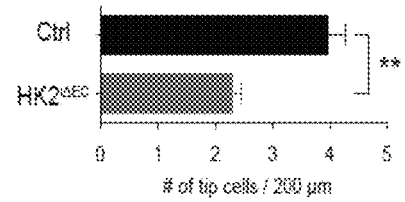
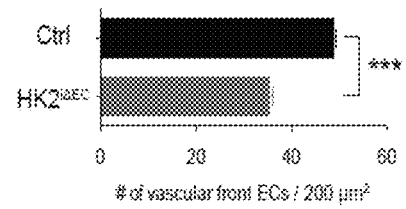
FIG. 18F
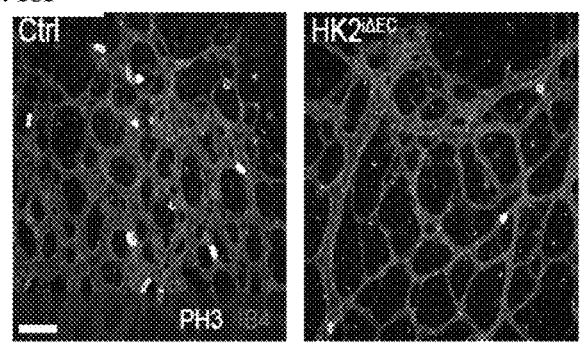
FIG. 18G
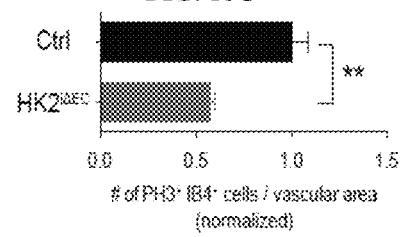
FIG. 18H
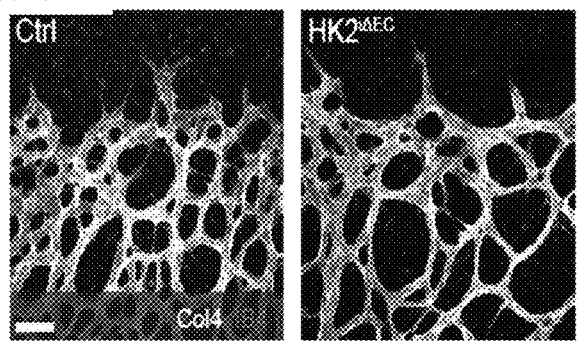
FIG. 18I
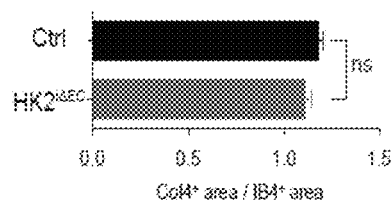

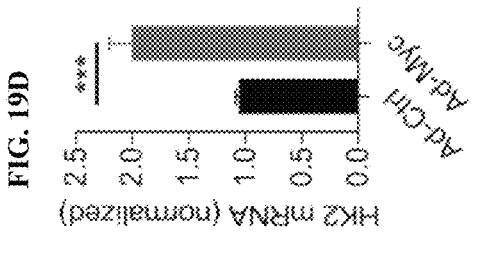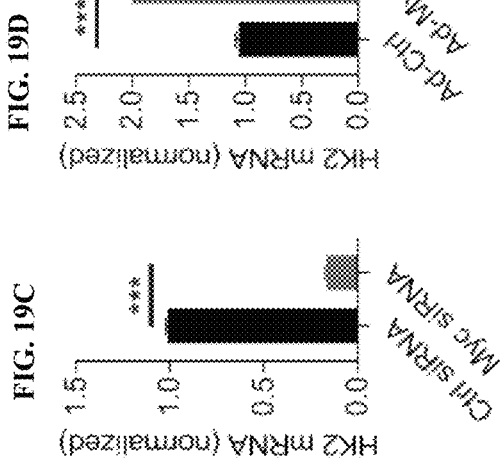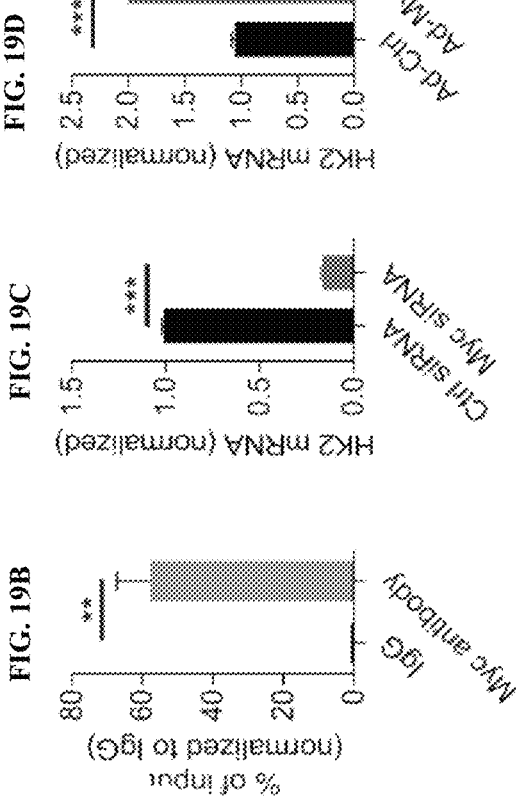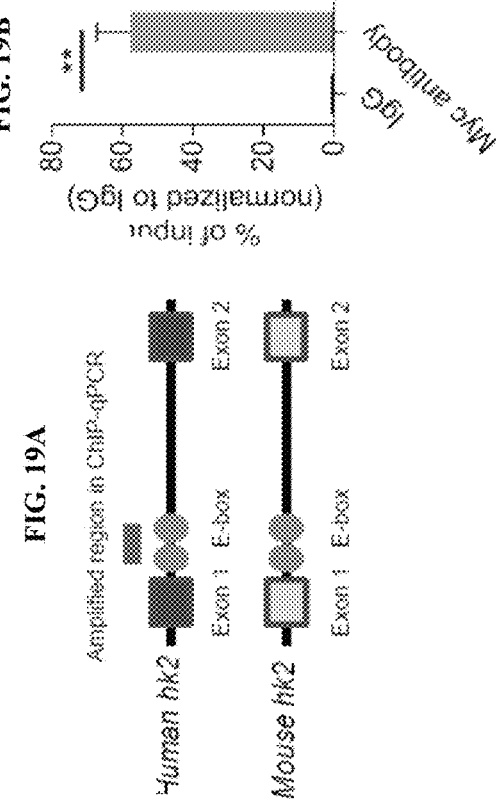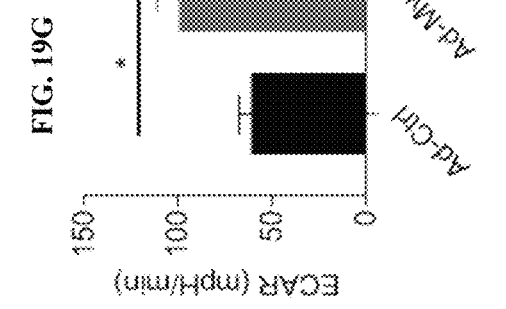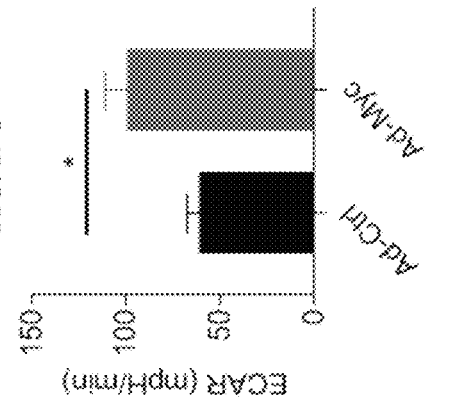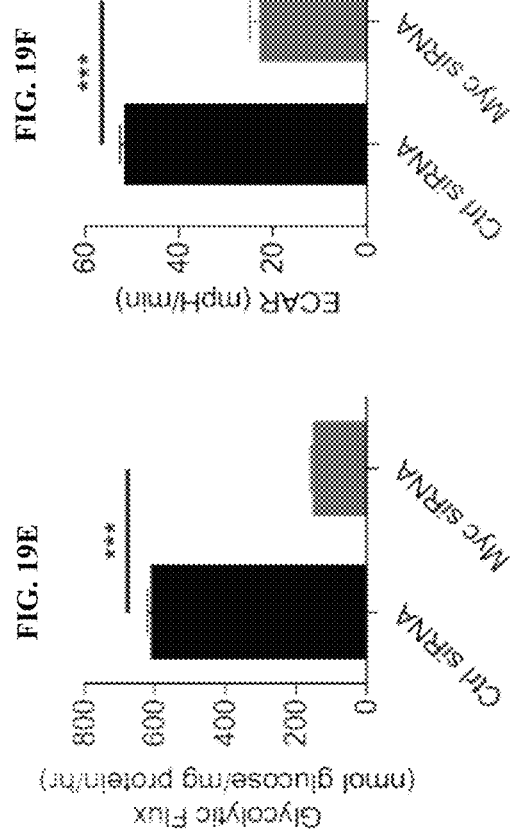

COMPOSITIONS AND METHODS FOR CONTROLLING VASCULATURE

CROSS REFERENCE TO RELATED APPLICATIONS

The present application claims priority under 35 U.S. C. § 119(e) to U.S. Provisional Patent Application No. 62/430,698, filed on Dec. 6, 2016, which is incorporated herein by reference in its entirety.

STATEMENT REGARDING FEDERALLY SPONSORED RESEARCH OR DEVELOPMENT

This invention was made with government support under grant No. HL053793 awarded by National Institutes of Health. The government has certain rights in the invention.

BACKGROUND OF THE INVENTION

The process of vascular development is a highly stereotyped process that involves endothelial cell (EC) migration, proliferation, network assembly, and remodeling among other steps. To date, a significant number of molecules, mostly secreted factors produced by surrounding cells, have been shown to regulate vascular development. Vascular endothelial growth factor A (VEGFA) is critical to the development of the blood vasculature while VEGFC plays an equally important role in lymphatic vasculature development. The latter process involves a cell fate change resulting in the appearance of lymphatic endothelial cells (LECs) followed by proliferation, migration and sprouting of newly formed lymphatic vessels.

Although VEGFs importance is well established, contributions of other growth factors, and in particular that of the fibroblast growth factor (FGF) family, have not been defined. FGFs are known to play important role in stabilization and maintenance of the blood vasculature, but the role of these growth factors in vascular development remains unclear. Twenty-two members of the FGF family exert their biological effects via four distinct receptor tyrosine kinases (FGFR1-R4), each of which can exist in two different isoforms that determine its signal specificity. In addition, a number of auxiliary receptors, including syndecans and Klothos, regulate FGF signal transduction. This complexity of FGF biology presents distinct challenges to experimental studies of their biological roles.

Endothelial migration and sprouting, processes prominent in vascular development, are regulated by a number of different cytokines and growth factors that can activate contraction and proliferation machineries.

It is well established in the art that angiogenesis is implicated in the pathogenesis of a variety of disorders. In the case of tumor growth, angiogenesis appears to be crucial for the transition from hyperplasia to neoplasia, and for providing nourishment for the growth and metastasis of the tumor. The neovascularization allows the tumor cells to acquire a growth advantage and proliferative autonomy compared to the normal cells. This process involves a multitude of angiogenesis stimulators and inhibitors. In view of the role of angiogenesis in many diseases and disorders, various anti-angiogenic drugs and in particular anti-vascular endothelial growth factor (VEGF) agents have been developed such as Bevacizumab. However these drugs can be toxic and have many side effects such as, for example, bleeding.

There is an urgent need in the art for new methods of modulating vascular development, and particularly methods of inhibiting development or progression of angiogenesis. This invention addresses this need.

SUMMARY OF THE INVENTION

In one aspect, the invention provides a method for treating excessive vascular development in a subject in need thereof, the method comprising administering to the subject an effective amount of a hexokinase 2 (HK2) depleting agent that decreases the level of expression and/or activity of HK2 thereby decreasing the level of expression and/or activity of at least one selected from the group consisting of a fibroblast growth factor receptor (FGFR), a FGF ligand and FGF signaling, thereby treating the excessive vascular development in the subject, wherein the HK2 depleting agent targets an endothelial cell in the subject.

In various embodiments, endothelial migration, sprouting and proliferation are reduced in the subject.

In various embodiments, the level or activity of the FGFR is decreased and the FGFR comprises FGFR1 and/or FGFR3.

In various embodiments, the vascular development comprises angiogenesis or lymphangiogenesis.

In various embodiments, the vascular development is a pathological angiogenesis or lymphangiogenesis associated with ischaemic and inflammatory diseases.

In various embodiments, the vascular development is associated with a cardiovascular disease.

In various embodiments, the vascular development is associated with cancer.

In various embodiments, the HK2 depleting agent is selected from the group consisting of an HK2 antibody, an inhibitor of HK2 enzymatic activity, an antisense RNA, a miRNA, a siRNA, a shRNA, a CRISPR system, a ribozyme, an antisense molecule, an aptamer, a peptidomimetic, a small molecule, a nanoparticle and any combination thereof.

In various embodiments, the HK2 depleting agent is administered locally.

In various embodiments, the method further comprises administering to the subject an additional agent selected from the group consisting of a chemotherapeutic agent, an anti-cell proliferation agent, an immunotherapeutic agent and any combination thereof.

In various embodiments, the HK2 depleting agent and the additional agent are co-administered to the subject.

In various embodiments, the route of administration is selected from the group consisting of inhalation, oral, rectal, vaginal, parenteral, topical, transdermal, pulmonary, intranasal, buccal, ophthalmic, intrathecal, and any combination thereof.

In another aspect, the invention provides a method for reducing or inhibiting vascular development in a subject in need thereof, the method comprising administering to the subject an effective amount of a hexokinase 2 (HK2) depleting agent in a pharmaceutical acceptable carrier, wherein the HK2 depleting agent targets an endothelial cell in the subject.

In various embodiments, the HK2 depleting agent decreases the level of expression and/or activity of HK2.

In various embodiments, the HK2 depleting agent decreases the level of expression and/or activity of at least one selected from the group consisting of a fibroblast growth factor receptor (FGFR), a FGF ligand and FGF signaling, thereby treating or reducing vascular development.

In various embodiments, endothelial migration, sprouting and proliferation are reduced in the subject.

In various embodiments, the level or activity of the FGFR is decreased and the FGFR comprises FGFR1 and/or FGFR3.

In various embodiments, the vascular development comprises angiogenesis or lymphangiogenesis.

In various embodiments, the vascular development is a pathological angiogenesis or lymphangiogenesis associated with ischaemic and inflammatory diseases.

In various embodiments, the vascular development is associated with a cardiovascular disease.

In various embodiments, the vascular development is associated with cancer.

In various embodiments, the HK2 depleting agent is selected from the group consisting of a HK2 antibody, an inhibitor of HK2 enzymatic activity, an antisense RNA, a miRNA, a siRNA, a shRNA, a CRISPR system, a ribozyme, an antisense molecule, an aptamer, a peptidomimetic, a small molecule, a nanoparticle and any combination thereof.

In various embodiments, the HK2 depleting agent is administered locally.

In various embodiments, the method further comprises administering to the subject an additional agent selected from the group consisting of a chemotherapeutic agent, an anti-cell proliferation agent, an immunotherapeutic agent and any combination thereof.

In various embodiments, the agent and the additional agent are co-administered to the subject.

In various embodiments, the route of administration is selected from the group consisting of inhalation, oral, rectal, vaginal, parenteral, topical, transdermal, pulmonary, intranasal, buccal, ophthalmic, intrathecal, and any combination thereof.

In another aspect, the invention provides a method for diagnosing excessive vascular development or a predisposition for developing excessive vascular development in a subject in need thereof, the method comprising measuring in an endothelial cell in the subject the level or activity of a marker comprising a HK2 polypeptide or polynucleotide and comparing it to a control, wherein an increase in the level or activity of the marker is indicative of an excessive vascular development or a predisposition for developing excessive vascular development in the subject, and recommending a treatment to the subject.

In various embodiments, the marker further comprises an FGF signaling polypeptide or polynucleotide.

In another aspect, the invention provides a method for measuring the efficacy of a treatment for excessive vascular development in subject in need thereof, the method comprising measuring in an endothelial cell in the subject the level or activity of a marker comprising a HK2 polypeptide or polynucleotide and comparing it to a control, wherein a decrease in the level or activity of the marker is indicative of an effective treatment and recommending a modified or an additional treatment to the subject.

In various embodiments, the marker further comprises an FGF signaling polypeptide or polynucleotide.

In another aspect, the invention provides a pharmaceutical composition for treating angiogenesis or lymphangiogenesis in a subject in need thereof, the pharmaceutical composition comprising a HK2 depleting agent and a pharmaceutical acceptable carrier.

In various embodiments, the HK2 depleting agent suppresses or decreases the expression human HK2 polynucleotide or the activity of human HK2 polypeptide.

In various embodiments, the HK2 depleting agent is a HK2 siRNA.

In various embodiments, the HK2 depleting agent is formulated for selective delivery to an endothelial cell.

BRIEF DESCRIPTION OF THE DRAWINGS

FIGS. 1A-1L are a series of images and graphs demonstrating that lymphatic-specific deletion of both FGFR1 and FGFR3 impairs lymphatic development and FGFR inhibition suppresses pathological lymphangiogenesis. FIG. 1A depicts anterior dorsal skin dissected from E15.5 mouse embryos to analyze the lymphatic vessel development. FIG. 1B depicts E13.5 to E15.5, where lymphatic vessels progressively penetrate into the anterior dorsal skin from both sides and migrate towards the midline (dotted lines). During this process, the distance between the two leading fronts of the lymphatic vessels is gradually decreasing. The embryo head is downward-facing. FIG. 1C depicts FGFR1$^{flox/flox}$; FGFR3$^{-/-}$ mice bred with Cdh5-CreER$^{T2}$ and Prox1-CreER$^{T2(BAC)}$ driver lines to generate EC- and LEC-specific knockouts respectively. FIG. 1D depicts a schematic of the experimental strategy to analyze the dermal lymphatic development of FGFR1$^{i\Delta LEC(BAC)}$; FGFR3$^{-/-}$ embryos. FIG. 1E depicts representative images of anterior dorsal skin with VEGFR3 and PECAM1 staining from E15.5 FGFR1$^{i\Delta LEC(BAC)}$; FGFR3$^{-/-}$ and control (FGFR1$^{flox/flox}$; FGFR3$^{+/-}$) embryos. Double-headed arrows indicate the distance between the two leading fronts of the lymphatic vessels, which is larger in FGFR1$^{i\Delta LEC(BAC)}$; FGFR3$^{-/-}$ skin than in control. Boxed area in low magnification images (scale bar, 250 μm) is presented with high magnification (scale bar, 100 μm). FIGS. 1F-1G depicts quantification of the distance between the two leading fronts of the lymphatic vessels (FIG. 1F; n=3 litters) and the number of lymphatic branch points per mm$^2$ skin area (FIG. 1G; n=4 embryos for control and n =10 embryos for FGFR1$^{i\Delta LEC(BAC)}$; FGFR3$^{-/-}$). FIG. 1H depicts representative images for VEGFR3 and PROX1 staining in the skin of E15.5 FGFR1$^{i\Delta LEC(BAC)}$; FGFR3$^{-/-}$ and control (FGFR1$^{flox/flox}$; FGFR3$^{+/-}$) embryos. Scale bar, 150 μm. FIGS. 1I-1J depicts quantification of the number of LECs (based on PROX1 staining) per mm$^2$ skin area (FIG. 1I; n=4 embryos for control and n=10 embryos for FGFR1$^{i\Delta LEC(BAC)}$; FGFR3$^{-/-}$) and lymphatic vessel diameter (FIG. 1J; n=4 embryos for control and n=10 embryos for FGFR1$^{i\Delta LEC(BAC)}$; FGFR3$^{-/-}$). FIG. 1K depicts representative images of the peritumoral area of orthotopic Panc02 tumors stained for LYVE1 following vehicle (control) or FGFR-inhibitor treatment (SSR). FIG. 1L depicts quantification of the area of LYVE1$^+$ lymphatics per peritumoral area (n=3 mice each condition). *p<0.05; **p<0.01; ns=non-significant.

FIG. 2A is a schematic of the experimental strategy to assess early formation of the retinal vasculature (P0-P5). The triangles indicate the intragastric injections of tamoxifen at P0/1/2. FIG. 2B depicts representative images of IB4-stained retinal vessels (negative images of the fluorescent signal) in P5 FGFR1$^{i\Delta EC}$; FGFR3$^{-/-}$ and control (FGFR1$^{flox/flox}$; FGFR3$^{-/-}$) mice. Scale bar, 500 μm. FIG. 2C depicts quantification of vascular progression (d is the distance between the vascular front and the optic nerve; D is the retina radius), vascular density (AU, arbitrary unit) and the number of branch points per mm$^2$ retina area. n=16 retinas for control and n=19 retinas for FGFR1$^{i\Delta EC}$; FGFR3$^{-/-}$. FIG. 2D depicts angiogenic fronts of IB4- and Erg1/2/3-stained retinal vessels in P5 FGFR1$^{i\Delta EC}$; FGFR3$^{-/-}$ and control (FGFR1$^{flox/flox}$; FGFR3$^{-/-}$) mice. Scale bar, 200 μm. FIG. 2E depicts quantification of the number of tip cells per 200-μm length of the angiogenic front (n=6 retinas for control and n=4 retinas for FGFR1$^{i\Delta EC}$; FGFR3$^{-/-}$) and the number of vascular front ECs per 200-μm$^2$ retina area (n=4 retinas for control and n=4 retinas for FGFR1$^{i\Delta EC}$; FGFR3$^{-/-}$). FIG. 2F depicts retinal vessels stained for Phospho-Histone H3 (PH3) and IB4 in P5 FGFR1$^{i\Delta EC}$; FGFR3$^{-/-}$ and control (FGFR1$^{flox/flox}$; FGFR3$^{-/-}$) mice. Scale bar, 200 μm. FIG. 2G depicts quantification of the number of PH3$^+$ IB4$^+$ endothelial cells per vascular area (normalized to control mice; n=4 retinas for control and n=6 retinas for FGFR1$^{i\Delta EC}$; FGFR3$^{-/-}$). FIG. 2H depicts staining for Collagen IV (Col4) and IB4 in the retinas of P5 FGFR1$^{i\Delta EC}$; FGFR3$^{-/-}$ and control (FGFR1$^{flox/flox}$; FGFR3$^{-/-}$) mice. Scale bar, 200 μm. FIG. 2I depicts quantification of Col4$^+$ area per IB4$^+$ area (n=6 retinas for control and n=6 retinas for FGFR1$^{i\Delta EC}$; FGFR3$^{-/-}$). $p<0.01$; *$p<0.001$; ns=non-significant.

FIGS. 3A-3I are a series of images and graphs showing that FGF signaling controls glycolysis and HK2 expression. FIG. 3A depicts measurement of glycolytic flux in HDLECs under different treatments as indicated (n=4 wells of samples for each condition). FIG. 3B is a schematic of the metabolic pathway of glycolysis which converts glucose to pyruvate. FIG. 3C depicts mass spectrometry measurement of the amount of glycolytic intermediates and lactate under different treatments as indicated (n=6 wells of samples for each condition). FIG. 3D depicts mass spectrometry measurement of ATP generation under different treatments as indicated (n=6 wells of samples for each condition). FIGS. 3E-3F depicts representative western blot analysis (FIG. 3E) and densitometric quantification (FIG. 3F) of glycolytic enzyme expression in control or FGF2-treated HDLECs (n=6 experiments). FIGS. 3G-3H depict representative immunoblot analysis (FIG. 3G) and densitometric quantification (FIG. 3H) of glycolytic enzyme expression in HDLECs treated with control siRNA or FGFR1 siRNAs (n=3 experiments). FIG. 3I depicts qPCR analysis of HK1 and HK2 expression in dermal LECs isolated from E15.5 FGFR1$^{i\Delta LEC(BAC)}$; FGFR3$^{-/-}$ and control embryos with tamoxifen treatment at E12.5 and E13.5 (n=2 litters including 4 control embryos and 2 FGFR1$^{i\Delta LEC(BAC)}$; FGFR3$^{-/-}$ embryos). *$p<0.05$; $p<0.01$; *$p<0.001$; ns=non-significant.

FIGS. 4A-4I are a series of images and graphs depicting that HK2 is essential for lymphangiogenesis. FIG. 4A, HK2$^{flox/flox}$ mice were bred with Cdh5-CreER$^{T2}$ and Prox1-CreER$^{T2(BAC)}$ driver lines to generate EC- and LEC-specific knockouts respectively. FIG. 4B depicts schematic of the experimental strategy to analyze the dermal lymphatic development of HK2$^{i\Delta LEC(BAC)}$ embryos. FIG. 4C depicts representative images of anterior dorsal skin with VEGFR3 and PECAM1 staining from E15.5 HK2$^{i\Delta LEC(BAC)}$ and control embryos. Double-headed arrows indicate the distance between the two leading fronts of the lymphatic vessels, which is larger in HK2$^{i\Delta LEC(BAC)}$ skin than in control. Boxed area in low magnification images (scale bar, 250 μm) is presented with high magnification (scale bar, 100 μm). FIGS. 4D and 4E depict quantification of the distance between the two leading fronts of the lymphatic vessels (FIG. 4D; n=4 litters) and the number of lymphatic branch points per mm$^2$ skin area (FIG. 4E; n=12 embryos for control and n=7 embryos for HK2$^{i\Delta LEC(BAC)}$) in E15.5 HK2$^{i\Delta LEC(BAC)}$ and control (HK2$^{flox/flox}$ or HK2$^{flox/+}$) embryos. FIG. 4F is a schematic of the experimental procedure to analyze cornea lymphangiogenesis. Pellets containing FGF2 or its vehicle were inserted into the mouse cornea. One week after surgery, corneas were dissected, immunostained and flat mounted for analysis. FIG. 4G depicts confocal images of FGF2-implanted cornea of Prox1-CreER$^{T2(KI)}$; mTmG reporter mice. GFP was expressed in nearly all of the cornea lymphatics revealed by LYVE1 staining. Scale bar, 100 μm. FIG. 4H depicts representative images of HK2$^{i\Delta LEC(KI)}$ and control mouse corneas implanted with FGF2 or buffer containing pellets and stained for LYVE1 and PECAM1. Boxed area in low magnification images (scale bar, 1000 μm) is presented with high magnification (scale bar, 200 μm). FIG. 4I depicts quantification of LYVE1$^+$ lymphatic area per cornea in control (HK2$^{flox/flox}$ and HK2$^{flox/+}$) and HK2$^{i\Delta LEC(KI)}$ mice (n=21 corneas for control+buffer, n=5 corneas for HK2$^{i\Delta LEC(KI)}$+buffer, n=11 corneas for control+FGF2, and n=14 corneas for HK2$^{i\Delta LEC(KI)}$+FGF2). *$p<0.05$; $p<0.01$; *$p<0.001$; ns=non-significant.

FIGS. 5A-5M are a series of images and graphs demonstrating Myc mediates FGF regulation of HK2 expression and is critical for lymphatic development. FIG. 5A depicts representative western blot analysis and densitometric quantification of Myc expression in control or FGF2-treated HDLECs (n=4 biological replicates analyzed by 2 western blot experiments). FIG. 5B depicts representative immunoblot analysis and densitometric quantification of Myc expression in HDLECs treated with control siRNA or FGFR1 siRNA (n=4 biological replicates analyzed by 2 western blot experiments). FIG. 5C depicts chromatin immunoprecipitation coupled with quantitative PCR (ChIP-qPCR) to examine the amount of Myc binding to the regulatory region of HK2 gene in HDLECs under different treatments as indicated (n=3 experiments). FIG. 5D depicts representative western blot analysis and densitometric quantification of Myc and glycolytic enzyme expression in siRNA-transfected HDLECs with or without FGF2 treatment (n=3 experiments). FIG. 5E depicts representative immunoblot analysis and densitometric quantification of Myc and glycolytic enzyme expression in siRNA-transfected HDLECs treated with control or Myc adenovirus (n=2-3 experiments). FIG. 5F depicts Myc$^{flox/flox}$ mice were bred with Cdh5-CreER$^{T2}$ and Prox1-CreER$^{T2(BAC)}$ driver lines to generate EC- and LEC-specific knockouts respectively. FIG. 5G depicts bright-field images of E15.5 Myc$^{i\Delta EC}$ and control (Myc$^{flox/flox}$) embryos. Arrowhead denotes area with lymphedema. FIG. 5H depicts confocal images of anterior dorsal skin with VEGFR3, PROX1 and PECAM1 staining from E15.5 Myc$^{i\Delta EC}$ and control (Myc$^{flox/flox}$) embryos. FIGS. 5I-5J depict quantification of the distance between the two leading fronts of the lymphatic vessels (FIG. 5I; n=10 embryos for control and n=5 embryos for Myc$^{i\Delta EC}$) and the number of LECs (based on PROX1 staining) per 100-μm length of lymphatic vessels (FIG. 5J; n=6 embryos for control and n=9 embryos for Myc$^{i\Delta EC}$). FIG. 5K depicts confocal images of anterior dorsal skin with VEGFR3, PROX1 and PECAM1 staining from E15.5 Myc$^{i\Delta LEC(BAC)}$ and control (Myc$^{flox/flox}$) embryos. FIGS. 5L-5M depicts quantification of the distance between the two leading fronts of the lymphatic vessels (FIG. 5L; n=7 embryos for control and n=9 embryos for Myc$^{i\Delta LEC(BAC)}$) and the number of LECs (based on PROX1 staining) per 100-μm length of lymphatic vessels (FIG. 5M; n=6 embryos for control and n=8 embryos for Myc$^{i\Delta LEC(BAC)}$). *$p<0.05$; $p<0.01$; *$p<0.001$; ns=non-significant.

FIGS. 6A-6G are a series of images and graphs demonstrating the effect of FGF signaling inhibition on lymphatic development in mice and the expression of FGFRs in mouse and human LECs. FIG. 6A depicts Western blot analysis of phosphorylated and total ERK in HDLECs infected with adenovirus encoding GFP, DN-FGFR1 or sFGFR1-IIIC. Cells were serum-starved and stimulated with FGF2 for the indicated time periods. FIGS. 6B-6C depict representative images (FIG. 6B) and quantification (FIG. 6C) of the tail dermal lymphatics (revealed by VEGFR3 staining) of P6 mice treated with Lac Z or sFGFR1-IIIC adenovirus. Boxed area in the left panels (scale bar, 50 µm) is presented with higher magnification in the right panels (scale bar, 25 µm). n=8 mice for Lac Z and n=10 mice for sFGFR1-IIIC. FIGS. 6D-6E depict qPCR analysis of FGFRs expression in mouse dermal LECs (isolated from E15.5 embryos by FACS) (FIG. 6D; n=3 embryos) and HDLECs (FIG. 6E; n=3 technical replicates, representative of 2 experiments). FIGS. 6F-6G depict qPCR analysis of FGFR expression in HDLECs with FGFR1 (FIG. 6F) or FGFR3 (FIG. 6G) knockdown. FGFR mRNA levels in FGFR1 or FGFR3 deficient cells were presented as values relative to those of control siRNA-treated cells. n=6 replicates (2 experiments, technical triplicates per experiment). ***$p<0.001$; ns=non-significant.

FIGS. 7A-7B depicts activation of mTmG reporter by Cdh5-CreER$^{T2}$ (7A; scale bar: 100 µm) or Prox1-CreER$^{T2(BAC)}$ (FIG. 7B; scale bar: 250 µm) in dermal LECs of E15.5 mouse embryos. FIG. 7C depicts anterior dorsal skin with VEGFR3 and PECAM1 staining from tamoxifen-treated E15.5 FGFR1$^{i\Delta LEC(BAC)}$ and FGFR1$^{flox/flox}$ embryos (scale bar: 250 µm). FIG. 7D depicts quantification of the distance between the two leading fronts of the lymphatic vessels (n=6 embryos for FGFR1$^{flox/flox}$ and n=5 embryos for FGFR1$^{i\Delta LEC(BAC)}$). FIG. 7E depicts anterior dorsal skin stained for VEGFR3 and PECAM1 from E15.5 FGFR1$^{flox/flox}$; FGFR3$^{+/+}$, FGFR1$^{flox/flox}$; FGFR3$^{+/-}$, and FGFR$^{flox/flox}$; FGFR3$^{-/-}$ embryos (scale bar: 250 µm). FIG. 7F depicts quantification of the distance between the two leading fronts of the lymphatic vessels (n=4 embryos for FGFR$^{flox/flox}$; FGFR3$^{+/+}$, n=6 embryos for FGFR$^{flox/flox}$; FGFR3$^{+/-}$, and n=2 embryos for FGFR1$^{flox/flox}$; FGFR3). Note that these embryos were not treated with tamoxifen. Dotted lines indicate the midline in FIG. 7C and FIG. 7E. ns=non-significant.

FIGS. 8A-8E are a series of images and graphs showing that endothelium-specific deletion of FGFR1/R3 from E10.5 leads to severe lymphatic development in the embryonic skin. FIG. 8A, Schematic of the experimental strategy to analyze the dermal lymphatic development of FGFR1$^{i\Delta EC}$; FGFR3$^{-/-}$ embryos. FIG. 8B depicts bright-field images of E15.5 FGFR1$^{i\Delta EC}$; FGFR3$^{-/-}$ and control (FGFR1$^{flox/flox}$; FGFR3$^{+/-}$) embryos. Arrowhead denotes area with lymphedema. FIG. 8C depicts representative images of anterior dorsal skin with VEGFR3 and PECAM1 staining from E15.5 FGFR1$^{i\Delta EC}$; FGFR3$^{-/-}$ and control (FGFR1$^{flox/flox}$; FGFR3$^{+/-}$) embryos. Double-headed arrows indicate the distance between the two leading fronts of the lymphatic vessels, which is larger in FGFR1$^{i\Delta EC}$; FGFR3$^{-/-}$ skin than in control. Boxed area in low magnification images (scale bar, 250 µm) is presented with high magnification (scale bar, 100 µm). FIGS. 8D-8E depict quantification of the distance between the two leading fronts of the lymphatic vessels (8D; n=3 litters) and the number of lymphatic branch points per mm$^2$ skin area (FIG. 8E; n=9 embryos for control and n=7 embryos for FGFR1$^{i\Delta EC}$; FGFR3$^{-/-}$). ***$p<0.001$.

FIG. 9A is a schematic of the experimental strategy to analyze the dermal lymphatic development of FGFR1$^{i\Delta EC}$; FGFR3$^{-/-}$ embryos. FIG. 9B depicts representative images of anterior dorsal skin with VEGFR3 and PECAM1 staining from E15.5 FGFR1$^{i\Delta EC}$; FGFR3$^{-/-}$ and control (FGFR1$^{flox/flox}$; FGFR3$^{+/-}$) embryos. Double-headed arrows indicate the distance between the two leading fronts of the lymphatic vessels, which is larger in FGFR1$^{i\Delta EC}$; FGFR3$^{-/-}$ skin than in control. Boxed area in low magnification images (scale bar, 250 µm) is presented with high magnification (scale bar, 100 µm). FIGS. 9C-9D depict quantification of the distance between the two leading fronts of the lymphatic vessels (FIG. 9C; n=4 litters) and the number of lymphatic branch points per mm$^2$ skin area (FIG. 9D; n=9 embryos for control and n=8 embryos for FGFR1$^{i\Delta EC}$; FGFR3$^{-/-}$). ***$p<0.001$.

FIG. 10A is a schematic of the experimental strategy to analyze the blood vessel development of FGFR1$^{i\Delta EC}$; FGFR3$^{-/-}$ embryos. FIG. 10B depicts representative images of anterior dorsal skin with PECAM1 staining from E15.5 FGFR1$^{i\Delta EC}$; FGFR3$^{-/-}$ and control (FGFR1$^{flox/flox}$; FGFR3$^{+/-}$) embryos. Scale bar, 250 µm. FIGS. 10C-10E depict quantification of the number of blood vessel branch points per mm$^2$ skin area (FIG. 10C; n=9 embryos for control and n=7 embryos for FGFR1$^{i\Delta EC}$; FGFR3$^{-/-}$), blood vessel covered area relative to skin area (FIG. 10D; n=9 embryos for control and n=7 embryos for FGFR1$^{i\Delta EC}$; FGFR3$^{-/-}$), and capillary diameter (FIG. 10E; n=6 embryos for control and n=3 embryos for FGFR1$^{i\Delta EC}$; FGFR3$^{-/-}$). FIG. 10F depicts anterior dorsal skin stained for Connexin 40 (Cx40) in E15.5 FGFR1$^{i\Delta EC}$; FGFR3$^{-/-}$ and control (FGFR$^{flox/flox}$; FGFR3$^{+/-}$) embryos. Scale bar, 250 µm. FIGS. 10G-10H depict quantification of the number of artery branch points (FIG. 10G) and artery diameter (FIG. 10H). n=6 embryos for control and n=3 embryos for FGFR1$^{i\Delta EC}$; FGFR3$^{-/-}$. *$p<0.05$; $p<0.01$; *$p<0.001$; ns=non-significant.

FIG. 11A depicts representative images of IB4-stained retinal vessels (negative images of the fluorescent signal) in P5 FGFR1$^{i\Delta EC}$ and FGFR1$^{flox/flox}$ mice. Scale bar, 500 µm. FIG. 11B depicts quantification of vascular density (AU, arbitrary unit) and the number of branch points per mm$^2$ retina area in P5 FGFR1$^{i\Delta EC}$ and FGFR1$^{flox/flox}$ mice (n=18 retinas for FGFR1$^{flox/flox}$ and n=8 retinas for FGFR1$^{i\Delta EC}$). FIG. 11C depicts representative images of IB4-stained retinal vessels (negative images of the fluorescent signal) in P5 FGFR1$^{flox/flox}$; FGFR3$^{+/-}$ and FGFR1$^{flox/flox}$; FGFR3$^{-/-}$ mice. Scale bar, 500 µm. FIG. 11D depicts quantification of vascular density (AU, arbitrary unit) and the number of branch points per mm$^2$ retina area in P5 FGFR1$^{flox/flox}$; FGFR3$^{+/-}$ and FGFR1$^{flox/flox}$; FGFR3$^{-/-}$ mice (n=16 retinas for FGFR1$^{flox/flox}$; FGFR3$^{+/-}$ and n=16 retinas for FGFR1$^{flox/flox}$; FGFR3$^{-/-}$). ns=non-significant.

FIG. 12A depicts proliferation of HDLECs treated with indicated siRNAs was measured by using xCELLigence (see Methods) (n =4 wells of samples for each condition). FIG. 12B depicts a wound healing assay to assess the migration of HDLECs transfected with siRNAs as indicated. Dotted lines outline wound area in the last time point images of HDLECs with different treatments. FIG. 12C depicts the wound closure area between the first time point and the last time point was measured and normalized to that of control siRNA treated HDLECs (n=8 imaging fields for control siRNA, FGFR1 siRNA and FGFR3 siRNA and n=7 imaging fields for FGFR1/R3 siRNAs). ***p<0.001; ns=non-significant.

FIGS. 13A-13J are a series of images and graphs illustrating the RNA-seq analysis of the transcriptome regulated by FGF signaling, expression of glycolytic enzymes, and role of HK2 in glycolysis. FIG. 13A depicts enriched nested gene ontology (nGO) categories in the FGF signaling-regulated genes, which were identified by RNA-seq analysis of FGF2 and FGFR1 siRNA-treated HDLECs (see methods for details). FIG. 13B depicts violin plots showing the $\log_2$ fold change distributions of differentially expressed genes for each enriched nGO terms. Note that width of violin plot indicates relative gene frequency at specific $\log_2$ fold change. FIG. 13C depicts measurement of flux rate of different metabolic processes (n=3 wells of samples for glucose oxidation, glycolysis and glutamine oxidation and n=4 wells of samples for fatty acid oxidation). FIG. 13D depicts measurement of glucose uptake in HDLECs treated with or without FGF2 (n=3 wells of samples for each condition). FIGS. 13E-13F depicts qPCR analysis of different isozymes of PFK (FIG. 13E; n=3-4 technical replicates, representative of 2 experiments) and PKM (FIG. 13F; n=4 technical replicates, representative of 2 experiments) in HDLECs. FIG. 13G depicts top 20 protein-coding transcripts (ranked by fold change) which were increased by FGF2 and reduced by FGFR1 siRNA (see methods for details). HK2 is the only glucose metabolic enzyme in this list. FIG. 13H depicts Western blots showing the knockdown efficiency of HK2 siRNA. FIGS. 13I-13J depict measurement of glycolytic flux rate of HDLECs with indicated treatments. For FIG. 13I depicts n=4 wells of samples for control siRNA, n=4 wells of samples for HK2 siRNA, n=3 wells of samples for control siRNA+FGF2, and n=4 wells of samples for HK2 siRNA+FGF2. For FIG. 13J, n=4 wells of samples for each condition. p<0.01; *p<0.001; ns=non-significant.

FIGS. 14A-14F are a series of images and graphs illustrating the metabolic measurement and glycolytic enzyme expression in HUVECs and HDLECs. FIG. 14A depicts measurement of glycolytic flux rate of HUVECs in the absence or presence of FGF2 (n=4 wells of samples for each condition). FIGS. 14B-14C depict representative western blot analysis (FIG. 14B) and densitometric quantification (FIG. 14C; n=5 biological replicates analyzed by 3 western blot experiments) of glycolytic enzyme expression in control or FGF2-treated HUVECs. FIG. 14D depicts measurement of glycolytic flux rate of HDLECs treated with different growth factors (n=4 wells of samples for each condition). FIGS. 14E-14F depict representative immunoblot analysis (FIG. 14E) and densitometric quantification (FIG. 14F; n=3 experiments) of glycolytic enzyme expression in HDLECs treated with different growth factors. *p<0.05; p<0.01; Sp<0.001; ns=non-significant.

FIGS. 15A-15B depict proliferation (FIG. 15A; n=4 wells of samples for each condition) and migration (FIG. 15B; n=4 imaging fields for each condition) of HDLECs with indicated siRNAs which were serum-starved and treated with or without FGF2. FIGS. 15C-15D, Proliferation (FIG. 15C; n=4 wells of samples for control siRNA+Ad-control, control siRNA+Ad-HK2 and FGFR1 siRNA+Ad-control and n=3 wells of samples for FGFR1 siRNA+Ad-HK2) and migration (FIG. 15D; n=8 imaging fields for each condition) of HDLECs with indicated siRNAs which were cultured in fully supplemented medium and treated with control or HK2 adenovirus. Proliferation was measured using xCELLigence and migration was analyzed through wound healing assay (see Methods). Wound closure area between the first time point and the last time point was measured and normalized to that of control siRNA treated HDLECs (b) or HDLECs treated with control siRNA and control adenovirus (FIG. 15D). Dotted lines outline wound area in the last time point images of HDLECs with different treatments. FIGS. 15E-15F depict representative images and quantification of microcarrier beads coated with HDLECs under treatments as indicated. Total length of LEC sprouts per bead was quantified. For FIG. 15E, n=14 beads for control siRNA, n=14 beads for HK2 siRNA, n=19 beads for control siRNA+FGF2, and n=25 beads for HK2 siRNA+FGF2. For FIG. 15F, n=25 beads for each condition. p<0.01; *p<0.001; ns=non-significant.

FIG. 16A is a schematic of the experimental strategy to analyze the lymphatic and blood vessel development of $HK2^{i\Delta EC}$ embryos. FIG. 16B depicts bright-field images of E15.5 $HK2^{i\Delta EC}$ and control ($HK2^{flox/flox}$) embryos. Arrowhead denotes area with lymphedema. FIG. 16C depicts representative images of anterior dorsal skin with VEGFR3 and PECAM1 staining from E15.5 $HK2^{i\Delta EC}$ and control ($HK2^{flox/flox}$) embryos. Double-headed arrows indicate the distance between the two leading fronts of the lymphatic vessels, which is larger in $HK2^{i\Delta EC}$ skin than in control. Boxed area in low magnification images (scale bar, 250 μm) is presented with high magnification (scale bar, 100 μm). FIGS. 16D-16E depict quantification of the distance between the two leading fronts of the lymphatic vessels (FIG. 16D; n=4 litters) and the number of lymphatic branch points per $mm^2$ skin area (FIG. 16E; n=5 embryos for control and n=6 embryos for $HK2^{i\Delta EC}$). FIGS. 16F-16G depict quantification of the number of blood vessel branch points per $mm^2$ skin area (FIG. 16F; n=5 embryos for control and n=6 embryos for $HK2^{i\Delta EC}$) and area covered by blood vessels (FIG. 16G; n=5 embryos for control and n=6 embryos for $HK2^{i\Delta EC}$). FIG. 16H depicts LECs isolated from E15.5 control and $HK2^{i\Delta EC}$ embryos and analyzed for cell cycle. Percentage of cells in different cell cycle phases was quantified (n=12 embryos for control and n=9 embryos for $HK2^{i\Delta EC}$). *p<0.05; **p<0.01; ns=non-significant.

FIG. 17A is a schematic of the experimental strategy to analyze the skin blood vessel development of $HK2^{i\Delta EC}$ embryos. FIG. 17B depicts representative images of anterior dorsal skin with PECAM1 staining from E15.5 $HK2^{i\Delta EC}$ and control ($HK2^{flox/flox}$) embryos. Scale bar: 250 μm. FIGS. 17C-17D depict quantification of the number of blood vessel branch points per $mm^2$ skin area (FIG. 17C; n=4 embryos for control and n=7 embryos for $HK2^{i\Delta EC}$) and blood vessel covered area relative to skin area (FIG. 17D; n=4 embryos for control and n=7 embryos for $HK2^{i\Delta EC}$). FIG. 17E depicts anterior dorsal skin stained for Connexin 40 (Cx40) in E15.5 $HK2^{i\Delta EC}$ and control ($HK2^{flox/flox}$) embryos. Scale bar: 250 μm. FIG. 17F depicts quantification of the number of artery branch points (n=4 embryos for control and n=7 embryos for HK2$^{i\Delta EC}$). *p<0.05; **p<0.01.

FIGS. 18A-18I are a series of images and graphs demonstrating that endothelial HK2 is required for retinal angiogenesis. FIG. 18A is a schematic of the experimental strategy to assess early formation of the retinal vasculature (P0-P5). The triangles indicate the intragastric injections of tamoxifen at P0/1/2. FIG. 18B depicts representative images of IB4-stained retinal vessels (negative images of the fluorescent signal) in P5 HK2$^{i\Delta EC}$ and control (HK2$^{flox/flox}$) mice. Scale bar, 500 µm. FIG. 18C depicts quantification of vascular progression (d is the distance between the vascular front and the optic nerve; D is the retina radius), vascular density (AU, arbitrary unit) and the number of branch points per mm$^2$ retina area. n=18 retinas for control and n=24 retinas for HK2$^{i\Delta EC}$. FIG. 18D depicts angiogenic fronts of IB4- and Erg1/2/3-stained retinal vessels in P5 HK2$^{i\Delta EC}$ and control (HK2$^{flox/flox}$) mice. Scale bar, 200 µm. FIG. 18E depicts quantification of the number of tip cells per 200-µm length of the angiogenic front (n=4 retinas for control and n=4 retinas for HK2$^{i\Delta EC}$) and the number of vascular front ECs per 200-µm$^2$ retina area (n=4 retinas for control and n=4 retinas for HK2$^{i\Delta EC}$). FIG. 18F depicts retinal vessels stained for Phospho-Histone H3 (PH3) and IB4 in P5 HK2$^{i\Delta EC}$ and control (HK2$^{flox/flox}$) mice. Scale bar, 200 µm. FIG. 18G depicts quantification of the number of PH3$^+$ IB4$^+$ endothelial cells per vascular area (normalized to control mice; n=4 retinas for control and n=4 retinas for HK2$^{i\Delta EC}$). FIG. 18H depicts staining for Collagen IV (Col4) and IB4 in the retinas of P5 HK2$^{i\Delta EC}$ and control (HK2$^{flox/flox}$) mice. Scale bar, 200 µm. FIG. 18I depicts quantification of Col4$^+$ area per IB4$^+$ area (n=6 retinas for control and n=8 retinas for HK2$^{i\Delta EC}$). p<0.01; Sp<0.001; ns=non-significant.

FIGS. 19A-19G are a series of images and graphs depicting the dinding of Myc to the regulatory region of the HK2 gene, regulation of HK2 transcription by Myc, and role of Myc in glycolysis. FIG. 19A is a schematic showing that E-boxes, which are Myc binding elements, localize in the first intron of human and mouse HK2 genes. Primers were designed to amplify the E-box containing region (green bar) in ChIP-qPCR assay. FIG. 19B depicts ChIP-qPCR analysis of immunoprecipitated DNA with Myc antibody or IgG (n=3 experiments) in HDLECs. FIG. 19C depicts qPCR analysis of HK2 expression in HDLECs transfected with control siRNA or Myc siRNA (n=4 experiments). FIG. 19D depicts qPCR analysis of HK2 mRNA in HDLECs infected with control or Myc adenovirus (n=6 experiments). FIG. 19E depicts glycolytic flux measurement of HDLECs transfected with control siRNA or Myc siRNA (n=4 wells of samples for each treatment). FIG. 19F depicts extracellular acidification rate (ECAR) in HDLECs transfected with control siRNA or Myc siRNA. n=6 replicates (3 experiments, biological duplicates per experiment). FIG. 19G depicts ECAR in HDLECs infected with control or Myc adenovirus. n=4 replicates (2 experiments, biological duplicates per experiment). *p<0.05; p<0.01; *p<0.001.

FIG. 20A depicts qPCR analysis of HK2 expression in HUVECs transfected with control siRNA or Myc siRNA (n=4 experiments). FIG. 20B depicts representative immunoblot analysis and densitometric quantification of HK2 expression in HUVECs transfected with control siRNA or Myc siRNA (n=4 experiments). FIG. 20C depicts qPCR analysis of HK2 mRNA in HUVECs infected with control or Myc adenovirus (n=2-4 experiments). FIG. 20D depicts representative western blot analysis and densitometric quantification of Myc expression in HUVECs treated with or without FGF2 (n=5 biological replicates analyzed by 3 western blot experiments). p<0.01; *p<0.001.

FIG. 21A depicts LECs isolated from the trunk region of Tg (fli1a:EGFP; prox1:KalT4-UAS:RFP) by flow cytometry. FIG. 21B is a graph that depicts qPCR analysis of FGFR mRNA levels in zebrafish LECs.

FIGS. 22A and 22B depict confocal images (FIG. 22A) and quantification (FIG. 22B) of 53 hpf Tg (fli1a:EGFP) embryos treated with SU5402 (0.25 µM) or DMSO (control). Parachordal line (PL) is indicated by arrows. Asterisks indicate missing PL. The length of PL per imaging field was quantified (n=5 embryos).

FIGS. 22C and 22D depict representative images (FIG. 22C) and quantification (FIG. 22D) of 4 dpf Tg (kdrl:EGFP; prox1:KalT4-UAS:RFP) embryos treated with SU5402 (1 µM) or DMSO (control). The length of the thoracic duct (TD) per imaging field was quantified (n=19 embryos for control, n=20 embryos for SU5402).

FIGS. 22E-22F depict confocal images (FIG. 22E) and quantification (FIG. 22F) of 4 dpf Tg(hsp70l:dnfgfr1-EGFP; prox1:KalT4-UAS:RFP) embryos. The TD length per imaging field was quantified (n=9 embryos for control, n=8 embryos for DN-FGFR1). White arrows indicate the well-formed TD in control embryos, while defective formation of the TD was denoted by white asterisks. White arrowheads indicate dorsal aorta (DA). Scale bar, 25 µm (FIGS. 22A, 22C and 22E). *p<0.05, ***p<0.001.

FIG. 23A depicts Western blot analysis of phosphorylated and total ERK in HDLECs infected with adenovirus encoding GFP, DN-FGFR1 or sFGFR1-IIIC. Cells were serum-starved and stimulated with FGF2 for indicated time periods. FIGS. 23B and 23C depict representative images (FIG. 23B) and quantification (FIG. 23C) of the dermal lymphatics (revealed by VEGFR3 staining) of P6 mice treated with Lac Z or sFGFR1-IIIC adenovirus. Boxed area in left panels (scale bar, 50 µm) is presented with higher magnification in right panels (scale bar, 25 µm). n=8 mice for Lac Z, n=10 mice for sFGFR1-IIIC. ***p<0.001.

DETAILED DESCRIPTION OF THE INVENTION

Figure 1A:
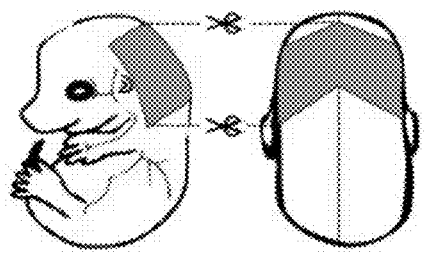

The invention features compositions and methods that are useful for treating vascular development in a subject in need thereof. The invention is based, at least in part, on the discovery of a key molecular mechanism responsible for vasculature growth and angiogenesis progression. The molecular mechanism is mainly based on the relationship between fibroblast growth factor (FGF) signaling, its receptors (FGFR) and the glycolytic enzyme hexokinase 2 (HK2).

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

By "agent" is meant any small molecule chemical compound, antibody, nucleic acid molecule, or polypeptide, or fragments thereof. In some embodiments, the agent is a nucleic acid molecule.

By "alteration" is meant a change (increase or decrease) in the expression levels or activity of a gene or polypeptide as detected by standard art known methods such as those described herein. In some embodiments, an alteration in expression level includes a 10% change in expression levels, a 25% change, a 40% change, and a 50% or greater change in expression levels.

"Biological sample" as used herein means a biological material isolated from a subject, including any tissue, cell, fluid, or other material obtained or derived from the subject. In some embodiments, the subject is human. The biological sample may contain any biological material suitable for detecting the desired analytes, and may comprise cellular and/or non-cellular material obtained from the subject. In certain embodiments, the biological sample is an endothelial cell. In certain embodiments, the endothelial cell is a blood or a lymphatic endothelial cell. Biological samples include tissue samples (e.g., cell samples, biopsy samples), such as tissue from the heart or aorta. Biological samples also include bodily fluids, including, but not limited to, blood, blood serum, plasma, saliva, and urine.

By "capture reagent" is meant a reagent that specifically binds a nucleic acid molecule or polypeptide to select or isolate the nucleic acid molecule or polypeptide. In some embodiments, the capture reagent is a probe or primer that specifically binds a polynucleotide encoding a FGF signaling polypeptide.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected. In some embodiments, a level of a FGF signaling polypeptide or polynucleotide is detected.

By "disease" is meant any condition or disorder that damages or interferes with the normal function of a cell, tissue, or organ. Examples of diseases include atherosclerosis, pulmonary hypertension, and chronic inflammation induced fibrosis.

By "effective amount" is meant the amount of a required to ameliorate the symptoms of a disease relative to an untreated patient. In particular embodiments, the disease is associated with angiogenesis or lymphangiogenesis. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In some embodiments, an effective amount of an agent that modulates activity or level of a FGF signaling polypeptide, FGFR polypeptide or HK2 is an amount of the agent that reduces the excessive vascular development in a mammal in need thereof.

As used herein, a "FGF signaling polypeptide" is meant a member or component of a fibroblast growth factor (FGF) signaling pathway (also refer to as basic fibroblast growth factor (bFGF)). In some embodiments the FGF signaling polypeptide is FGF2 polypeptide.

In some embodiments, the FGF2 polypeptide is from a human. In some embodiments, by "FGF2 polypeptide" is meant a polypeptide or fragment thereof having at least about 85% amino acid identity to GenBank Accession No. NP_001997.5 and having a biological activity of a FGF2 polypeptide. Biological activities of a FGF2 polypeptide include binding heparin and possessing mitogenic and angiogenic activities. The sequence at GenBank Accession No. NP_001997.5 is reproduced below (SEQ ID NO: 19):

```
  1  mvgvgggdve dvtprpggcq isgrgargcn gipgaaawea alprrrprrh psvnprsraa
 61  gsprtrgrrt eerpsgsrlg drgrgralpg grlggrgrgr apervggrgr grgtaapraa
121  paargsrpgp agtmaagsit tlpalpedgg sgafppghfk dpkrlyckng gfflrihpdg
181  rvdgvreksd phiklqlqae ergvvsikgv canrylamke dgrllaskcv tdecffferl
241  esnnyntyrs rkytswyval krtgqyklgs ktgpgqkail flpmsaks
```

By "FGF2 polynucleotide" is meant a polynucleotide encoding a FGF2 polypeptide. An exemplary FGF2 polynucleotide sequence is provided at GenBank Accession No. NM_002006.4. The exemplary sequence provided at GenBank Accession No. NM_002006.4 is reproduced below (SEQ ID No: 20).

```
  1  cggcccaga aacccgagc gagtaggggg cggcgcgcag gagggaggag aactgggggc
 61  gcgggaggct ggtgggtgtg gggggtggag atgtagaaga tgtgacgccg cggcccggcg
121  ggtgccagat tagcggacgc ggtgcccgcg gttgcaacgg gatcccgggc gctgcagctt
181  gggaggcggc tctccccagg cggcgtccgc ggagacaccc atccgtgaac cccaggtccc
241  gggccgccgg ctcgccgcgc accagggcc ggcggacaga agagcggccg agcggctcga
```

-continued

```
 301   ggctggggga ccgcgggcgc ggccgcgcgc tgccgggcgg gaggctgggg ggccggggcc
 361   ggggccgtgc cccggagcgg gtcggaggcc ggggccgggg ccggggggacg gcggctcccc
 421   gcgcggctcc agcggctcgg ggatcccggc cgggccccgc aggaccatg  gcagccggga
 481   gcatcaccac gctgcccgcc ttgcccgagg atggcggcag cggcgccttc ccgccggcc
 541   acttcaagga ccccaagcgg ctgtactgca aaacgggggg cttcttcctg cgcatccacc
 601   ccgacggccg agttgacggg gtccgggaga gagcgaccc  tcacatcaag ctacaacttc
 661   aagcagaaga gagaggagtt gtgtctatca aaggagtgtg tgctaaccgt tacctggcta
 721   tgaaggaaga tggaagatta ctggcttcta aatgtgttac ggatgagtgt ttcttttttg
 781   aacgattgga atctaataac tacaatactt accggtcaag gaaatacacc agttggtatg
 841   tggcactgaa acgaactggg cagtataaac ttggatccaa acaggacct  gggcagaaag
 901   ctatactttt tcttccaatg tctgctaaga gctgatttta atggccacat ctaatctcat
 961   ttcacatgaa agaagaagta tattttagaa atttgttaat gagagtaaaa gaaataaat
1021   gtgtatagct cagtttggat aattggtcaa acaattttttt atccagtagt aaaatatgta
1081   accattgtcc cagtaaagaa aaataacaaa agttgtaaaa tgtatattct cccttttata
1141   ttgcatctgc tgttacccag tgaagcttac ctagagcaat gatcttttc  acgcatttgc
1201   tttattcgaa aagaggcttt taaaatgtgc atgtttagaa acaaaatttc ttcatggaaa
1261   tcatatacat tagaaaatca cagtcagatg tttaatcaat ccaaaatgtc cactatttct
1321   tatgtcattc gttagtctac atgtttctaa acatataaat gtgaatttaa tcaattcctt
1381   tcatagtttt ataattctct ggcagttcct tatgatagag tttataaaac agtcctgtgt
1441   aaactgctgg aagttcttcc acagtcaggt caattttgtc aaacccttct ctgtacccat
1501   acagcagcag cctagcaact ctgctggtga tgggagttgt attttcagtc ttcgccaggt
1561   cattgagatc catccactca catcttaagc attcttcctg gcaaaaattt atggtgaatg
1621   aatatggctt taggcggcag atgatataca tatctgactt cccaaaagct ccaggatttg
1681   tgtgctgttg ccgaatactc aggacggacc tgaattctga ttttataccaa gtctcttcaa
1741   aaacttctcg aaccgctgtg tctcctacgt aaaaaaagag atgtacaaat caataataat
1801   tacactttta gaaactgtat catcaaagat tttcagttaa agtagcatta tgtaaaggct
1861   caaaacatta ccctaacaaa gtaaagtttt caatacaaat tctttgcctt gtggatatca
1921   agaaatccca aaatattttc ttaccactgt aaattcaaga agcttttgaa atgctgaata
1981   tttctttggc tgctacttgg aggcttatct acctgtacat ttttggggtc agctcttttt
2041   aacttcttgc tgctcttttt cccaaaaggt aaaaatatag attgaaaagt taaacatttt
2101   tgcatggctg cagttccttt gttcttgag  ataagattcc aaagaactta gattcatttc
2161   ttcaacaccg aaatgctgga ggtgtttgat cagttttcaa gaaacttgga atataaataa
2221   ttttataatt caacaaaggt tttcacattt tataaggtta ttttttcaat taaatgcaaa
2281   tttgtgtggc aggatttttta ttgccattaa catattttg  tggctgcttt ttctacacat
2341   ccagatggtc cctctaactg ggctttctct aattttgtga tgttctgtca ttgtctccca
2401   aagtatttag gagaagccct ttaaaaagct gccttcctct accactttgc tggaaagctt
2461   cacaattgtc acagacaaag attttttgttc caatactcgt tttgcctcta ttttttcttgt
2521   ttgtcaaata gtaaatgata tttgcccttg cagtaattct actggtgaaa acatgcaaa
2581   gaagaggaag tcacagaaac atgtctcaat tcccatgtgc tgtgactgta gactgtctta
2641   ccatagactg tcttacccat cccctggata tgctcttgtt ttttcccctct aatagctatg
```

-continued

```
2701  gaaagatgca tagaaagagt ataatgtttt aaaacataag gcattcgtct gccattttc
2761  aattacatgc tgacttccct tacaattgag atttgcccat aggttaaaca tggttagaaa
2821  caactgaaag cataaaagaa aaatctaggc cgggtgcagt ggctcatgcc tatattccct
2881  gcactttggg aggccaaagc aggaggatcg cttgagccca ggagttcaag accaacctgg
2941  tgaaacccg tctctacaaa aaacacaaa aaatagccag gcatggtggc gtgtacatgt
3001  ggtctcagat acttgggagg ctgaggtggg agggttgatc acttgaggct gagaggtcaa
3061  ggttgcagtg agccataatc gtgccactgc agtccagcct aggcaacaga gtgagacttt
3121  gtctcaaaaa aagagaaatt ttccttaata agaaaagtaa ttttttactct gatgtgcaat
3181  acatttgtta ttaaatttat tatttaagat ggtagcacta gtcttaaatt gtataaaata
3241  tcccctaaca tgtttaaatg tccatttta ttcattatgc tttgaaaaat aattatgggg
3301  aaatacatgt ttgttattaa atttattatt aaagatagta gcactagtct taaatttgat
3361  ataacatctc ctaacttgtt taaatgtcca ttttattct ttatgtttga aaataaatta
3421  tggggatcct atttagctct tagtaccact aatcaaaagt tcggcatgta gctcatgatc
3481  tatgctgttt ctatgtcgtg aagcaccgg atgggggtag tgagcaaatc tgccctgctc
3541  agcagtcacc atagcagctc actgaaaatc agcactgcct gagtagtttt gatcagttta
3601  acttgaatca ctaactgact gaaaattgaa tgggcaaata agtgcttttg tctccagagt
3661  atgcgggaga cccttccacc tcaagatgga tatttcttcc ccaaggattt caagatgaat
3721  tgaatttt aatcaagata gtgtgcttta ttctgttgta tttttatta ttttaatata
3781  ctgtaagcca aactgaaata acatttgctg ttttataggt ttgaagaaca taggaaaaac
3841  taagaggttt tgttttatt tttgctgatg aagagatatg tttaaatatg ttgtattgtt
3901  ttgtttagtt acaggacaat aatgaaatgg agtttatatt tgttatttct attttgttat
3961  atttaataat agaattagat tgaaataaaa tataatggga aataatctgc agaatgtggg
4021  ttttcctggt gtttccctct gactctagtg cactgatgat ctctgataag gctcagctgc
4081  tttatagttc tctggctaat gcagcagata ctcttcctgc cagtggtaat acgattttt
4141  aagaaggcag tttgtcaatt ttaatcttgt ggatcctt atactcttag ggtattttt
4201  tatacaaaag ccttgaggat tgcattctat tttctatatg accctcttga tatttaaaaa
4261  acactatgga taacaattct tcatttacct agtattatga aagaatgaag gagttcaaac
4321  aaatgtgttt cccagttaac tagggtttac tgtttgagcc aatataaatg tttaactgtt
4381  tgtgatggca gtattcctaa agtacattgc atgttttcct aaatacagag tttaaataat
4441  ttcagtaatt cttagatgat tcagcttcat cattaagaat atctttgtt ttatgttgag
4501  ttagaaatgc cttcatatag acatagtctt tcagacctct actgtcagtt ttcatttcta
4561  gctgctttca gggttttatg aattttcagg caaagcttta atttatacta agcttaggaa
4621  gtatggctaa tgccaacggc agtttttttc ttcttaattc cacatgactg aggcatatat
4681  gatctctggg taggtgagtt gttgtgacaa ccacaagcac ttttttttt tttaaagaaa
4741  aaaggtagt gaatttttaa tcatctgac tttaagaagg attctggagt atacttaggc
4801  ctgaaattat atatatttgg cttggaaatg tgttttcttt caattcatc tacaagtaag
4861  tacagctgaa attcagagga cccataagag ttcacatgaa aaaaatcaat ttatttgaaa
4921  aggcaagatg caggagagag gaagccttgc aaacctgcag actgcttttt gcccaatata
4981  gattgggtaa ggctgcaaaa cataagctta attagctcac atgctctgct ctcacgtggc
5041  accagtggat agtgtgagag aattaggctg tagaacaaat ggccttctct ttcagcattc
5101  acaccactac aaaatcatct tttatatcaa cagaagaata agcataaact aagcaaaagg
```

```
5161  tcaataagta cctgaaacca agattggcta gagatatatc ttaatgcaat ccattttctg
5221  atggattgtt acgagttggc tatataatgt atgtatggta ttttgatttg tgtaaaagtt
5281  ttaaaaatca agctttaagt acatggacat ttttaaataa aatatttaaa gacaatttag
5341  aaaattgcct taatatcatt gttggctaaa tagaataggg acatgcata ttaaggaaaa
5401  ggtcatggag aaataatatt ggtatcaaac aaatacattg atttgtcatg atacacattg
5461  aatttgatcc aatagtttaa ggaataggta ggaaaatttg gtttctattt ttcgatttcc
5521  tgtaaatcag tgacataaat aattcttagc ttattttata tttccttgtc ttaaatactg
5581  agctcagtaa gttgtgttag gggattattt ctcagttgag actttcttat atgacatttt
5641  actatgtttt gacttcctga ctattaaaaa taaatagtag atacaatttt cataaagtga
5701  agaattatat aatcactgct ttataactga ctttattata tttatttcaa agttcattta
5761  aaggctacta ttcatcctct gtgatggaat ggtcaggaat ttgttttctc atagtttaat
5821  tccaacaaca atattagtcg tatccaaaat aacctttaat gctaaacttt actgatgtat
5881  atccaaagct tctcattttc agacagatta atccagaagc agtcataaac agaagaatag
5941  gtggtatgtt cctaatgata ttatttctac taatggaata aactgtaata ttagaaatta
6001  tgctgctaat tatatcagct ctgaggtaat ttctgaaatg ttcagactca gtcggaacaa
6061  attggaaaat ttaaatttt  attcttagct ataaagcaag aaagtaaaca cattaatttc
6121  ctcaacattt ttaagccaat taaaaatata aaagatacac accaatatct tcttcaggct
6181  ctgacaggcc tcctggaaac ttccacatat ttttcaactg cagtataaag tcagaaaata
6241  aagttaacat aactttcact aacacacaca tatgtagatt tcacaaaatc cacctataat
6301  tggtcaaagt ggttgagaat atattttta gtaattgcat gcaaaatttt tctagcttcc
6361  atcctttctc cctcgtttct tctttttttg ggggagctgg taactgatga aatcttttcc
6421  cacctttct  cttcaggaaa tataagtggt tttgtttggt taacgtgata cattctgtat
6481  gaatgaaaca ttggagggaa acatctactg aatttctgta atttaaaata ttttgctgct
6541  agttaactat gaacagatag aagaatctta cagatgctgc tataaataag tagaaaatat
6601  aaatttcatc actaaaatat gctatttta  aatctatttc ctatattgta tttctaatca
6661  gatgtattac tcttattatt tctattgtat gtgttaatga ttttatgtaa aaatgtaatt
6721  gcttttcatg agtagtatga ataaaattga ttagtttgtg ttttcttgtc tccc
```

In some embodiments, the FGF signaling polypeptide is FGFR1 polypeptide, or FGFR3 polypeptide.

In some embodiments, the FGFR1 polypeptide is from a human. In some embodiments, by "FGFR1 polypeptide" is meant a polypeptide or fragment thereof having at least about 85% amino acid identity to GenBank Accession No. NP_001167534.1 and having a biological activity of a FGFR1 polypeptide. Biological activities of a FGFR1 polypeptide include cell surface receptor activity and tyrosine kinase activity. The sequence at GenBank Accession No. NP_001167534.1 is reproduced below (SEQ ID NO: 21):

```
  1  mwswkcllfw avlvtatlct arpsptlpeq aqpwgapvev esflvhpgdl lqlrcrlrdd
 61  vqsinwlrdg vqlaesnrtr itgeevevqd svpadsglya cvtsspsgsd ttyfsvnvsd
121  alpssedddd dddssseeke tdntkpnrmp vapywtspek mekklhavpa aktvkfkcps
181  sgtpnptlrw lkngkefkpd hriggykvry atwsiimdsv vpsdkgnytc iveneygsin
241  htyqldvver sphrpilqag lpanktvalg snvefmckvy sdpqphiqwl khievngski
301  gpdnlpyvqi lktagvnttd kemevlhlrn vsfedageyt clagnsigls hhsawltvle
361  aleerpavmt splyleiiiy ctgafliscm vgsvivykmk sgtkksdfhs qmavhklaks
421  iplrrqvsad ssasmnsgvl lvrpsrlsss gtpmlagvse yelpedprwe lprdrlvlgk
```

```
481  plgegcfgqv  vlaeaigldk  dkpnrvtkva  vkmlksdate  kdlsdlisem  emmkmigkhk 541  niinllgact  qdgplyvive  yaskgnlrey  lqarrppgle  ycynpshnpe  eqlsskdlvs 601  cayqvargme  ylaskkcihr  dlaarnvlvt  ednvmkiadf  glardihhid  yykkttngrl 661  pvkwmapeal  fdriythqsd  vwsfgvllwe  iftlggspyp  gvpveelfkl  lkeghrmdkp 721  snctnelymm  mrdcwhavps  qrptfkqlve  dldrivalts  nqeyldlsmp  ldqyspsfpd 781  trsstcssge  dsvfsheplp  eepclprhpa  qlangglkrr
```

By "FGFR1 polynucleotide" is meant a polynucleotide encoding a FGFR1 polypeptide. An exemplary FGFR1 polynucleotide sequence is provided at GenBank Accession No. NM_001174063.1. The exemplary sequence provided at GenBank Accession No. NM_001174063.1 is reproduced below (SEQ ID No: 22).

```
   1  agatgcaggg  gcgcaaacgc  caaaggagac  caggctgtag  gaagagaagg  gcagagcgcc
  61  ggacagctcg  gcccgctccc  cgtcctttgg  ggccgcggct  ggggaactac  aaggcccagc
 121  aggcagctgc  aggggcgga   ggcggaggag  ggaccagcgc  gggtgggagt  gagagagcga
 181  gccctcgcgc  cccgccggcg  catagcgctc  ggagcgctct  tgcggccaca  ggcgcggcgt
 241  cctcggcggc  gggcggcagc  tagcgggagc  cgggacgccg  gtgcagccgc  agcgcgcgga
 301  ggaacccggg  tgtgccggga  gctgggcggc  cacgtccgga  cgggaccgag  acccctcgta
 361  gcgcattgcg  gcgacctcgc  cttccccggc  cgcgagcgcg  ccgctgcttg  aaaagccgcg
 421  gaacccaagg  acttttctcc  ggtccgagct  cggggcgccc  cgcagggcgc  acggtacccg
 481  tgctgcagtc  gggcacgccg  cggcgccggg  gcctccgcag  ggcgatggag  cccggtctgc
 541  aaggaaagtg  aggcgccgcc  gctgcgttct  ggaggagggg  ggcacaaggt  ctggagaccc
 601  cgggtggcgg  acgggagccc  tccccccgcc  ccgcctccgg  ggcaccagct  ccggctccat
 661  tgttcccgcc  cgggctggag  gcgccgagca  ccgagcgccg  ccgggagtcg  agcgccggcc
 721  gcggagctct  tgcgacccccg  ccaggacccg  aacagagccc  gggggcggcg  ggccggagcc
 781  ggggacgcgg  gcacacgccc  gctcgcacaa  gccacggcgg  actctcccga  ggcggaacct
 841  ccacgccgag  cgagggtcag  tttgaaaagg  aggatcgagc  tcactgtgga  gtatccatgg
 901  agatgtggag  ccttgtcacc  aacctctaac  tgcagaactg  ggatgtggag  ctggaagtgc
 961  ctcctcttct  gggctgtgct  ggtcacagcc  acactctgca  ccgctaggcc  gtccccgacc
1021  ttgcctgaac  aagcccagcc  ctggggagcc  cctgtggaag  tggagtcctt  cctggtccac
1081  cccggtgacc  tgctgcagct  tcgctgtcgg  ctgcgggacg  atgtgcagag  catcaactgg
1141  ctgcgggacg  gggtgcagct  ggcggaaagc  aaccgcaccc  gcatcacagg  ggaggaggtg
1201  gaggtgcagg  actccgtgcc  cgcagactcc  ggcctctatg  cttgcgtaac  cagcagcccc
1261  tcgggcagtg  acaccaccta  cttctccgtc  aatgtttcag  atgctctccc  ctcctcggag
1321  gatgatgatg  atgatgatga  ctcctcttca  gaggagaaag  aaacagataa  caccaaacca
1381  aaccgtatgc  ccgtagctcc  atattggaca  tccccagaaa  agatggaaaa  gaaattgcat
1441  gcagtgccgg  ctgccaagac  agtgaagttc  aaatgccctt  ccagtgggac  cccaaacccc
1501  acactgcgct  ggttgaaaaa  tggcaaagaa  ttcaaacctg  accacagaat  tggaggctac
1561  aaggtccgtt  atgccacctg  gagcatcata  atggactctg  tggtgccctc  tgacaagggc
1621  aactacacct  gcattgtgga  gaatgagtac  ggcagcatca  accacacata  ccagctggat
1681  gtcgtggagc  ggtcccctca  ccggcccatc  ctgcaagcag  ggttgcccgc  caacaaaaca
1741  gtggccctgg  gtagcaacgt  ggagttcatg  tgtaaggtgt  acagtgaccc  gcagccgcac
1801  atccagtggc  taaagcacat  cgaggtgaat  gggagcaaga  ttggcccaga  caacctgcct
```

-continued

```
1861  tatgtccaga tcttgaagac tgctggagtt aataccaccg acaaagagat ggaggtgctt
1921  cacttaagaa atgtctcctt tgaggacgca ggggagtata cgtgcttggc gggtaactct
1981  atcggactct cccatcactc tgcatggttg accgttctgg aagccctgga agagaggccg
2041  gcagtgatga cctcgcccct gtacctggag atcatcatct attgcacagg ggccttcctc
2101  atctcctgca tggtggggtc ggtcatcgtc tacaagatga agagtggtac caagaagagt
2161  gacttccaca gccagatggc tgtgcacaag ctggccaaga gcatccctct cgcagacag
2221  gtgtctgctg actccagtgc atccatgaac tctggggttc ttctggttcg gccatcacgg
2281  ctctcctcca gtgggactcc catgctagca ggggtctctg agtatgagct tcccgaagac
2341  cctcgctggg agctgcctcg ggacagactg gtcttaggca aacccctggg agagggctgc
2401  tttgggcagg tggtgttggc agaggctatc gggctggaca aggacaaacc caaccgtgtg
2461  accaaagtgg ctgtgaagat gttgaagtcg gacgcaacag agaaagactt gtcagacctg
2521  atctcagaaa tggagatgat gaagatgatc gggaagcata agaatatcat caacctgctg
2581  ggggcctgca cgcaggatgg tcccttgtat gtcatcgtgg agtatgcctc aagggcaac
2641  ctgcgggagt acctgcaggc ccggaggccc cagggctgg aatactgcta aacccccagc
2701  cacaacccag aggagcagct ctcctccaag acctggtgt cctgcgccta ccaggtggcc
2761  cgaggcatgg agtatctggc tccaagaag tgcatacacc gagacctggc agccaggaat
2821  gtcctggtga cagaggacaa tgtgatgaag atagcagact ttggcctcgc acgggacatt
2881  caccacatcg actactataa aaagacaacc aacggccgac tgcctgtgaa gtggatggca
2941  cccgaggcat tatttgaccg gatctacacc caccagagtg atgtgtggtc tttcggggtg
3001  ctcctgtggg agatcttcac tctgggcggc tccccatacc ccggtgtgcc tgtggaggaa
3061  cttttcaagc tgctgaagga gggtcaccgc atggacaagc ccagtaactg caccaacgag
3121  ctgtacatga tgatgcggga ctgctggcat gcagtgccct cacagagacc caccttcaag
3181  cagctggtgg aagacctgga ccgcatcgtg gccttgacct ccaaccagga gtacctggac
3241  ctgtccatgc cctggaccag tactcccccc agctttcccg cacccggag ctctacgtgc
3301  tcctcagggg aggattccgt cttctctcat gagccgctgc ccgaggagcc ctgcctgccc
3361  cgacacccag cccagcttgc caatggcgga ctcaaacgcc gctgactgcc acccacacgc
3421  cctccccaga ctccaccgtc agctgtaacc ctcacccaca gcccctgctg ggcccaccac
3481  ctgtccgtcc ctgtcccctt tcctgctggc aggagccggc tgcctaccag gggccttcct
3541  gtgtggcctg ccttcacccc actcagctca cctctcccct cacctcctct ccacctgctg
3601  gtgagaggtg caaagaggca gatctttgct gccagccact tcatcccctc ccagatgttg
3661  gaccaacacc cctccctgcc accaggcact gcctggaggg cagggagtgg gagccaatga
3721  acaggcatgc aagtgagagc ttcctgagct ttctcctgtc ggtttggtct gttttgcctt
3781  cacccataag cccctcgcac tctggtggca ggtgccttgt cctcagggct acagcagtag
3841  ggaggtcagt gcttcgtgcc tcgattgaag gtgacctctg ccccagatag gtggtgccag
3901  tggcttatta attccgatac tagtttgctt tgctgaccaa atgcctggta ccagaggatg
3961  gtgaggcgaa ggccaggttg ggggcagtgt gtgggccctg ggcccagcc caaactggg
4021  ggctctgtat atagctatga agaaaacaca aagtgtataa atctgagtat atatttacat
4081  gtcttttta aagggtcgtt accagagatt tacccatcgg gtaagatgct cctggtggct
4141  gggaggcatc agttgctata tattaaaaac aaaaaagaaa aaaaggaaa atgttttaa
4201  aaaggtcata tattttttgc tacttttgct gttttatttt tttaaattat gttctaaacc
```

-continued

```
4261  tattttcagt ttaggtccct caataaaaat tgctgctgct tcatttatct atgggctgta
4321  tgaaaagggt gggaatgtcc actggaaaga agggacaccc acgggccctg gggctaggtc
4381  tgtcccgagg gcaccgcatg ctcccggcgc aggttccttg taacctcttc ttcctaggtc
4441  ctgcacccag acctcacgac gcacctcctg cctctccgct gcttttggaa agtcagaaaa
4501  agaagatgtc tgcttcgagg gcaggaaccc catccatgca gtagaggcgc tgggcagaga
4561  gtcaaggccc agcagccatc gaccatggat ggtttcctcc aaggaaaccg gtggggttgg
4621  gctggggagg gggcacctac ctaggaatag ccacggggta gagctacagt gattaagagg
4681  aaagcaaggg cgcggttgct cacgcctgta atcccagcac tttgggacac cgaggtgggc
4741  agatcacttc aggtcaggag tttgagacca gcctggccaa cttagtgaaa ccccatctct
4801  actaaaaatg caaaaattat ccaggcatgg tggcacacgc ctgtaatccc agctccacag
4861  gaggctgagg cagaatccct tgaagctggg aggcggaggt tgcagtgagc cgagattgcg
4921  ccattgcact ccagcctggg caacagagaa aacaaaaagg aaaacaaatg atgaaggtct
4981  gcagaaactg aaacccagac atgtgtctgc cccctctatg tgggcatggt tttgccagtg
5041  cttctaagtg caggagaaca tgtcacctga ggctagtttt gcattcaggt ccctggcttc
5101  gtttcttgtt ggtatgcctc cccagatcgt ccttcctgta tccatgtgac cagactgtat
5161  ttgttgggac tgtcgcagat cttggcttct tacagttctt cctgtccaaa ctccatcctg
5221  tccctcagga acggggggaa aattctccga atgttttggg ttttttggct gcttggaatt
5281  tacttctgcc acctgctggt catcactgtc ctcactaagt ggattctggc tcccccgtac
5341  ctcatggctc aaactaccac tcctcagtcg ctatattaaa gcttatattt tgctggatta
5401  ctgctaaata caaagaaag ttcaatatgt tttcatttct gtagggaaaa tgggattgct
5461  gctttaaatt tctgagctag ggattttttg gcagctgcag tgttggcgac tattgtaaaa
5521  ttctctttgt ttctctctgt aaatagcacc tgctaacatt acaatttgta tttatgttta
5581  aagaaggcat catttggtga acagaactag gaaatgaatt tttagctctt aaaagcattt
5641  gctttgagac cgcacaggag tgtctttcct tgtaaaacag tgatgataat ttctgccttg
5701  gccctacctt gaagcaatgt tgtgtgaagg gatgaagaat ctaaaagtct tcataagtcc
5761  ttgggagagg tgctagaaaa atataaggca ctatcataat tacagtgatg tccttgctgt
5821  tactactcaa atcacccaca aatttcccca aagactgcgc tagctgtcaa ataaaagaca
5881  gtgaaattga cctga
```

In some embodiments, the FGFR3 polypeptide is from a human. In some embodiments, by "FGFR3 polypeptide" is meant a polypeptide or fragment thereof having at least about 85% amino acid identity to GenBank Accession No. NP_000133.1 and having a biological activity of a FGFR3 polypeptide. Biological activities of a FGFR3 polypeptide include cell surface receptor activity and tyrosine kinase activity. The sequence at GenBank Accession No. NP_000133.1 is reproduced below (SEQ ID NO: 23):

```
  1  mgapacalal cvavaivaga sseslgteqr vvgraaevpg pepgqqeqlv fgsgdavels
 61  cpppgggpmg ptvwvkdgtg lvpservlvg pqrlqvlnas hedsgayscr qrltqrvlch
121  fsvrvtdaps sgddedgede aedtgvdtga pywtrpermd kkllavpaan tvrfrcpaag
181  nptpsiswlk ngrefrgehr iggiklrhqq wslvmesvvp sdrgnytcvv enkfgsirqt
241  ytldvlersp hrpilqaglp anqtavlgsd vefhckvysd aqphiqwlkh vevngskvgp
301  dgtpyvtvlk taganttdke levlslhnvt fedageytcl agnsigfshh sawlvvlpae
361  eelveadeag svyagilsyg vgfflfilvv aavtlcrlrs ppkkglgspt vhkisrfplk
421  rqvslesnas mssntplvri arlssgegpt lanvselelp adpkwelsra rltlgkplge
```

```
481  gcfgqvvmae aigidkdraa kpvtvavkml kddatdkdls dlvsememmk migkhkniin 541  llgactqggp lyvlveyaak gnlreflrar rppgldysfd tckppeeqlt fkdlvscayq 601  vargmeylas qkcihrdlaa rnvlvtednv mkiadfglar dvhnldyykk ttngrlpvkw 661  mapealfdrv ythqsdvwsf gvllweiftl ggspypgipv eelfkllkeg hrmdkpanct 721  hdlymimrec whaapsqrpt fkqlvedldr vltvtstdey ldlsapfeqy spggqdtpss 781  sssgddsvfa hdllppapps sggsrt
```

By "FGFR3 polynucleotide" is meant a polynucleotide encoding a FGFR3 polypeptide. An exemplary FGFR3 polynucleotide sequence is provided at GenBank Accession No. NM_000142.4. The exemplary sequence provided at GenBank Accession No. NM_000142.4 is reproduced below (SEQ ID No: 24).

```
   1  gtcgcgggca gctggcgccg cgcggtcctg ctctgccggt cgcacggacg caccggcggg
  61  ccgccggccg gagggacggg gcggagctg ggcccgcgga cagcgagccg gagcgggagc
 121  cgcgcgtagc gagccgggct ccggcgctcg ccagtctccc gagcggcgcc cgcctcccgc
 181  cggtgcccgc gccgggccgt gggggcagc atgcccgcgc gcgctgcctg aggacgccgc
 241  ggcccccgcc ccgccatgg gcgcccctgc ctgcgccctc gcgctctgcg tggccgtggc
 301  catcgtggcc ggcgcctcct cggagtcctt ggggacggag cagcgcgtcg tgggcgagc
 361  ggcagaagtc ccgggcccag agcccggcca gcaggagcag ttggtcttcg gcagcgggga
 421  tgctgtggag ctgagctgtc ccccgcccgg gggtggtccc atggggccca ctgtctgggt
 481  caaggatggc acaggctgg tgccctcgga gcgtgtcctg gtgggccccc agcggctgca
 541  ggtgctgaat gcctcccacg aggactccgg ggcctacagc tgccggcagc ggctcacgca
 601  gcgcgtactg tgccacttca gtgtgcgggt gacagacgct ccatcctcgg agatgacga
 661  agacgggag gacgaggctg aggacacagg tgtggacaca ggggcccctt actggacacg
 721  gcccgagcgg atggacaaga gctgctggc cgtgccggcc gccaacaccg tccgcttccg
 781  ctgcccagcc gctggcaacc ccactccctc catctcctgg ctgaagaacg gcagggagtt
 841  ccgcggcgag caccgcattg gaggcatcaa gctgcggcat cagcagtgga gcctggtcat
 901  ggaaagcgtg gtgccctcgg accgcggcaa ctacacctgc gtcgtggaga caagtttgg
 961  cagcatccgg cagacgtaca cgctggacgt gctggagcgc tccccgcacc ggcccatcct
1021  gcaggcgggg ctgccggcca accagacggc ggtgctgggc agcgacgtgg agttccactg
1081  caaggtgtac agtgacgcac agccccacat ccagtggctc aagcacgtgg aggtgaatgg
1141  cagcaaggtg ggcccggacg gcacacccta cgttaccgtg ctcaagacgg cgggcgctaa
1201  caccaccgac aaggagctag aggttctctc cttgcacaac gtcacctttg aggacgccgg
1261  ggagtacacc tgcctggcgg gcaattctat tgggttttct catcactctg cgtggctggt
1321  ggtgctgcca gccgaggagg agctggtgga ggctgacgag gcgggcagtg tgtatgcagg
1381  catcctcagc tacggggtgg gcttcttcct gttcatcctg gtggtggcgg ctgtgacgct
1441  ctgccgcctg cgcagccccc ccaagaaagg cctgggctcc cccaccgtgc acaagatctc
1501  ccgcttcccg ctcaagcgac aggtgtccct ggagtccaac gcgtccatga gctccaacac
1561  accactggtg cgcatcgcaa ggctgtcctc aggggagggc cccacgctgg ccaatgtctc
1621  cgagctcgag ctgcctgccg acccaaatg ggagctgtct cgggcccggc tgaccctggg
1681  caagcccctt ggggagggct gcttcggcca ggtggtcatg gcggaggcca tcggcattga
1741  caaggaccgg gccgccaagc ctgtcaccgt agccgtgaag atgctgaaag acgatgccac
1801  tgacaaggac ctgtcggacc tggtgtctga gatggagatg atgaagatga tcgggaaaca
```

```
1861  caaaaacatc atcaacctgc tgggcgcctg cacgcagggc gggcccctgt acgtgctggt
1921  ggagtacgcg gccaagggta acctgcggga gtttctgcgg gcgcggcggc ccccgggcct
1981  ggactactcc ttcgacacct gcaagccgcc cgaggagcag ctcaccttca aggacctggt
2041  gtcctgtgcc taccaggtgg cccggggcat ggagtacttg gcctcccaga agtgcatcca
2101  cagggacctg gctgcccgca atgtgctggt gaccgaggac aacgtgatga agatcgcaga
2161  cttcgggctg gcccgggacg tgcacaacct cgactactac aagaagacaa ccaacggccg
2221  gctgcccgtg aagtggatgg cgcctgaggc cttgtttgac cgagtctaca ctcaccagag
2281  tgacgtctgg tcctttgggg tcctgctctg ggagatcttc acgctggggg gctcccccgta
2341  ccccggcatc cctgtggagg agctcttcaa gctgctgaag gagggccacc gcatggacaa
2401  gcccgccaac tgcacacacg acctgtacat gatcatgcgg gagtgctggc atgccgcgcc
2461  ctcccagagg cccaccttca gcagctggt ggaggacctg gaccgtgtcc ttaccgtgac
2521  gtccaccgac gagtacctgg acctgtcggc gccttctgag cagtactccc cgggtggcca
2581  ggacaccccc agctccagct cctcagggga cgactccgtg tttgcccacg acctgctgcc
2641  cccggcccca cccagcagtg ggggctcgcg gacgtgaagg ccactggtc cccaacaatg
2701  tgaggggtcc ctagcagccc accctgctgc tggtgcacag ccactccccg gcatgagact
2761  cagtgcagat ggagagacag ctacacagag ctttggtctg tgtgtgtgtg tgtgcgtgtg
2821  tgtgtgtgtg tgtgcacatc cgcgtgtgcc tgtgtgcgtg cgcatcttgc ctccaggtgc
2881  agaggtaccc tgggtgtccc cgctgctgtg caacggtctc ctgactggtg ctgcagcacc
2941  gagggccctt tgttctgggg ggaccccagtg cagaatgtaa gtgggcccac ccggtgggac
3001  ccccgtgggg cagggagctg ggcccgacat ggctccggcc tctgcctttg caccacggga
3061  catcacaggg tgggcctcgg cccctcccac acccaaagct gagcctgcag ggaagcccca
3121  catgtccagc accttgtgcc tggggtgtta gtggcaccgc ctccccacct ccaggctttc
3181  ccacttccca ccctgcccct cagagactga aattacgggt acctgaagat gggagccttt
3241  accttttatg caaaaggttt attccggaaa ctagtgtaca tttctataaa tagatgctgt
3301  gtatatggta tatacacata tatatatata acatatatgg aagaggaaaa ggctggtaca
3361  acggaggcct gcgaccctgg gggcacagga ggcaggcatg gccctgggcg gggcgtgggg
3421  gggcgtggag ggaggcccca gggggtctca cccatgcaag cagaggacca gggcctttc
3481  tggcaccgca gttttgtttt aaaactggac ctgtatattt gtaaagctat ttatgggccc
3541  ctggcactct tgttcccaca ccccaacact tccagcattt agctggccac atggcggaga
3601  gttttaattt ttaacttatt gacaaccgag aaggttttatc ccgccgatag agggacggcc
3661  aagaatgtac gtccagcctg ccccggagct ggaggatccc ctccaagcct aaaaggttgt
3721  taatagttgg aggtgattcc agtgaagata ttttatttcc tttgtccttt tcaggagaa
3781  ttagatttct ataggatttt tctttaggag atttatttt tggacttcaa agcaagctgg
3841  tattttcata caaattcttc taattgctgt gtgtcccagg cagggagacg gtttccaggg
3901  aggggccggc cctgtgtgca ggttccgatg ttattagatg ttacaagttt atatatatct
3961  atatatataa tttattgagt ttttacaaga tgtatttgtt gtagacttaa cacttcttac
4021  gcaatgcttc tagagttta tagcctggac tgctaccttt caaagcttgg agggaagccg
4081  tgaattcagt tggttcgttc tgtactgtta ctgggccctg agtctgggca gctgtccctt
4141  gcttgcctgc agggccatgg ctcagggtgg tctcttcttg gggcccagtg catggtggcc
4201  agaggtgtca cccaaaccgg caggtgcgat tttgttaacc cagcgacgaa ctttccgaaa
4261  aataaagaca cctggttgct aacctggaaa aaaaaaaaaa aaaa
```

In some embodiments, the HK2 polypeptide is from a human. In some embodiments, by "HK2 polypeptide" is meant a polypeptide or fragment thereof having at least about 85% amino acid identity to NCBI Accession No. NP_000180.2 and having a biological activity of a HK2 polypeptide. Biological activities of a HK2 polypeptide include the phosphorylation of glucose to produce glucose-6-phosphate during the first step of most glucose metabolism pathways. The sequence at NCBI Accession No. NP_000180.2 is reproduced below (SEQ ID No: 25):

```
  1  miashllayf ftelnhdqvq kvdqylyhmr lsdetlleis krfrkemekg lgatthptaa
 61  vkmlptfvrs tpdgtehgef laldlggtnf rvlwvkvtdn glqkvemenq iyaipedimr
121  gsgtqlfdhi aeclanfmdk lqikdkklpl gftfsfpchq tkldesflvs wtkgfkssgv
181  egrdvvalir kaiqrrgdfd idivavvndt vgtmmtcgyd dhnceigliv gtgsnacyme
241  emrhidmveg degrmcinme wgafgddgsl ndirtefdqe idmgslnpgk qlfekmisgm
301  ymgelvrlil vkmakeellf ggklspelln tgrfetkdis diegekdgir karevlmrlg
361  ldptqedcva thricqivst rsaslcaatl aavlqriken kgeerlrsti gvdgsvykkh
421  phfakrlhkt vrrlvpgcdv rflrsedgsg kgaamvtava yrladqhrar qktlehlqls
481  hdqllevkrr mkvemergls kethasapvk mlptyvcatp dgtekgdfla ldlggtnfrv
541  llvrvrngkw ggvemhnkiy aipqevmhgt gdelfdhivq ciadfleymg mkgvslplgf
601  tfsfpcqqns ldesillkwt kgfkasgceg edvvtllkea ihrreefdld vvavvndtvg
661  tmmtcgfedp hcevglivgt gsnacymeem rnvelvegee grmcvnmewg afgdngcldd
721  frtefdvavd elslnpgkqr fekmisgmyl geivrnilid ftkrgllfrg riserlktrg
781  ifetkflsqi esdclallqv railqhlgle stcddsiivk evctvvarra aqlcgagmaa
841  vvdrirenrg ldalkvtvgv dgtlyklhph fakvmhetvk dlapkcdvsf lqsedgsgkg
901  aalitavacr ireagqr
```

By "HK2 polynucleotide" is meant a polynucleotide encoding a HK2 polypeptide. An exemplary HK2 polynucleotide sequence is provided at NCBI Accession No. NM_000189.4. The exemplary sequence provided at NCBI Accession NM_000189.4 is reproduced below (SEQ ID No: 26).

```
  1  tggattatga tttttgttta tttttcctgt ttatccatat attattttc aacaatgagt
 61  attgattact tatataataa ttttaaggct gtacacattg cagacagcac cccactgttt
121  gaaaaactcc tcctcagtag aacatggcag accttcatct tccttccctg aaccttttcc
181  aaccttaggc ttgccattct ccaccagtgc taatgtcatg tctcttgaaa tctgtattga
241  agtcagtatt tcattcttgc cagtttccac tgtgtgttta aatttggagt ctggtgtcta
301  gcattagctg gggttggagc ttccactcct ctcagcattg gtaagcctcc tcacccaccc
361  catcccatgt ccaagatcac ccagttacac acttaccatc tacccagttc attcacatca
421  tcagtcccag agctgcagag atgctctttt tctacctcct acttctctgg ctcttagaga
481  ggcagcatgg gataatgggg caagcgaata gggccttaaa gtagagggac aagggttctc
541  ttccctatct gccacttatt agctatgtga cctcgtgtaa gtctcttttc ttttgagac
601  agggtctccc tctgtcacct aggctggagt acagtggtat gatcatagct cactgcagcc
661  tcgaactcct gggctcaagc tatccttcca ccttagcctt ctgagcagca gggactacag
721  gcacatgcca ccatgtccgg ctgatttatt tatttttatt tgggaagatg ggggtctcac
781  tatgtcgccc aggctggtca tgaactcctg gtctcaagca accctccaac cttggactcc
841  caaagtgctg ggattacagg tgtgagccct ggccttgcct caatttcctc atctgtaaaa
901  cggggttagt gaaactcaca tcctatcagt ggttttgagg atgggccgac tcttgtattg
```

-continued

```
 961   cctgctctag tacaatcagc agctaaggcg gctcactttc cggccgtgct acaataggta
1021   agaactagga tgctttagac gtgtgactgg gcagtgggag cccctcacat gatcccgaga
1081   tgccagacag tgtctctccg cacagggcgt gtgctggtcc agaggcccgt ttttccagtc
1141   gccccacacc ccgggtccgc gatcacgctc cccccaccca tagccgagcc tgacgcggcg
1201   gtggctcatg cgccttttcg tcccagcctt tagccacgga ccacacgtcc catctcaggc
1261   gccccgcccc tcccccgccc cccgccccg gcgcgcctcc ccaggctgcc ggctccggtg
1321   tctgagcggc cgcgcccgcg agccgtgagc gatgattggc tgcgccacgg cggcgggcgg
1381   tccgtgggcg cacacaccct ccccgcgcag ccaatgggcg tgcgcacgtc actgatccgg
1441   aggcccgcgg gccggcagcc cctcaataag ccacattgtt gcatgaaact ccggcgcagg
1501   agtcccgggc tgccgctggc aacatcgtgt cacccagcta agaaaatccg cgggcccgag
1561   ccacgcgcct gtgaatcgga gaggtcccac tgcccgagtg agccgggcg gagattcttc
1621   tcaagttgag cctcagtgat cctgtggccg aagttagcgc cttgacgtgg gacaaccgga
1681   cacgtcgcca ggagagaact gaggcgcctt ctagcagttg tgacgccaaa atcacgtctc
1741   cggagacccg cgcctccgc cagccgggcg caccctcgcc ggtagccttc tttgtgcgcc
1801   gtccggactc ccagctcccg gccggcagc cgagcccag cacaaagcag tcggaccgcg
1861   ccgcccgcct cccctctcgc gtctccgcct cggtttccca actctgcgcc gtcgggccgc
1921   ggcaggatga ttgcctcgca tctgcttgcc tacttcttca cggagctcaa ccatgaccaa
1981   gtgcagaagg ttgaccagta tctctaccac atgcgcctct ctgatgagac cctcttggag
2041   atctctaagc ggttccgcaa ggagatggag aaagggcttg agccaccac tcaccctact
2101   gcagcagtga agatgctgcc cacctttgtg aggtccactc agatgggac agaacacgga
2161   gagttcctgg ctctggatct tggagggacc aacttccgtg tgctttgggt gaaagtaacg
2221   gacaatgggc tccagaaggt ggagatggag aatcagatct atgccatccc tgaggacatc
2281   atgcgaggca gtggcaccca gctgtttgac cacattgccg aatgcctggc taacttcatg
2341   gataagctac aaatcaaaga caagaagctc ccactgggtt ttaccttctc gttccctgc
2401   caccagacta aactagacga gagtttcctg gtctcatgga ccaagggatt caagtccagt
2461   ggagtggaag gcagagacgt tgtggctctg atccggaagg ccatccagag gagaggggac
2521   tttgatatcg acattgtggc tgtggtgaat gacacagttg gaccatgat gacctgtggt
2581   tatgatgacc acaactgtga gattggtctc attgtgggca cgggcagcaa cgcctgctac
2641   atggaagaga tgcgccacat cgacatggtg gaaggcgatg aggggcggat gtgtatcaat
2701   atggagtggg gggccttcgg ggacgatggc tcgctcaacg acattcgcac tgagtttgac
2761   caggagattg acatgggctc actgaacccg ggaaagcaac tgtttgagaa gatgatcagt
2821   gggatgtaca tgggggagct ggtgaggctt atcctggtga agatggccaa ggaggagctg
2881   ctctttgggg gaagctcag cccagagctt ctcaacaccg tcgctttga gaccaaagac
2941   atctcagaca ttgaaggga aaggatggc atccggaagg cccgtgaggt cctgatgcgg
3001   ttgggcctgg acccgactca ggaggactgc gtggccactc accggatctg ccagatcgtg
3061   tccacacgct ccgccagcct gtgcgcagcc accctggccg ccgtgctgca gcgcatcaag
3121   gagaacaaag gcgaggagcg gctgcgctct actattgggg tcgacggttc cgtctacaag
3181   aaacaccccc attttgccaa gcgtctacat aagaccgtgc ggcggctggt gccggctgc
3241   gatgtccgct tcctccgctc cgaggatggc agtggcaaag gtgcagccat ggtgacagca
3301   gtggcttacc ggctggccga tcaacaccgt gcccgccaga agacattaga gcatctgcag
3361   ctgagccatg accagctgct ggaggtcaag aggaggatga aggtagaaat ggagcgaggt
```

```
3421  ctgagcaagg agactcatgc cagtgccccc gtcaagatgc tgcccaccta cgtgtgtgct
3481  accccggacg gcacagagaa aggggacttc ttggccttgg accttggagg aacaaatttc
3541  cgggtcctgc tggtccgtgt tcggaatggg aagtggggtg gagtggagat gcacaacaag
3601  atctacgcca tcccgcagga ggtcatgcac ggcaccgggg acgagctctt tgaccacatt
3661  gtccagtgca tcgcggactt cctcgagtac atgggcatga agggcgtgtc cctgcctctg
3721  ggttttacct tctccttccc ctgccagcag aacagcctgg acgagagcat cctcctcaag
3781  tggacaaaag gcttcaaggc atctggctgc gagggcgagg acgtggtgac cctgctgaag
3841  gaagcgatcc accggcgaga ggagtttgac ctggatgtgg ttgctgtggt gaacgacaca
3901  gtcggaacta tgatgacctg tggctttgaa gaccctcact gtgaagttgg cctcattgtt
3961  ggcacgggca gcaatgcctg ctacatggag gagatgcgca acgtggaact ggtggaagga
4021  gaagaggggc ggatgtgtgt gaacatggaa tgggggggcct tcggggacaa tggatgccta
4081  gatgacttcc gcacagaatt tgatgtggct gtggatgagc tttcactcaa ccccggcaag
4141  cagaggttcg agaaaatgat cagtggaatg tacctgggtg agattgtccg taacattctc
4201  atcgatttca ccaagcgtgg actactcttc cgaggccgca tctcagagcg gctcaagaca
4261  aggggcatct ttgaaaccaa gttcttgtct cagattgaga gtgactgcct ggccctgctg
4321  caagtccgag ccatcctgca acacttaggg cttgagagca cctgtgacga cagcatcatt
4381  gttaaggagg tgtgcactgt ggtggcccgg cgggcagccc agctctgtgg cgcaggcatg
4441  gccgctgtgg tggacaggat acgagaaaac cgtgggctgg acgctctcaa agtgacagtg
4501  ggtgtggatg ggaccctcta caagctacat cctcactttg ccaaagtcat gcatgagaca
4561  gtgaaggacc tggctccgaa atgtgatgtg tctttcctgc agtcagagga tggcagcggg
4621  aagggggcgg cgctcatcac tgctgtggcc tgccgcatcc gtgaggctgg acagcgatag
4681  aacccctgaa atcggaaggg acttcctctt tctctccttc ttccctgttt taaattataa
4741  gatgtcatcc ccttgtgtca gagacagacc ccttggcttt tgcttggcag agaggacccc
4801  actgactggg gttttgtctc tgcatctcat tgtagagctt ggtggctgag cttggcccta
4861  ttaagataaa tagagttcca aataaggatt tgttcacatg catcataacc attcccattg
4921  gttctcctaa aacatgaaaa ttatctccct tagtaatccc ccttgccaaa ttccatgtcc
4981  ctgtataatt ctacaggatg gggacactaa tgaagatacg gttgcttcac cttggagcct
5041  gaacatgaca tttctaagtg gggtgcatcc cccagcactg atgttgttac tgattctcct
5101  gtcagagatc tgggaggtct ccactgagga tgtgagcctg attatcctat aggcagacgt
5161  ggggagggtg gagggggtgac agtggaggaa atccatggat atccacgca gcagcccctc
5221  tttaacctca tctacaagca tttgccctgt ggattccagc atttgccatt cctggaatca
5281  aggaatcctg agtctgggca atgaaaccaa agccaggagt tgacgcatcc tgcagttggg
5341  ccagctgtcg catctcagcg gggcgcacat gttatccaca agcaatggac cttttgggaa
5401  gggggagttt ttagtttgtt ttacaaattt ttcctgcaaa agtggaatca ctgtattttc
5461  attttaattt atatttgaaa ttttatttag ttcttgagta gatctgcttc ttcatcttga
5521  catgtaatga atggtcagtt gtacgtaatg tatttatatg ttaatttgtt atgtatatag
5581  atgtgcaagt cttgtcagaa ttggcctcag tgtagttaaa gggcagaagg ggaagatact
5641  gactagtcat agaaatacct cattcgcctg tgggaagaga agggaagcct cttcagggtg
5701  agtgaatggc aaagcggttg cttctggctc ctccttcccc tgtggtcttg gaagtgtgtg
5761  gaaggcaggg acagagatgg aggccgagcc aatagactga agagaccaca gcaattggct
```

```
                            -continued
5821   cctccatcta gagattttct tggcagtatt ccatgggatg ttaagcaaag gaaaccaaag 5881   gaatcgtttc aaatggactc atggcttaga aatctttatt cttagggcag tcagtagtat 5941   tctaaagctt tctgacaaga taaaggaagt caccaaaatt tcttttttta aattgtatct 6001   aatcctcaac aacaaaccaa aacagaacaa ttaaacagcc aaataaaacc tcagggacaa 6061   cattttggt  gtatttgagc cctcccagca agtttcacct tgggtttgta ttttaaatgt 6121   tttacaagaa ttgtccatgt gcttccctag gctgagctgg cattggtctg ctgacctgtt 6181   tttgtgtttt tcttttttt  atacacaaca tttatttcaa actattggga gggatgagag 6241   tggcttaaaa acttccatcc ctactttca  agagtgcagt tgattctgaa tctgaaagcc 6301   cgcctctgtc ctaaaataca aacaagcaca gacattaaac ctggatacta tatgataaag 6361   agggatgtaa ctattgaatt ggatacaagg atcagaatgg aaagaaactc acgatgaaat 6421   tgaacctggt ttttgtatat ttatcaaact tgtgctgaga atagtgtctg attatacgac 6481   ttttaagcaa agttgggtgt aattaggtga aaacagccca ggtcctcccg ggagcacaga 6541   ggggctaggg gctggtcctt ctcgtttgct ctagtcttgc tttgctgtct ggtgtagctc 6601   ctctgctgct cccatctgca ctaattgacc caaaacgtgg gtatttcctg ctacacaaaa 6661   gccaaaaggt ttcatgtaga ttttagttca ctaaagggtg cccacaaaat agagattaat 6721   tttaacttaa attttaagct tgaagattag gtactatctg tgaagttaca ctttttttt 6781   ttttttaaa  ggtagagatg tgtgtgtgtg taggtattaa agatgtgttg ttggtttcca 6841   aaaaggaaca ctggaaaata aattttgaat gtttatgttc tcagaatcag gttgacagtc 6901   ccttgctgac atggctttgc tttgtgtaaa tacagtggat ctcaatcttc ggggtgtgat 6961   gaatagcgaa tcatctcaaa tccttgagca ctcagtctag tgaagatgtt gtcattatgt 7021   acaatacata actagtttaa ttaactatgt gatgttaact attattaata aattttaaca 7081   ttttccaaaa taaaaaaaaa aaaaaaaa
```

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "expression" as used herein is defined as the transcription and/or translation of a particular nucleotide sequence driven by its promoter.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. The preparation can be at least 75%, at least 90%, and at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any polypeptide or polynucleotide having an alteration in expression level, sequence, or activity that is associated with a disease or disorder or risk of disease or disorder.

As used herein, "obtaining" as in "obtaining an agent" includes synthesizing, purchasing, or otherwise acquiring the agent.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

As used herein, "polynucleotide" includes cDNA, RNA, DNA/RNA hybrid, antisense RNA, siRNA, miRNA, snoRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, the term "promoter" or "regulatory sequence" means a nucleic acid sequence which is required for expression of a gene product operably linked to the promoter or regulator sequence. In some instances, this sequence may be the core promoter sequence and in other instances, this sequence may also include an enhancer sequence and other regulatory elements which are required for expression of the gene product. The promoter or regulatory sequence may, for example, be one which expresses the gene product in an inducible manner.

By "reduces" is meant a negative alteration of at least 10%, 25%, 50%, 75%, or 100%.

By "reference" is meant a standard or control condition. In some embodiments, the reference is an activity or level of a FGF signaling polypeptide or polynucleotide; or HK2 polypeptide or polynucleotide in a healthy; or c-myc polypeptide or polynucleotide, normal subject or in a subject that does not have excessive vascular development. In some embodiments, the FGF signaling polypeptide is FGF2. In some other embodiments, the HK2 is a human HK2.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, or at least about 25 amino acids. The length of the reference polypeptide sequence can be about 35 amino acids, about 50 amino acids, or about 100 amino acids. For nucleic acids, the length of the reference nucleic acid sequence will generally be at least about 50 nucleotides, at least about 60 nucleotides, or at least about 75 nucleotides. The length of the reference nucleic acid sequence can be about 100 nucleotides, about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant an agent that recognizes and binds a polypeptide or polynucleotide of the invention, but which does not substantially recognize and bind other molecules in a sample, for example, a biological sample, which naturally includes a polynucleotide of the invention. In some embodiments, the agent is a nucleic acid molecule.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions will ordinarily include temperatures of at least about 30° C., at least about 37° C., and at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 µg/ml denatured salmon sperm DNA (ssDNA). In yet another embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will be less than about 30 mM NaCl and 3 mM trisodium citrate, or less than about 15 mM NaCl and 1.5 mM trisodium citrate. Stringent temperature conditions for the wash steps will ordinarily include a temperature of at least about 25° C., at least about 42° C., and at least about 68° C. In one embodiment, wash steps will occur at 25° C. in 30 mM NaCl, 3 mM trisodium citrate, and 0.1% SDS. In another embodiment, wash steps will occur at 42° C. in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence is at least 60%, at least 80%, at least 85%, at least 90%, at least 95% or even at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the term "rapamycin" refers to a compound (a macrocyclic triene antibiotic also known as Sirolimus) produced by the bacterium Streptomyces hygroscopicus. It inhibits the activation of T cells and B cells by reducing the production of interleukin-2 (IL-2). Rapamycin has immunosuppressant functions in humans and is especially useful in medicine for preventing organ transplant rejection such as the rejection of kidney transplants. It is also used to treat lymphangioleiomyomatosis, a lung progressive and systemic disease. Rapamycin has also been shown to inhibit proliferation of vascular smooth muscle cells migration (Poon M. et al., J Clin Invest. 1996; 98(10):2277-83). Rapamycin derivatives used according to the methods of present invention include, but are not limited to, 40-0-alkyl-rapamycin derivatives, e.g. 40-O-hydroxyalkyl-rapamycin derivatives, for example 40-O-(2-hydroxy)-ethyl-rapamycin (everolimus), rapamycin derivatives which are substituted in 40 position by heterocyclyl, e.g. 40-epi-(tetrazolyi)-rapamycin (also known as ABT578), 32-deoxo-rapamycin derivatives and 32-hydroxy-rapamycin derivatives, such as 32-deoxorapamycin, 16-O-substituted rapamycin derivatives such as 16-pent-2-ynyloxy-32-deoxorapamycin, 16-pent-2-ynyloxy-32(S or R)-dihydro-rapamycin, or 16-pent-2-ynyloxy-32(S or R)-dihydro-40-O-(2-hydroxyethyl)-rapamycin, rapamycin derivatives which are acylated at the oxygen in position 40, e.g. 40-[3-hydroxy-2-(hydroxy-methyl)-2-methylpropanoate]-rapamycin (also known as CCI779 or temsirolimus), rapamycin derivatives as disclosed in WO9802441 or WO0114387 (also sometimes designated as rapalogs), e.g. including AP23573, such as 40-O-dimethyl-phosphinyl-rapamycin, compounds disclosed under the name biolimus (biolimus A9), including 40-O-(2-ethoxy) ethyl-rapamycin, and compounds disclosed under the name TAFA-93, AP23464, AP23675 or AP23841; or rapamycin derivatives as e.g. disclosed in WO2004101583, WO9205179, WO9402136, WO9402385 and WO9613273.

By "subject" is meant a mammal, including, but not limited to, a human or non-human mammal, such as a bovine, equine, canine, ovine, murine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Detailed Description

Methods of Treatment and Therapeutic Strategy for Reducing Vascular Development

Described herein are studies highlighting that fibroblast growth factor receptor (FGFR) signaling is a critical regulator of vascular development. This is achieved by FGF-dependent control of c-Myc (Myc) expression that, in turn, regulates expression of the glycolytic enzyme hexokinase 2 (HK2).

Provided herein are compositions and methods to reduce excessive vascular development and treat related disorders by inhibiting or decreasing HK2 gene expression or HK2 polypeptide activity. In some embodiments, the vascular development comprises angiogenesis and lymphangiogenesis.

Described herein is a key mechanism responsible for vasculature progression and studies demonstrating that modulating this pathway fundamentally changes vascular development. The mechanism involves FGF-dependent control of c-Myc (Myc) expression that, in turn, regulates expression of the glycolytic enzyme hexokinase 2 (HK2). Targeting this mechanism can dramatically alter the management of angiogenesis or lymphangiogenesis and represents a major practical innovation in many disorders comprising angiogenesis or lymphangiogenesis. Angiogenesis is known to be implicated in the pathogenesis of a variety of disorders such as, but not limited to, solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Lymphangiogenesis is also known to occur in some disorders or conditions involving tissues inflammation, wound healing, and tumor metastasis.

The therapeutic approach described herein, based on results derived from cell signaling studies and confirmed by rigorous in vivo mouse genetics studies, is fundamentally new.

In one aspect, the invention provides a method for treating excessive vascular development in a subject in need thereof. The method of the invention comprises administering to the subject an effective amount of an agent that decreases the level of expression and/or activity of hexokinase 2 (HK2) thereby decreasing the level of expression and/or activity of at least one selected from the group consisting of a fibroblast growth factor receptor (FGFR), a FGF ligand and FGF signaling, and treating the excessive vascular development in the subject, wherein the HK2 depleting agent targets an endothelial cell in the subject.

In another aspect, the invention provides a method for reducing or inhibiting vascular development in a subject in need thereof by administering to the subject an effective amount of an HK2 depleting agent in a pharmaceutical acceptable carrier, wherein the HK2 depleting agent targets an endothelial cell in the subject.

In some embodiments, the present invention provides a method for treating, reducing or inhibiting a vascular development related to an angiogenesis or a lymphangiogenesis. In certain embodiments, the vascular development is pathological angiogenesis associated with ischaemic and inflammatory diseases, a cardiovascular disease. In some embodiments, the present invention provides a method for treating atherosclerosis and/or disorders or symptoms thereof which comprise administering a therapeutically effective amount of a pharmaceutical composition comprising an agent that modulates the activity or level of an HK2 polypeptide or FGF signaling polypeptide in a cell of a subject (e.g., a mammal such as a human). In other embodiments, the agent is a HK2 depleting agent.

In some embodiments, the present invention provides a method for treating, reducing or inhibiting a vascular development is a tumor angiogenesis or lymphangiogenesis associated with cancer. The method comprises administering to the subject an effective amount of an HK2 depleting agent, wherein the HK2 depleting agent targets an endothelial cell in the subject. In further embodiments, the cancer is a brain cancer, a colorectal cancer, a pancreatic cancer, a gastric cancer, an intestinal cancer, a renal cancer, a hepatic cancer, a lung cancer or an esophageal cancer. In still further embodiments, the cancer is metastatic.

In some embodiments, the HK2 depleting agent is selected from the group consisting of an antisense RNA, an inhibitor of HK2 enzymatic activity, siRNA, shRNA, miRNA, a CRISPR system, a ribozyme, an antisense molecule, an aptamer, a peptidomimetic, a small molecule, a nanoparticle and any combination thereof. In certain embodiments, the agent is a HK2 siRNA. In certain embodiments, the HK2 inhibitor is a kinase inhibitor.

In other embodiments, the HK2 depleting agent is a HK2 antibody. In certain embodiments, the antibody comprises a polyclonal antibody, a monoclonal antibody, a humanized antibody, a synthetic antibody, a heavy chain antibody, a human antibody, a biologically active fragment of an antibody, an antibody mimic and any combination thereof.

In certain embodiments, the agent that decreases the activity or level of a FGF signaling polypeptide in a cell is an inhibitory polynucleotide that reduces expression of a FGF signaling polypeptide. Further details regarding delivery of inhibitory nucleic acids are presented in the Nucleic acids delivery section, below.

In some embodiments, FGF expression and/or activity is decreased by delivering an agent such as an HK2 depleting agent that targets an endothelial cell in the subject. The decrease in the level of expression and/or activity of FGF consequently decreases the signaling activity of a fibroblast growth factor receptor (FGFR) and reduces endothelial migration, sprouting and proliferation. In some embodiments, FGFR, FGF ligand and/or FGF signaling is/are reduced or inhibited by delivering a HK2 depleting agent that targets an endothelial cell in the subject. In other embodiments, the FGFR comprises FGFR1 and/or FGFR3.

In a particular embodiment, the cell is an endothelial cell. It is well established in the art that endothelial cells are a type of epithelial cells that line the interior surface of blood vessels and lymphatic vessels, forming an interface between circulating blood or lymph in the lumen and the rest of the vessel wall. In one embodiment, the endothelial cell is a blood endothelial cell. In another embodiment, the endothelial cell is a lymphatic endothelial cell.

Without intending to be bound by theory, it is believed that a combination of these strategies, aimed at reducing HK2 in endothelial cells, provides a therapeutic approach for treatment of angiogenesis and/or lymphangiogenesis.

In particular embodiments, the HK2 depleting agent modulates the activity or level of a FGF polypeptide, by decreasing the activity or level of FGF polypeptide in a cell. In some embodiments, the HK2 depleting agent is an inhibitory polynucleotide that reduces the expression of FGF or modulates the activity or level of an FGF polynucleotide.

In some instance, a decrease in gene expression and/or activity of HK2, FGF or FGF receptor (FGFR) is desired. This can be achieved by various well-established molecular techniques known in the art such as, but not limited to, micro-RNA (e.g. miRNA sponge, Ebert et al. RNA. 2010 November; 16(11): 2043-2050), RNA interference (RNAi), small inhibitor RNA (siRNA), small hairpin RNA (shRNA) and Clustered Regularly Interspaced Short Palindromic Repeats (CRISPRs).

In some embodiments, the HK2 depleting agent of this invention is selected from the group consisting of an antisense RNA, an inhibitor of HK2 enzymatic activity, siRNA, shRNA, miRNA, a CRISPR system, a ribozyme, an antisense molecule, an aptamer, a peptidomimetic, a small molecule, a nanoparticle and any combination thereof. In certain embodiments, the agent is a HK2 siRNA. In certain embodiments, the HK2 inhibitor is a kinase inhibitor.

In other embodiments, the HK2 depleting agent is a HK2 antibody. In certain embodiments, the antibody comprises a polyclonal antibody, a monoclonal antibody, a humanized antibody, a synthetic antibody, a heavy chain antibody, a human antibody, a biologically active fragment of an antibody, an antibody mimic and any combination thereof.

In certain embodiments, the agent that decreases the activity or level of a FGF signaling polypeptide in a cell is an inhibitory polynucleotide that reduces expression of a FGF signaling polypeptide.

In some aspects of the invention, the subject to be treated is pre-selected. The subject is pre-selected when an alteration (increase or decrease) in the activity or level of activity or level of a HK2 polypeptide or FGF signaling polypeptide or polynucleotide in a sample from the subject is detected. In some embodiments, the subject is pre-selected when an increase in the activity or level of a HK2 polypeptide or polynucleotide or FGF signaling polypeptide or polynucleotide, is observed relative to a reference level. In other embodiments, the pre-selected subject is identified as having or being at risk for developing an excessive vascular growth. The method comprises administering to the subject an effective amount of an HK2 depleting agent (e.g., an agent that modulates the activity or level of an FGF signaling polypeptide) that targets an endothelial cell in the subject and that is sufficient to treat the disease or disorder or symptom thereof.

In one aspect, the invention includes a method for diagnosing excessive vascular development or a predisposition for developing excessive vascular development in a subject in need thereof. The method comprises measuring in an endothelial cell in the subject the level or activity of a marker comprising a HK2 polypeptide or polynucleotide and comparing it to a control, wherein an increase in the level or activity of the marker is indicative of an excessive vascular development or a predisposition for developing excessive vascular development in the subject, and recommending a treatment to the subject. In some embodiments, the marker further comprises an FGF signaling polypeptide or polynucleotide.

In some aspects of the invention, the subject in need thereof is administered an additional chemotherapeutic agent, an anti-cell proliferation agent, an immunotherapeutic agent and any combination thereof. In some embodiments, the HK2 depleting agent and the additional agent are co-administered to the subject.

The methods disclosed herein include administering to a subject in need thereof an effective amount of an agent described herein, or a composition described herein to produce such effect. Identifying a subject in need of such treatment can be made by a health care professional and may be subjective (e.g. opinion) or objective (e.g. measurable by a test or diagnostic method, such as using the methods described herein).

The therapeutic methods of the invention also include prophylactic treatment which comprises administering a therapeutically effective amount of one or more of the agents described herein (such as a HK2 depleting agent that modulates the activity or level of a FGF signaling polypeptide) to a subject, particularly a human. Such treatment is suitable for mammals, particularly humans, suffering from, having, susceptible to, or at risk for an excessive vascular development disorder, an atherosclerosis, disorder, or symptom thereof. In one embodiment, the invention provides a method for measuring the efficacy or monitoring the progression of a treatment for excessive vascular development in a subject in need thereof. The method comprises determining a level or activity of diagnostic marker (e.g., an FGF signaling polypeptide or polynucleotide, or HK2 polypeptide or polynucleotide) in a subject in need thereof. In some embodiments, the activity or level of the diagnostic marker is determined and compared to a known activity or level of a FGF signaling polypeptide or polynucleotide, or HK2 polypeptide or polynucleotide in either healthy normal controls, or in other afflicted patients, to establish the subject's disease status. In some embodiments, an activity or level of a FGF signaling polypeptide or polynucleotide, or HK2 polypeptide or polynucleotide is determined in an endothelial cell from the subject. In some embodiments, a second activity or level of a FGF signaling polypeptide or polynucleotide, or HK2 polypeptide or polynucleotide in the subject is determined at a time point later than the determination of the first level, and the two levels are compared to monitor the course of disease or the efficacy of the therapy. In certain embodiments, the level of a FGF signaling polypeptide or polynucleotide, or HK2 polypeptide or polynucleotide is determined prior to commencing. This level can then be compared to the level of a FGF signaling polypeptide or polynucleotide, or HK2 polypeptide or polynucleotide in the subject after the treatment commences, to determine the progress or efficacy of the treatment.

Additional Treatment Methods

In another aspect, the invention includes a method of rescuing a defect or an insufficient vascular development and treating related disorders a subject in need thereof. The method comprises increasing HK2 gene expression or HK2 polypeptide activity by administering to the subject an HK2 increasing agent.

In some embodiments, the HK2 increasing agent is an adenovirus encoding HK2.

In some embodiments, the HK2 increasing agent rescues vascular defects when FGF signaling is reduced and/or when FGFR expression or activity is abnormal.

In other embodiments, the disorders treated by the method of this invention are disorders associated with endothelial-to-mesenchymal transition such as, but not limited to, atherosclerosis.

Pharmaceutical Compositions

The present invention features a composition useful for treating or reducing angiogenesis or lymphangiogenesis in a subject in need thereof. The composition includes an agent that modulates the activity or level of a FGF signaling polypeptide or polynucleotide, or HK2 polypeptide or polynucleotide in the subject.

Specifically the composition is a pharmaceutical composition that comprises a HK2 depleting agent and a pharmaceutically acceptable carrier.

In some embodiments, the HK2 depleting agent is selected from the group consisting of an antisense RNA, an inhibitor of HK2 enzymatic activity, siRNA, shRNA, miRNA, a CRISPR system, a ribozyme, an antisense molecule, an aptamer, a peptidomimetic, a small molecule, a nanoparticle and any combination thereof. In certain embodiments, the agent is a HK2 siRNA. In certain embodiments, the HK2 inhibitor is a kinase inhibitor.

In other embodiments, the HK2 depleting agent is a HK2 antibody. In certain embodiments, the antibody comprises a polyclonal antibody, a monoclonal antibody, a humanized antibody, a synthetic antibody, a heavy chain antibody, a human antibody, a biologically active fragment of an antibody, an antibody mimic and any combination thereof.

In certain embodiments, the agent that decreases the activity or level of a FGF signaling polypeptide in a cell is an inhibitory polynucleotide that reduces expression of a FGF signaling polypeptide.

In some embodiments, the HK2 depleting agent suppresses or decreases the expression human HK2 polynucleotide or the activity of human HK2 polypeptide. In other embodiments the HK2 depleting agent is an HK2 siRNA. In some embodiments the HK2 depleting agent is formulated for selective delivery to an endothelial cell of the subject in need thereof.

Nucleic Acids Delivery

When the HK2 depleting agent is a nucleic acid, delivery may be accomplished as described herein. Introduction of nucleic acids into cells (e.g. endothelial cells) may be accomplished using any number of methods available in the art. For example, transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, an inhibitory nucleic acid or siRNA as described can be cloned into a retroviral vector where expression can be driven from its endogenous promoter, from the retroviral long terminal repeat, or from a promoter specific for a target cell type of interest. In some embodiments, the target cell type of interest is an endothelial cell. Other viral vectors that can be used to introduce nucleic acids into cells include, but are not limited to, vaccinia virus, bovine papilloma virus, or herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). In some embodiments, a viral vector is used to administer a polynucleotide encoding inhibitory nucleic acid molecules that inhibit expression of HK2.

Non-viral approaches can also be employed for the introduction of the therapeutic to a cell of a patient requiring treatment for excessive vascular growth. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). In some embodiments, the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of polynucleotide encoding inhibitory nucleic acid molecules into the affected tissues of a patient can also be accomplished by transferring a polynucleotide encoding the inhibitory nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothione in promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

In some other embodiments, the therapeutic polynucleotide (i.e. HK2 depleting agent) is expressed in an endothelial cell using a lentiviral vector. In still other embodiments, the therapeutic polynucleotide is administered intravenously. In some embodiments, the therapeutic polynucleotide contains one or more chemical modifications that reduce immunostimulation, enhance serum stability, increase specificity, and/or improve activity, while still retaining silencing activity. Such chemical modifications are described in, for example, Foster et al., RNA. 2012 March; 18(3): 557-568. In some embodiments, the therapeutic polynucleotide contains one or more chemical modifications to prevent degradation, as described in Chen et al., Cell Reports 2012; 2(6)1684-1696.

In a particular embodiment, the therapeutic polynucleotide is selectively delivered to endothelial cells using nanoparticles formulated for selective targeting to endothelial cells, such as a 7C1 nanoparticle. Selective targeting or expression of polynucleotides to an endothelial cell is described in, for example, Dahlman et al., Nat Nanotechnol. 2014 August; 9(8): 648-655.

In some other embodiments, the therapeutic polynucleotide is selectively targeted to a smooth muscle cell. The therapeutic polynucleotide can be selectively delivered to a smooth muscle cell using tissue factor-targeted nanoparticles that can penetrate and bind stretch-activated vascular smooth muscles as described in Lanza et al., Circulation. 2002 Nov. 26; 106(22):2842-7.

Other Formulations for Delivery

The pharmaceutical composition of the present invention may be administered systemically, for example, formulated in a pharmaceutically-acceptable buffer such as physiological saline. In some embodiments, the route of administration includes, for example, subcutaneous, intravenous, interperitoneally, intramuscular, or intradermal injections that provide continuous, sustained levels of the agent in the patient. In other embodiments, the route of administration is selected from the group consisting of inhalation, oral, rectal, vaginal, parenteral, topical, transdermal, pulmonary, intranasal, buccal, ophthalmic, intrathecal, and any combination thereof.

The amount of the therapeutic agent to be administered varies depending upon the manner of administration, the age and body weight of the patient, and with the clinical symptoms. Generally, amounts will be in the range of those used for other agents used in the treatment of excessive vascular development (e.g. angiogenesis), although in certain instances lower amounts will be needed because of the increased specificity of the agent. A composition is administered at a dosage that decreases effects or symptoms of angiogenesis or lymphangiogenesis as determined by a method known to one skilled in the art.

The therapeutic agent may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (saw tooth kinetic pattern); (iv) formulations that localize action by, e.g., spatial placement of a controlled release composition adjacent to or in contact with an organ, such as the heart; (v) formulations that allow for convenient dosing, such that doses are administered, for example, once every one or two weeks; and (vi) formulations that target atherosclerosis using carriers or chemical derivatives to deliver the therapeutic agent to a particular cell type (e.g., endothelial cells). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the agent in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The pharmaceutical composition of this invention could be coated or comprised in a drug-eluting stent (DES) ((Nikam et al., 2014 Med Devices 7:165-78)) that releases at a given site (such as an artery) and pace (i.e. slow release) the composition of this invention.

The formulation and preparation of such compositions are well known to those skilled in the art of pharmaceutical formulation. Formulations can be found in Remington: The Science and Practice of Pharmacy ((20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Compositions for parenteral use may be provided in unit dosage forms (e.g., in single-dose ampoules), or in vials containing several doses and in which a suitable preservative may be added. The composition may be in the form of a solution, a suspension, an emulsion, an infusion device, or a delivery device for implantation, or it may be presented as a dry powder to be reconstituted with water or another suitable vehicle before use. Apart from the active agent that reduces vascular development, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

In some embodiments, the composition of this invention is delivered locally from, but not limited to, the strut of a stent, a stent graft, a stent cover or a stent sheath. In other embodiments, the invention comprises a local delivery of the composition into a tumor, an artery, a vessel or any desired tissue or region of interest.

In some embodiments, the composition comprising the active therapeutic is formulated for intravenous delivery. As indicated above, the pharmaceutical compositions according to the invention may be in the form suitable for sterile injection. To prepare such a composition, the suitable therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Kits

The invention provides kits that includes a diagnostic composition comprising a capture reagent for measuring relative expression level or activity a FGF signaling polypeptide or polynucleotide, or HK2 polypeptide or polynucleotide (e.g., a primer or hybridization probe specifically binding to a FGF signaling polypeptide or polynucleotide, or HK2 polypeptide or polynucleotide).

In General

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Results of experiments described herein were obtained using the following materials and methods.

Materials and Methods

Genetically Engineered Mouse Models.

For inducible Cre-mediated recombination, FGFRf1$^{flox/flox}$; FGFR3$^{+/-}$ mice (mixed background), HK2$^{flox/flox}$ mice (C57BL/6 background), and Myc$^{flox/flox}$ mice (C57BL/6 background) were bred with Cdh5-CreER$^{T2}$ (C57BL/6 background), Prox1-CreER$^{T2(BAC)}$ (mixed background) and Prox1-CreER$^{T2(KI)}$ (mixed background). mTmG reporter mice (C57BL/6 background) were bred with different Cre lines to assess the recombination efficiency in lymphatics. All mouse protocols and experimental procedures were approved by the IACUC (Yale University School of Medicine).

Cell Culture and Treatment.

Human dermal lymphatic endothelial cells (HDLECs, HMVEC-dLyNeo-Der Lym Endo EGM-2MV) and Pooled human umbilical vein endothelial cells (HUVECs) were purchased from Lonza and cultured in EBM2 basal medium with EGM-2 MV BulletKit. Both cell types were tested negative for mycoplasma in Lonza. Culture medium was changed every the other day. Tissue culture plates were coated with 0.1% gelatin (Sigma) for 30 min at 37° C. and washed with Dulbecco's Phosphate-Buffered Saline (Life Technologies) before cell plating. For siRNA-mediated gene knockdown, FGFR1 siRNA (ON-TARGETplus human FGFR1 siRNA, Dharmacon; Hs_FGFR1_6, Qiagen), FGFR3 siRNA (Hs_FGFR3_6, Qiagen), HK2 siRNA (s6562 human HK2 siRNA, Life Technologies), c-Myc siRNA (ON-TARGETplus human Myc siRNA, Dharmacon), All-Star negative control siRNA (Qiagen), and ON-TARGETplus Non-targeting pool (Dharmacon) were transfected by lipofectamine RNAimax reagent (Life Technologies). Human FGF2 was provided by Kaken Pharmaceutical Co, Ltd (Japan) and ordered from Peprotech. Human VEGFC, VEGFD, IGF1, IGF2 and PDGFBB were purchased from Peprotech. To assay the effect of FGFR1 knockdown on glycolytic enzyme expression, HDLECs, transfected with control or FGFR1 siRNA 3 days in advance, were replated and collected for protein analysis 24 hr later when the cell confluency reached ~80%. To examine the growth factor stimulation of glycolytic enzymes, freshly plated HDLECs were starved overnight with EBM2 plus 0.1% FBS and then stimulated with FGF2 (50 ng/ml or 100 ng/ml), VEGFC (100 ng/ml), VEGFD (100 ng/ml), IGF1 (100 ng/ml), IGF2 (100 ng/ml) and PDGFBB (100 ng/ml) before lysis in RIPA buffer for protein extraction. For Western blot analysis the following antibodies were used: HK1 (Cell Signaling Technology, #2024), HK2 (Cell Signaling Technology, #2867), PFKFB3 (Proteintech, #13763-1-AP), PFKP (Cell Signaling Technology, #12746), PKM2 (Cell Signaling Technology, 4053), c-MYC (Cell Signaling Technology, #9402; Abcam, #ab32072), FGFR1 (Cell Signaling Technology, #9740), 3-actin (Sigma, #A5316), and Tubulin (Cell Signaling Technology, #2148). ImageJ was used for densitometry quantification of western blot bands.

RNA Sequencing (RNA-Seq) Experimental Design and Sample Preparation.

HDLECs treated with or without FGF2 for 14 hr were lyzed for RNA extraction and were eventually used to generate a list of differentially expressed genes between FGF2 and control, named "gain-of-FGF signaling" dataset. Similarly, HDLECs treated with FGFR1 siRNA or negative control siRNA for 3 days were lyzed for RNA extraction and were finally used to generate a list of differentially expressed genes between FGFR1 siRNA and negative control siRNA, so called "loss-of-FGF signaling" dataset. For each treatment, 9 biological replicates prepared from 3 independent experiments were analyzed. RNA isolation was carried out using RNeasy Mini Kit (Qiagen).

RNA-Seq.

Extracted total RNA was quantitated by NanoDrop and RIN value was measured with an Agilent Bioanalyzer. 1 µg of qualified RNA (RIN>8.0) was used as input for library construction following the Illumina TruSeq RNA Sample Preparation protocol. RNA libraries were sequenced on an Illumina HiSeqX platform, PE 2×150 bp. The average data yield for each sample was 20M PE reads with % of Q30 bases>90.

RNA-Seq Data Analysis.

RNA-seq reads from each sample were aligned to human genome (build 38) using short reads aligner STAR (version 2.5.1b). Gene expression quantification was then performed using RSEM with GENCODE annotation (release 24: gencodegenes.org). Differential analysis was performed using edgeR to identify genes with significant expression changes between groups. Genes observed to change significantly (FDR<$1\times10^{-2}$) in their expression in both "gain-of-FGF signaling" dataset and "loss-of-FGF signaling" dataset were first identified (1999 genes). If a gene is truly regulated by FGF signaling, it should show opposite changing direction between "gain-of-FGF signaling" dataset and "loss-of-FGF signaling" dataset. Therefore, next-step analysis was focused on the 929 genes whose expression upregulated by FGF2 treatment but decreased after FGFR1 knockdown, and the 828 genes whose expression reduced by FGF2 stimulation but increased after FGFR1 knockdown. Those 1757 genes were used for functional enrichment analysis by running GOseq, an algorithm that controls gene length bias in next-generation sequence data (Young, M. D. et al., Genome biology 11, R14, (2010)) nGOseq, a modified version of the nEASE algorithm (Chittenden, T. W. et al., Bioinformatics 28, 726-728, (2012)), which also controls for gene length bias was used to assess functional enrichment of nested GOseq terms. Briefly, each enriched upper-level GOseq term was used for nested GOseq (nGOseq) analysis to identify statistically enriched nested GO terms driving upper-level functional enrichment of non-specific GOseq terms. For FIG. 13G, the top 50 genes which were increased by FGF2 treatment (ranked in "gain-of-FGF signaling" dataset by fold change) and the top 50 genes which were reduced after FGFR1 knockdown (ranked in "loss-of-FGF signaling" dataset by fold change) were first identified. By comparing the two lists of top hits, an overlap containing 24 protein-coding transcripts were generated. Those 24 genes were further ranked by the sum of their absolute fold changes in "gain-of-FGF signaling" dataset and "loss-of-FGF signaling" dataset. After this ranking, top 20 genes were shown in FIG. 13G.

Measurement of Glycolysis, Glucose Oxidation, Glutamine Oxidation, Fatty Acid Oxidation and Glucose Uptake.

Glycolysis was measured as previously described. Briefly, subconfluent HDLECs cultured in 12-well plates were incubated with 1 ml/well EBM2 medium (containing appropriate amount of serum and supplement) with 80 µCi/mmol 5-$^3$H-glucose (Perkin Elmer) for 2-3 hr. Then 0.8 ml/well medium was transferred into glass vials with hanging wells and filter papers soaked with $H_2O$. After incubation in a cell culture incubator for at least 2 days to reach saturation, filter papers were taken out and the amount of evaporated $^3H_2O$ was measured in a scintillation counter. Glucose oxidation, glutamine oxidation and fatty acid oxidation were measured essentially as reported. For measurement of glucose uptake, HDLECs were incubated with 2-[1-$^{14}$C]-deoxy-D-glucose (2.5 µCi/ml, Perkin Elmer) for 10 min. before PBS washing (at least 3 times to get rid of all radioactive medium) and then lysis with 500 µL 0.1 N NaOH. 400 µl NaOH cell lysate for each sample was transferred to scintillation vials containing scintillation liquid and measured.

Mass Spectrometry Analysis of Metabolites.

HDLECs were quenched by a rapid wash with ice-cold PBS and then collected in 150 µl of an ice-cold solution containing 20% methanol, 0.1% formic acid, 1 mM phenylalanine, 3 mM NaF and 100 µM EDTA. $^2$H4-Taurine (10 µM, CDN Isotopes) was used as a loading control. All the samples were lyophilized and resuspended in 50 µL of water prior the LC-MS/MS analysis. Samples were injected onto a Cogent Diamond Hydride™ column (2.2 µm particle size, 2.1 mm×10 cm) at a flow rate of 0.5 mL/min. Glycolytic intermediates were eluted isocratically with a 95% aqueous/5% organic solvent mixture. The aqueous solution contained 15 mM ammonium formate. The organic solution contained 60% acetonitrile, 35% isopropyl alcohol and 15 mM ammonium formate. Samples were ionized by electrospray into an ABSCIEX 5500 QTRAP equipped with a SelexION for differential mobility separation (DMS) and acquired using multiple reaction monitoring (MRM) in negative mode, as described previously. DMS-based separation of fructose-6-phosphate from glucose-6-phosphate, as well as the separation of ATP, ADP and AMP nucleotides, was achieved using no modifier. Isopropyl alcohol was used as modifier for the DMS-based separation of the remaining glycolytic intermediates. Retention times were confirmed with known standards and peaks integrated using Multiquant (ABSCIEX) using the following MRM transition pairs ($Q_1/Q_3$): 506/159 for ATP, 426/79 for ADP, 346/79 for AMP, 259/97 for glucose-6-phosphate, 259/97 for fructose-6-phosphate, 339/97 for fructose-1,6-bisphosphate, 169/97 for dihydroxyacetone phosphate (DHAP), 185/79 for 3-phosphoglycerate (3PG), 185/79 for 2-phosphoglycerate (2PG), 167/79 for phosphoenolpyruvate (PEP), 89/89 for lactate and 124/80 for endogenous taurine. Endogenous taurine was used as internal control for cell density as previously described (Kibbey, R. G. et al., Cell metabolism 5, 253-264, (2007)).

Seahorse Assays.

Metabolic analyses in HDLECs were performed with the Seahorse XFe96 analyzer (Agilent Seahorse) according to the manufacturer's recommendations. In brief, siRNA-transfected or adenovirus-transduced HDLECs (40.000 cells per well of a 96-well plate) were seeded on fibronectin-coated XFe96 microplates. After 2 hr, cell culture medium was changed to a non-buffered assay medium and cells were maintained in a non-$CO_2$ incubator for 1 hr. The Glycolysis stress test kit (Agilent Seahorse) was used to monitor the extracellular acidification rate (ECAR) under various conditions. Three baseline recordings were made, followed by sequential injection of glucose (10 mM), the mitochondrial/ATP synthase inhibitor oligomycin (3 µM), and the glycolysis inhibitor 2-deoxy-D-glucose (2-DG; 100 mM). The Mito stress test kit (Agilent Seahorse) was used to assay the mitochondrial respiration rate under basal conditions, in the presence of the ATP synthase inhibitor oligomycin (3 µM), the mitochondrial uncoupler carbonyl cyanide-4-(trifluoromethoxy)phenyl-hydrazone (FCCP; 1 µM), and the respiratory chain inhibitors antimycin A (1.5 µM) and rotenone (3 µM).

Quantitative PCR (qPCR) Analysis.

RNA was extracted from cells using the RNeasy Mini Kit or the RNeasy Plus Mini Kit (Qiagen) according to the manufacturer's instructions. cDNA synthesis was performed using the M-MLV reverse transcriptase (Invitrogen) or the iScript cDNA synthesis kit (Bio-rad). qPCR was performed with TaqMan Gene Expression Master Mix (Thermo Fisher Scientific) and TaqMan probes (Thermo Fisher Scientific), or with iQ™ SYBR Green Supermix (Bio-rad). Data were calculated using the ΔΔCt method. For TaqMan method, the following assays were used: human ACTB Hs99999903_m1; c-MYC Hs00153408_m1; HK2 Hs00606086_m1. For SYBR method, qPCR primers for human FGFR1-FGFR4, human β-actin, mouse FGFR1-FGFR4 and mouse β-actin were ordered from Qiagen. Mouse HK2 qPCR primers both purchased from Qiagen and designed in-house were used. The sequences of in-house designed qPCR primers are (5' to 3'): Mouse HK2 (CGG-TACACTCAATGACATCCGA, SEQ ID NO: 1; TTCAC-CAGGATGAGTCTGACC, SEQ ID NO: 2), human GAPDH (TGCACCACCAACTGCTTAGC, SEQ ID NO: 3; GGCATGGACTGTGGTCATGAG, SEQ ID NO: 4), human PFKL (TGGATGACAAGAGGTTTGACG, SEQ ID NO: 5; GGATGGCCAGGGAGAAGTTAG, SEQ ID NO: 6), human PFKP (GTCAAACTCTCGGAGAACC, SEQ ID NO: 7; TTTCTCAGAGGTGATGGGT, SEQ ID NO: 8), human PFKM (AGGATTGGCCTTATCCAGG, SEQ ID NO: 9; CAGCTTCCTCTATCTGCCC, SEQ ID NO: 10), human PKM1 (GAGGCAGCCATGTTCCAC, SEQ ID NO: 11; TGCCAGACTCCGTCAGAACT, SEQ ID NO: 12), human PKM2 (CAGAGGCTGCCATCTACCAC, SEQ ID NO: 13; CCAGACTTGGTGAGGACGAT, SEQ ID NO: 14) and human RPLP0 (TCTGCATTCTCGCTTCCTGG, SEQ ID NO: 15; CAGGACTCGTTTGTACCCGT, SEQ ID NO: 16).

ChIP-qPCR.

ChIP assays were performed using SimpleChIP® Plus Enzymatic Chromatin IP Kit (Cell Signaling) according to manufacturer's protocol with some minor modifications. Basically cells cultured on 20-cm dishes were fixed for 10 min by adding 37% formaldehyde solution to the culture medium to a final concentration of 1%. Fixation was quenched with glycine for 5 min at room temperature. Cells were washed twice with ice-cold PBS, scraped into 2 ml PBS, and centrifuged at 5,000 rpm for 10 min. The cell pellets from two 20-cm dishes were combined and lysed in 1 ml lysis buffer. The lysate was then centrifuged at 5,000 rpm for 5 min at 4° C. and the pellet was resuspended in 100 µl nuclease digestion buffer. The DNA was digested with 0.5 µl of Micrococcal Nuclease for 20 min at 37° C. to a length of approximately 150-900 bp (checked by agarose gel electrophoresis). Lysates were centrifuged and the pellet was resuspended in 500 µl ChIP buffer and sonicated for 3×30 s at power level 2 and 40% constancy. The solution was centrifuged at 10,000 rpm for 10 min, and the supernatant was collected which was the cross-linked chromatin. For chromatin immunoprecipitation (IP), 150 µl of cross-linked chromatin was used for each IP and mixed with rabbit anti-c-myc antibody (Abcam, 1: 50) or same amount of rabbit IgG control at 4° C. overnight. 2% of cross-linked chromatin was saved as input control for qPCR reaction later on. 30 µl of Protein G magnetic bead slurry was added to each IP reaction and incubate for 2 hrs at 4° C. with rotation. The magnetic beads were washed 3 times with ChIP low salt buffer and once with ChIP high salt buffer. The bound chromatin on the beads was released in ChIP elution buffer by heating at 65° C. for 30 min with vortex at 1,200 rpm. The chromatin was then digested with Protease K and purified using spin column. The DNA was eventually eluted in 50 µl DNA elution buffer. The amount of precipitated DNA from each sample was quantified by qPCR using primers flanking the Myc binding element in the HK2 gene. The reading was normalized to that of DNA purified from the previously saved cross-linked chromatin (2% input). The reading by DNA from IP using Myc antibody against that from IgG IP indicated the antibody efficiency for ChIP assay. The qPCR primers (flanking the E-boxes) for detecting Myc binding element are (5'-3'): GCCCCGCAGGTAGTCAGG, SEQ ID NO: 17; AGCCACGATTCTCTCCACG, SEQ ID NO: 18.

xCELLigence Real-Time Cell Analysis (RTCA).

HDLEC proliferation was measured through using xCEL-Ligence RTCA instrument (Roche Dignostics) and E-plate 16 (a modified 16-well plate, Roche Dignostics). E-plate 16 was coated with 0.1% gelatin, loaded with 100 µl cell-free medium and left in tissue culture hood for 30 min. to reach equilibrium. E-plate 16 was placed into RTCA instrument to measure the background impedance. Thereafter, 100 µl cell suspensions with less than 8000 cells were added into each well of E-plate 16, which was then placed in tissue culture incubators for 30 min. to allow cells to settle down before being measured by RTCA device. The impedance value of E-plate 16 was automatically monitored every 15 min. with 3-4 replicates for each treatment. For experiments which required measurement of FGF2 effect on cell proliferation, HDLECs were resuspended in EBM2 plus 3% FBS before being plated into E-plate 16. 10-12 hr. after RTCA measurement, the monitor program was paused and E-plate 16 was taken out from the device to add 2 µl FGF2 (1:100) or vehicle to each well, after which the measurement continued. For the other experiments, full supplemented medium (EBM2 plus 5% FBS and growth factors) was used in E-plate 16.

Wound Healing Migration Assay.

HDLEC migration was measured in a wound healing assay, which employed Ibidi culture-inserts (Ibidi) to generate the wound. An ibidi culture-insert is 9 mm×9 mm×5 mm (w×l×h) and is composed of two wells. One or two inserts were placed into one well of 6-well plates. After being coated with 0.1% gelatin, both wells of inserts were loaded with 100 µl cell suspension. When cells became fully confluent after attachment, culture inserts were carefully removed by sterile tweezers to start cell migration. For studying the effect of HK2 siRNA on FGF2-stimulated migration and the effect of FGFR1 siRNA and/or FGFR3 siRNA on cell migration, would healing process was monitored for approximately 12 hr. To assess the rescue effect of HK2 overexpression in FGFR1 siRNA-treated cells, cell migration was evaluated in approximately 17 hr. Nikon ELIPSE TS100 microscope with a PixeLINK camera was used to image cells at the first time point ($T_0$) and the last time point ($T_{end\ point}$). For data analysis, ImageJ was used to measure the wound area in $T_0$ and $T_{end\ point}$. Migration area was obtained by subtracting Area ($T_{end\ point}$) from Area ($T_0$).

Three-Dimensional Bead Sprouting Assay.

HDLECs were trypsinized and mixed with collagen-coated Cytodex® microcarrier beads (Sigma) in a ratio of 2500 beads to $1×10^6$ cells in warm EGM-2 medium in a 15 ml falcon tube. The mixture was incubated at 37° C. for 4 hr., with shaking every 20 min. to ensure even coating of the beads. After 4 hr., the coated beads were transferred to a 6-well plate in 2 ml of EGM-2 medium per well and incubated at 37° C. overnight. The next day, coated beads were embedded into a fibrinogen gel. For each well of a 24-well plate, 300 µl of 3 mg/mL fibrinogen in PBS was used, along with 100 µg/ml of aprotinin (Sigma) and 1.5 unit/ml of thrombin (Sigma). Approximately 250 coated beads were embedded in each well. The plate was then incubated at 37° C. for one hr. to generate a clot. After the gel solidified, human lung fibroblasts in EGM-2 medium were seeded on top at a concentration of 20,000 cells/well. The medium was changed every other day (full EGM-2 medium with 200 ng/mL of FGF2), and the plates were imaged on day 6 using a spinning disk confocal microscope (Perkin Elmer). ImageJ was used to measure the sprout length for the data analysis.

Adenovirus for In Vitro and In Vivo Analysis.

Adenovirus encoding GFP, empty CMV vector, sFGFR1-IIIC (Murakami, M. et al., 118, 3355-3366, (2008)), HK2 (Wu, R. et al. Circulation research 108, 60-69, (2011)), or Myc (from Vector Biolabs) for in vitro experiments was amplified in 293A cells according to the user manual of ViraPower™ Adenoviral Expression System (Life Technologies). Virus was tittered using Adeno-X™ Rapid Titer Kit (Clontech Laboratories). For in vivo experiments, LacZ- or sFGFR1-IIIC was amplified and purified at University of North Carolina virus vector core. Neonatal pups were injected i.p. with $5\times10^8$ FFU of LacZ or sFGFR1-IIIC virus at P0 and P1. Tail skin was harvested at P6 using a method published previously (Xu, Y. et al., J Cell Biol 188, 115-130, (2010)).

Analysis of Lymphatic Development.

To induce Cre activity during embryonic stage, each pregnant mouse was injected i.p. with 2 mg tamoxifen (Sigma, T5648) for two consecutive days (E10.5-E11.5, E11.5-E12.5 and E12.5-E13.5). Skin tissues were harvested at E15.5. Standard whole-mount immunohistochemistry procedure was carried out to stain the skin and diaphragm with antibodies against PECAM1 (BD Pharmigen, #553370), VEGFR3 (R&D Systems, #AF743), PROX1 (Angiobio, #11-002), Cx40 (ALPHA DIAGNOSTIC, #CX40-A), EGFP (Life Technologies, #A-11122; Abcam, #ab13970) and Alexa fluorescent $2^{nd}$ antibodies (Life Technologies). A spinning disk confocal microscope (Perkin Elmer) and a Leica SP5 confocal microscope were used to generate high-resolution images of immunostained samples. Stitch imaging mode was chosen to image samples of large size. ImageJ was employed to crop representative area from large, stitched images for exhibition. For quantification of lymphatic development in the anterior dorsal skin, comparable regions (based on the blood vessel pattern) between different samples were selected and cropped out of those stitched images as regions of interest (ROIs) for further analysis. Lymphatic development parameters, e.g. branching points and LEC nucleus numbers, were measured using ImageJ with "Lymphatic Vessel Analysis" plugin. If considerably big area within a ROI was destroyed during skin dissection, that sample was excluded for analysis.

Retinal Vasculature Analysis.

Gene deletion was induced by intragastric injections to pups with 50 μg tamoxifen (1 mg/ml) at postnatal day P0, P1 and P2. Mice were sacrificed at P5 for analysis of retinal vasculature as previously described. The retinas were incubated with IsolectinB4 and the following antibodies: anti-Collagen IV (Millipore, #AB769,), anti-ERG1/2/3 (Santa Cruz, #SC353), anti-phospho-histone 3 (PH3, Millipore, #06-570). Retinas were imaged using a Leica SP5 confocal microscope with a Leica spectral detection system (Leica SP detector) and the Leica application suite advanced fluorescence (LAS-AF) software. Quantification of retinal vascular development and immunostaining were done using the Biologic CMM Analyser Software and ImageJ.

Analysis of Cycle Distribution.

Dorsal skin explants were harvested from E15.5 mouse embryos, and minced into ice-cold Dulbecco's Modified Eagle's Medium supplemented with 20% fetal bovine serum and 1.25 mg/ml collagenase. Samples were incubated for 30 min. at 37° C., and mechanically dissociated by repeated pipetting until a single cell suspension was achieved. Samples were then centrifuged for 1 min at 2000×g at 4° C., and cell pellet was resuspended in PBS supplemented with 10% FBS, 5.5 mM glucose, and 20 mM HEPES. Cells were incubated in the presence of Hoechst 33342 (25 μg/ml) 30 min. at 37° C., and then additionally for 15 min. at 37° C. in the presence of Pyronin Y (0.5 μg/ml) as well as fluorescently conjugated antibodies: PECAM1-FITC (BD Pharmingen) and LYVE1-Alexa647 (eBioscience). Samples were washed and resuspended in 0.5 ml PBS on ice for subsequent analysis. Blood and lymphatic endothelial cells were identified by flow cytometry as PECAM1$^+$/LYVE1$^-$ and PECAM1$^+$/LYVE1$^+$ events respectively, and for each population, cell cycle distribution was determined by relative DNA (Hoechst) and RNA (Pyronin Y) content.

FACS to Sort LECs for qPCR Analysis.

Dorsal skin explants were harvested from E15.5 mouse embryos into ice-cold Dulbecco's Modified Eagle's Medium supplemented with 20% fetal bovine serum and 1 mg/mL collagenase. Samples were incubated for 1 hr. at 37° C., and mechanically dissociated by repeated pipetting until a single cell suspension was achieved. Samples were then centrifuged for 1 min. at 2000×g at 4° C., and the cell pellet was resuspended in Hank's Buffered Saline Solution supplemented with 10% FBS, 5.5 mM glucose, and 20 mM HEPES. Cells were incubated in the presence of fluorescently conjugated antibodies CD31-FITC (BD Pharmingen #553372), CD45-PECy7 (eBioscience #25-0451-82) and Lyve1-Alexa647 (eBioscience #50-0443-82) for 30 min. at 37° C. Samples were pelleted for 1 min. at 2000×g at 4° C., resuspended in 0.5 mL PBS on ice, and filtered through a 35 m nylon mesh prior to flow cytometry analysis and cell sorting. Blood endothelial cells were identified by FACS as CD31$^+$/CD45$^-$/Lyve1$^-$ and lymphatic endothelial cells were identified as CD31$^+$/CD45$^-$/Lyve1$^+$ events, and cells from each population were sorted into RLT lysis buffer (Qiagen) for mRNA preparation (RNeasy Micro kit), cDNA library construction, and subsequent qPCR analysis. Mouse HK2 qPCR primers both purchased from Qiagen and designed in-house were used. Mouse β-actin primers were from Qiagen. When analyzing qPCR results, wells whose melting curve peaks appeared at the incorrect temperature were excluded.

Corneal Lymphangiogenesis Model.

Slow-releasing pellets containing FGF2 were made as previously described (Tang, Z. et al. JoVE, (2011)). Surgery to implant the pellets into the mouse cornea was performed as reported (Cao, R. et al. Nature protocols 6, 817-826, (2011)). Adult Prox1-CreER$^{T2(KI)}$; HK2$^{flox/flox}$ and control mice were i.p. injected with tamoxifen (150 μg/g body weight) every the other day (seven injections total) before the cornea surgery. 1 week after the pellet implantation, eyeballs were harvested for cornea dissection and immunostaining with LYVE1 (Angiobio, #11-034) and PECAM1 (BD Pharmigen, #553370) antibodies and then used for imaging (spinning disk confocal microscopy) and quantification analysis (ImageJ).

Murine Orthotopic Pancreatic Tumor Model.

The murine pancreatic tumor cell line Panc02 was obtained from Prof. Wiedenmann (Charité University Hospital, Berlin). $1\times10^6$ tumor cells were injected subcapsularly in the head region of the pancreas of anaesthetized female C57Bl/6 mice (7-9 weeks old, Charles River, France) using a 30-gauge needle. At day 3 after tumor inoculation, tumor-bearing mice were treated daily with SSR (30 mg/kg/day) or vehicle (0.6% methylcellulose) via oral gavage. At day 9, primary tumors were removed, weighted, and tumor volumes (V) were calculated using the formula $V=0.52\times(a^2\times b)$, where a represents the smallest tumour diameter and b represents the largest tumour diameter. The incidence of tumor invasion into adjacent organs, hemorrhagic ascites, and regional celiac and mesenteric lymph node metastases were recorded, and confirmed by immunohistochemistry on paraffin sections. Paraffin-embedded 7 m sections were prepared and used for immunohistochemistry using the following antibodies: anti-LYVE1 (Upstate-Cell Signaling Solutions, Bio-connect, Huissen, The Netherlands) and anti-VEGFR3 (eBiosciences). The lymph vessel area in the peritumoral area was analysed using the KS300 software (Zeiss).

Statistical Analysis.

No statistical analysis was performed to pre-determine sample size. For cornea lymphangiogenesis assay, the sample size was estimated based on a previous report (Cao, R. et al. Nature protocols 6, 817-826, (2011)). Randomization and blinding was not used in the present animal studies. Statistical analysis was performed using GraphPad Prism 7. Statistical significance between two groups was determined by two-tailed unpaired t-tests (assume normal distribution, with or without Welch's correction), and statistical significance between multiple groups was calculated using one-way ANOVA with post-hoc tests. Graphs present the mean value±standard error of the mean (SEM).

The results of experiments are now described.

Example 1

Disruption of FGF Signaling Inhibits Lymphangiogenesis and Angiogenesis

To analyze the role of FGF signaling in mammalian lymphatic development, soluble pan-FGF receptor trap sFGFR1-IIIC was used to block FGF activity (Murakami, M. et al., Current opinion in hematology 15, 215-220, (2008)). When tested in human dermal lymphatic endothelial cells (HDLECs), sFGFR1-IIIC inhibited FGF2-induced ERK activation to the same extent as DN-FGFR1 (FIG. 6A). Injection of an adenovirus encoding sFGFR1-IIIC into mouse pups at postnatal day 0 (P0) and P1 resulted in significant inhibition of tail skin lymphatic formation when examined at P6 (FIGS. 6B-6C).

Figure 1B:
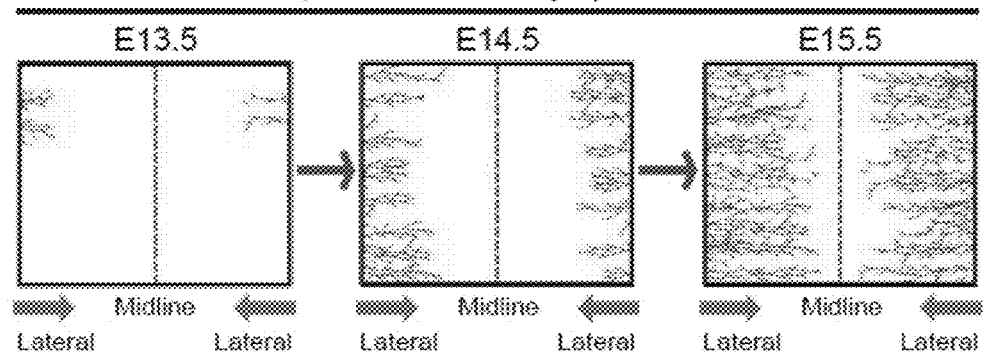
Figure 6D:
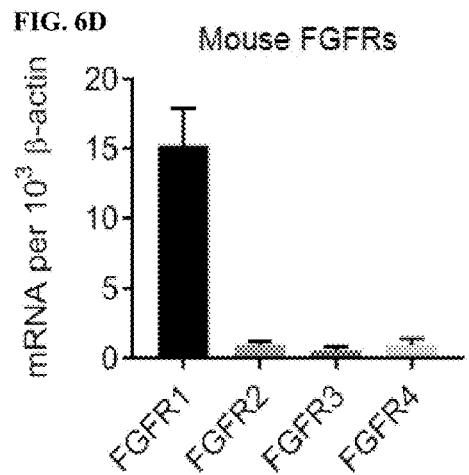
Figure 6E:
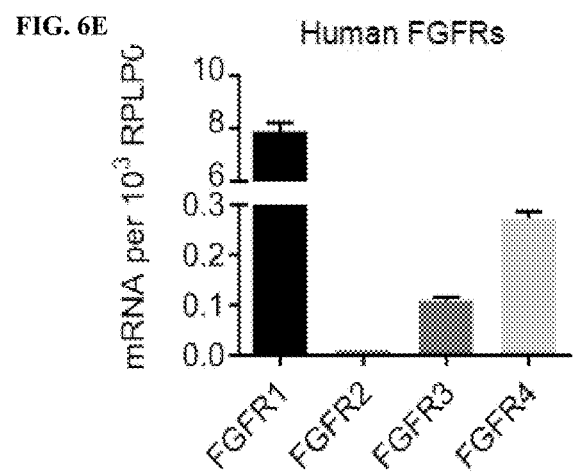
Figure 6F:
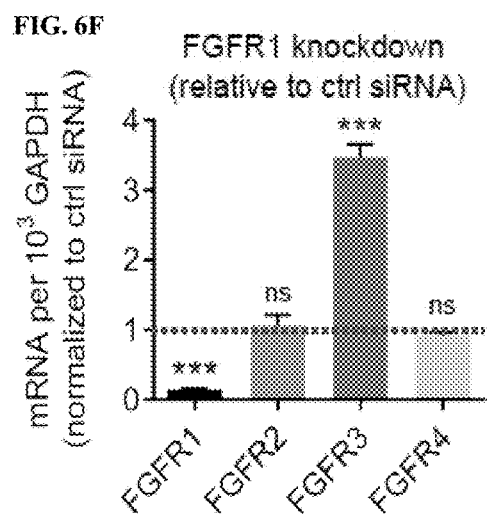
Figure 6G:
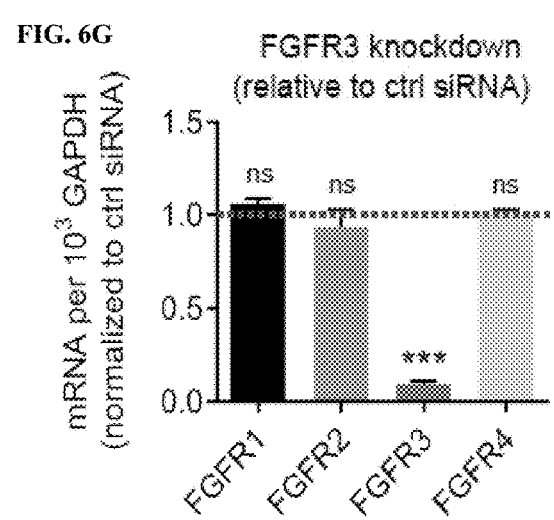
Figure 16A:
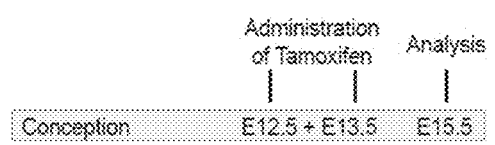
FIGS. 16A-16H are a series of images and graphs illustrating the effect of endothelium-specific deletion of HK2 from E12.5 on the lymphatic and blood vessel development in the skin.
Figure 16B:
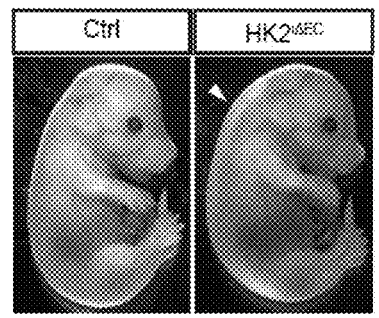
Figure 16C:
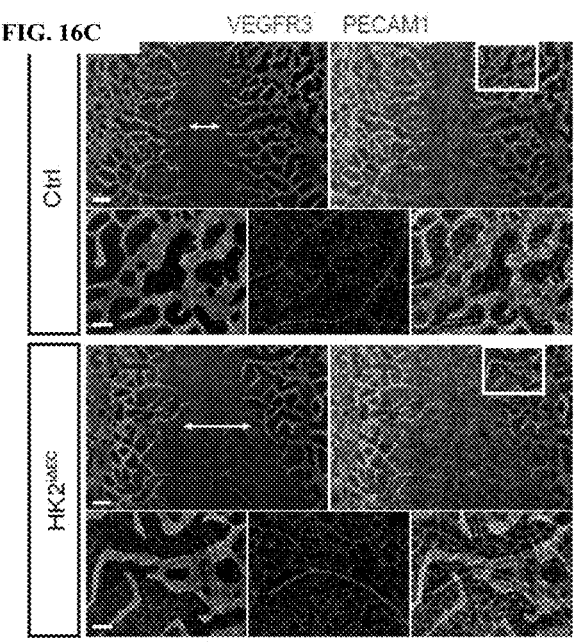
Figure 16D:
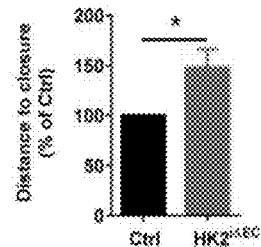
Figure 16E:
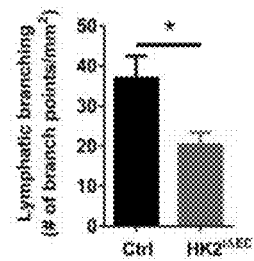
Figure 16F:
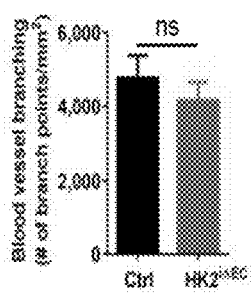
Figure 16G:

In order to identify specific FGFR(s) required for lymphangiogenesis in vivo, the expression pattern of all FGFRs was examined first. FGFR1 was the most prominent isoform in both mouse skin LECs and human dermal lymphatic endothelial cells (HDLECs) (FIGS. 6D-6E). Its knockdown resulted in upregulation of FGFR3 expression (FIG. 6F) while knockdown of FGFR3 had no effect on other FGFR levels (FIG. 16G). Given the potential FGFR3 compensation following FGFR1 knockout, the effect of endothelium-specific FGFR1 deletion was examined next on lymphatic development either by itself or on the global $FGFR3^{-/-}$ background using embryonic skin as a readout (James, J. M., et al., Development 140, 3903-3914, (2013)). LECs start to invade anterior dorsal skin at E12.5 and migrate towards the dorsal midline. By E15. 5-E16, lymphatic vessels from both sides fuse at the dorsal midline forming a primary lymphatic network (FIGS. 1A-1B).

Figure 1C:
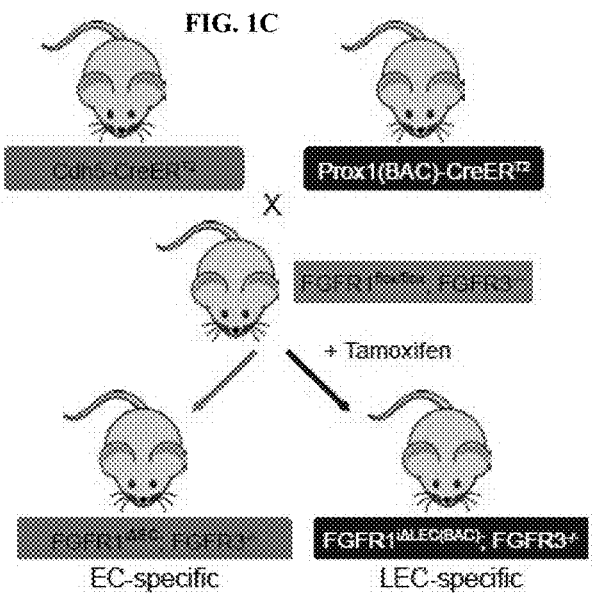
Figures 1D, 1E:
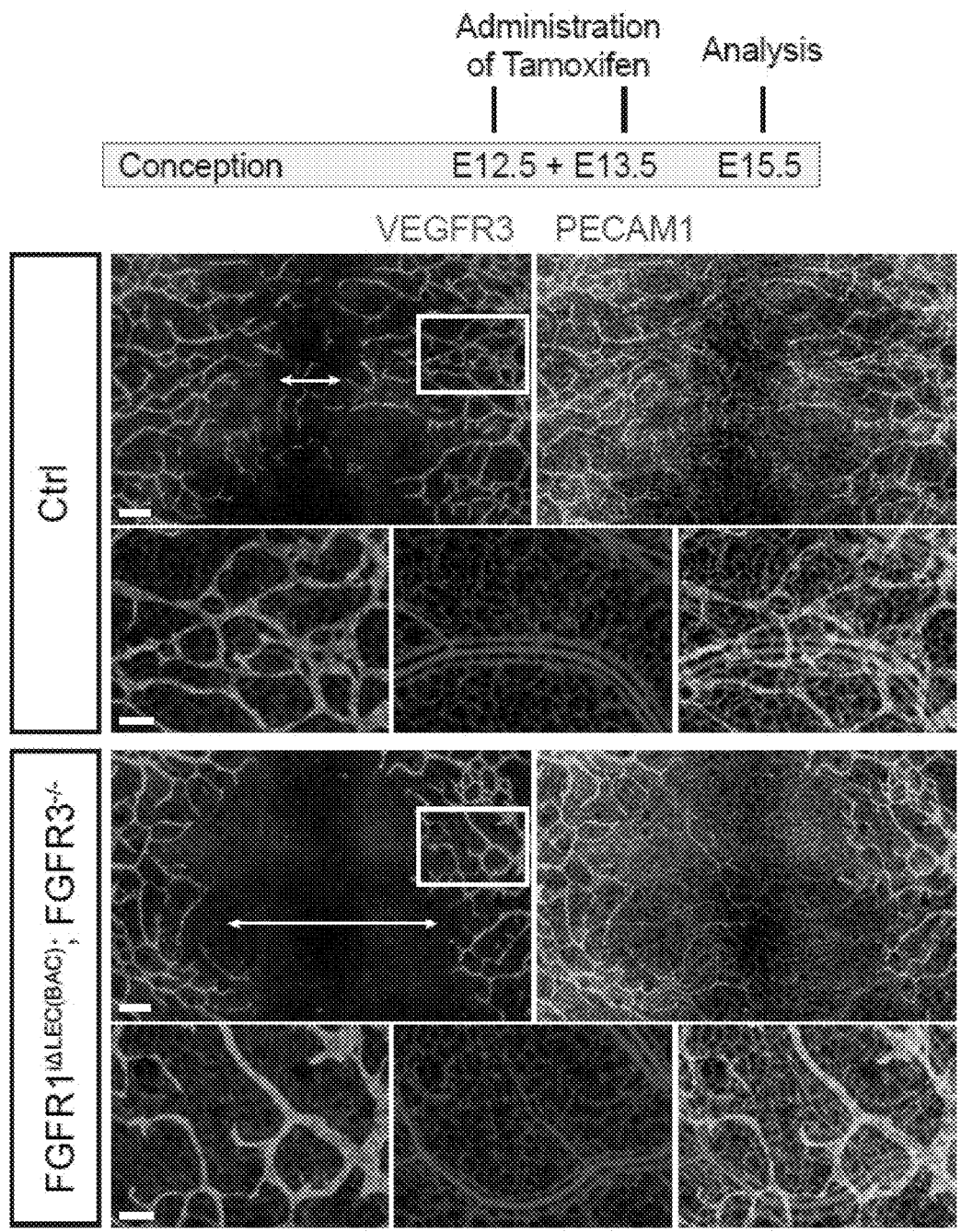
Figure 7A:
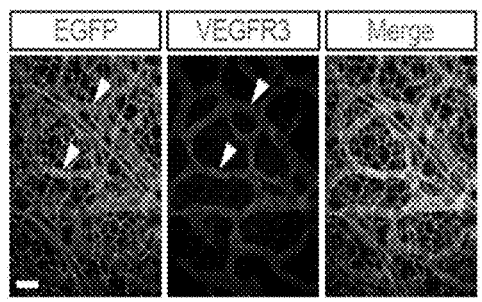
FIGS. 7A-7F are a series of images and graphs demonstrating that a single knockout of FGFR1 or FGFR3 has no effect on lymphatic development in the embryonic skin.
Figure 7B:
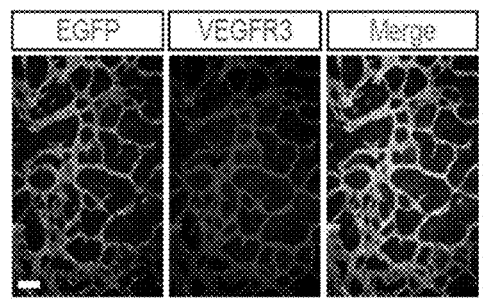
Figure 7C:
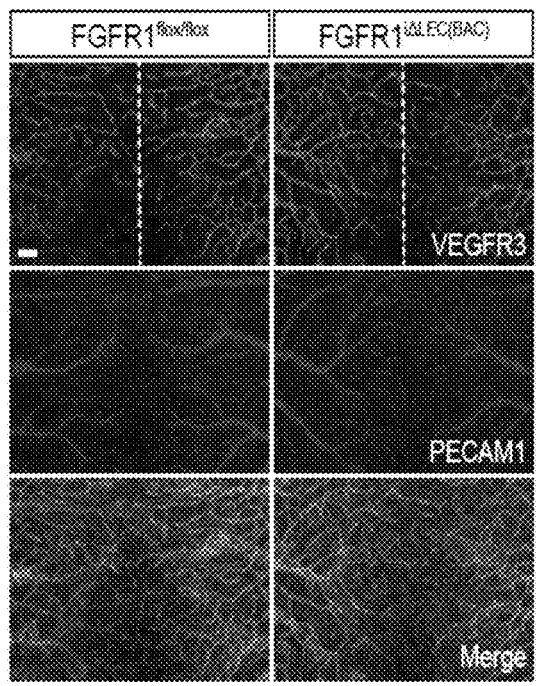
Figure 7D:
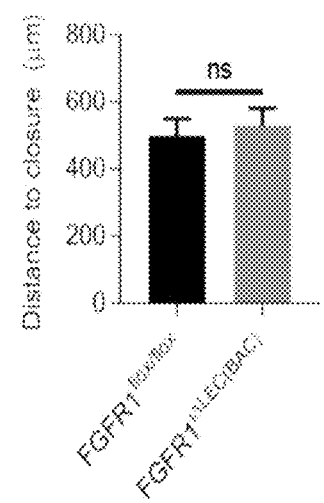
Figure 7F:
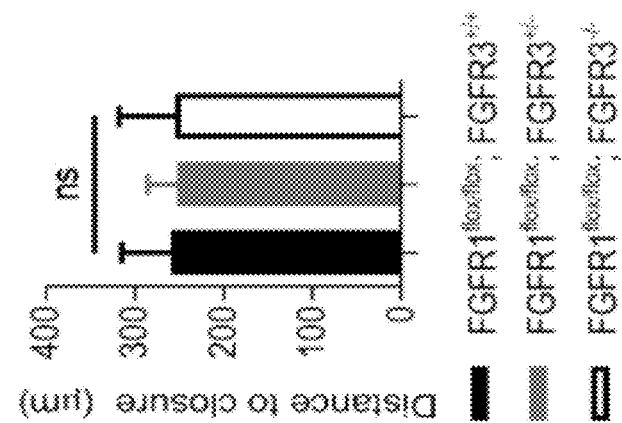
Figure 7E:
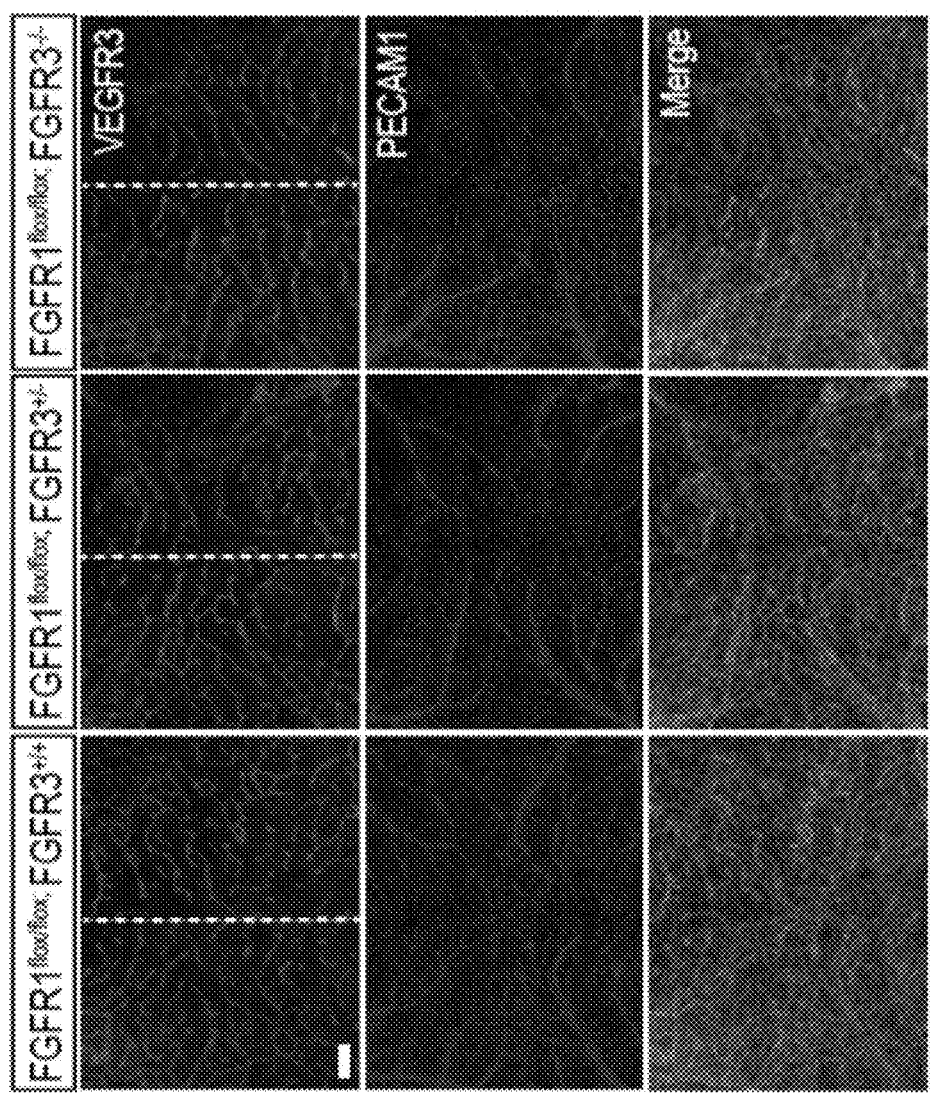
Figure 9A:
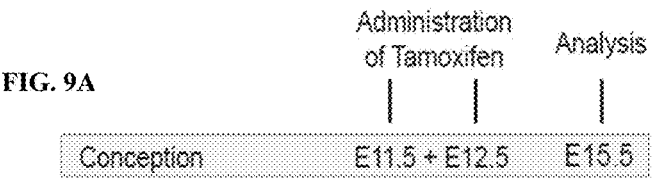
FIGS. 9A-9D are a series of images and graphs demonstrating that endothelial FGFR1/R3 deletion from E11.5 impairs dermal lymphatic development.
Figure 9B:
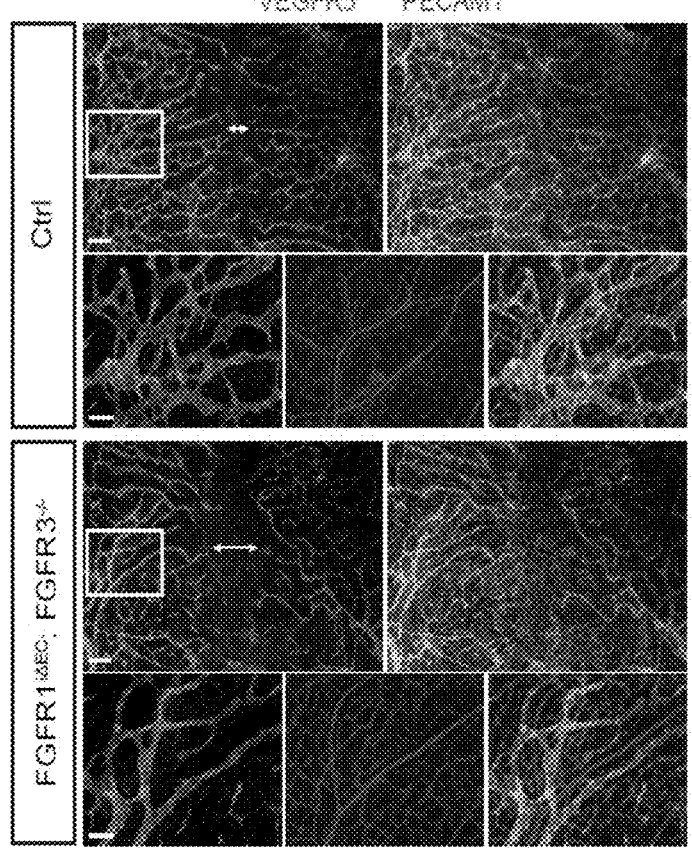
Figure 9C:
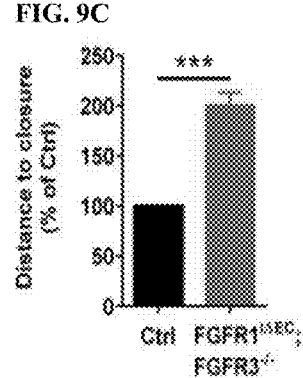
Figure 9D:
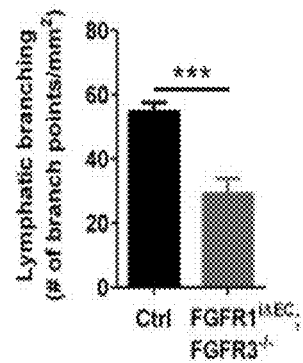

Cdh5-CreER$^{T2}$ and Prox1-CreER$^{T2(BAC)}$ driver lines were crossed with FGFR1$^{flox/flox}$ and $FGFR3^{-/-}$ mouse lines to generate pan-endothelium (FGFR1$^{i\Delta EC}$; $FGFR3^{-/-}$) and lymphatic endothelium (FGFR1$^{i\Delta LEC(BAC)}$; $FGFR3^{-/-}$) specific knockouts respectively (FIG. 1C). The excision efficiency of the tamoxifen-activated Cdh5-CreER$^{T2}$ and Prox1-CreER$^{T2(BAC)}$ constructs was assessed by crossing Cre driver mouse lines with the mTmG reporter mice. Cre activation at E12.5 and E13.5 resulted in a high degree of recombination in the skin lymphatic vessels at E15.5 with both Cre deleters (FIGS. 7A-7B).

Whole-mount staining of the embryonic mouse skin with anti-VEGFR3 and PECAM1 antibodies in single knockout FGFR1$^{i\Delta LEC(BAC)}$ or $FGFR3^{-/-}$ mice revealed no abnormalities (FIGS. 7C-7F). Induction of pan-endothelial FGFR1 deletion on the $FGFR3^{-/-}$ background (FGFR1$^{i\Delta EC}$; $FGFR3^{-/-}$) at E10.5 resulted in significant edema, the appearance of blood-filled lymphatics and reduced dermal lymphatic development (FIGS. 8A-8E). When the deletion was activated a day later (E11.5), reduced migration and branching of lymphatics were still evident (FIGS. 9A-9D).

Analysis of LEC-specific FGFR1/R3 double knockout (FGFR1$^{i\Delta LEC(BAC)}$; $FGFR3^{-/-}$) confirmed these findings, showing decreased LEC front migration, branching, and lower number of LECs in the skin (FIGS. 1D-1I). There was no appreciable difference in the size of the skin lymphatic vessels (FIGS. 1H-1J). The role of FGFR inhibition in suppressing pathological lymphangiogenesis was also explored herein. To this end, mice with orthotopic Panc02 tumors were orally treated with the SSR128129E inhibitor (Bono, F. et al. Cancer cell 23, 477-488, (2013); Herbert, C. et al. Cancer cell 23, 489-501, (2013)). LYVE1 immunohistochemistry revealed a significant reduction of the lymphatic vasculature in the peri-tumoral area in the inhibitor-treated mice compared to vehicle controls (FIGS. 1K-1L), indicating a potential therapeutic value of FGFR inhibitors as anti-lymphangiogenic agents.

Figure 10A:
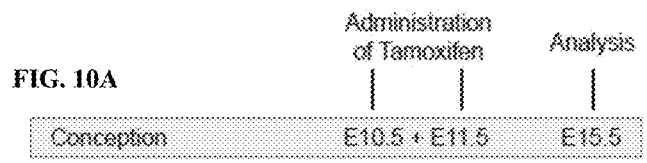
FIGS. 10A-10H are a series of images and graphs demonstrating that endothelial FGFR1/R3 is essential for blood vessel development in the embryonic skin.
Figure 10B:
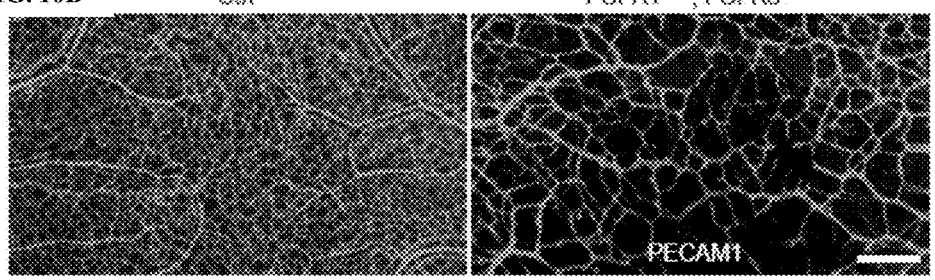
Figure 10C:
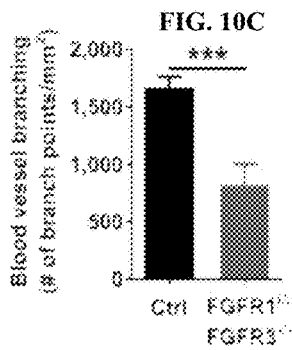
Figure 10D:
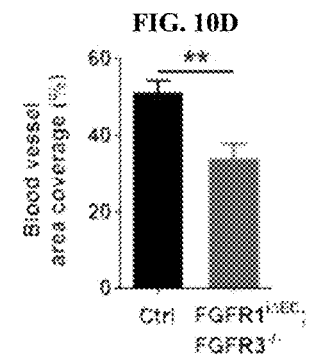
Figure 10E:
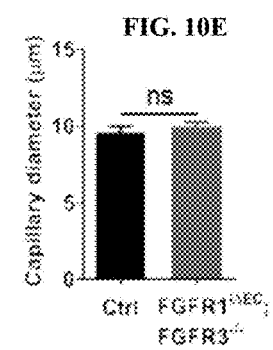
Figure 10F:
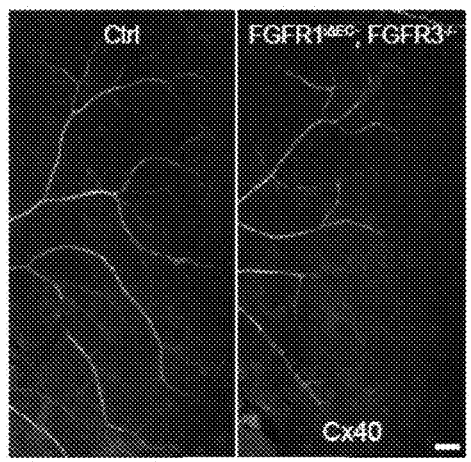
Figure 10G:
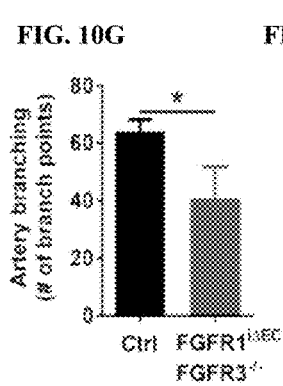
Figure 10H:
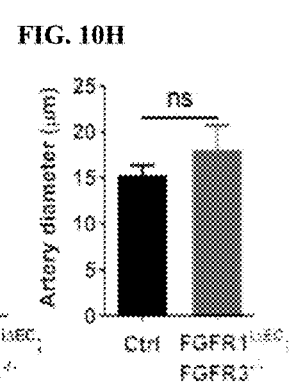
Figure 11A:
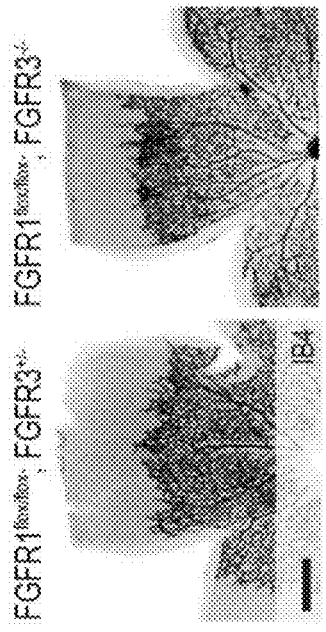
FIGS. 11A-11D are a series of images and graphs demonstrating that a single knockout of FGFR1 or FGFR3 does not affect retinal angiogenesis.
Figure 11B:
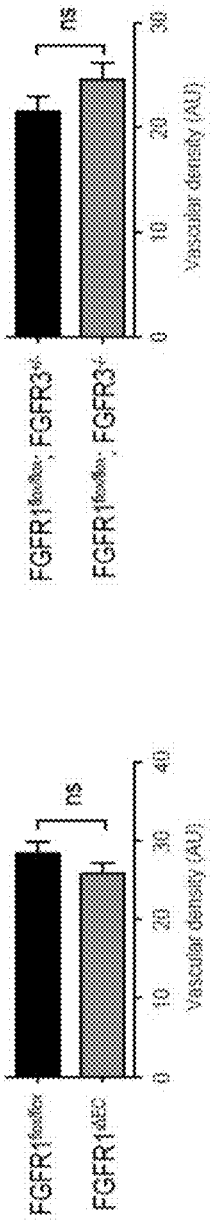
Figure 11C:
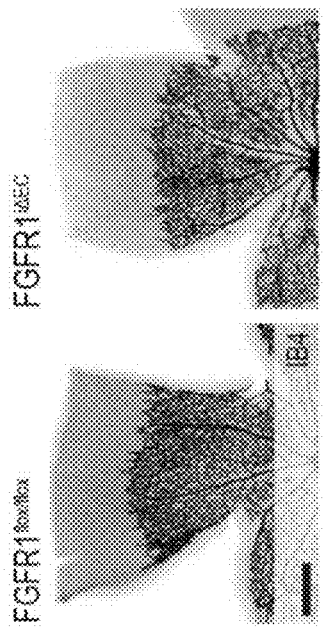
Figure 11D:
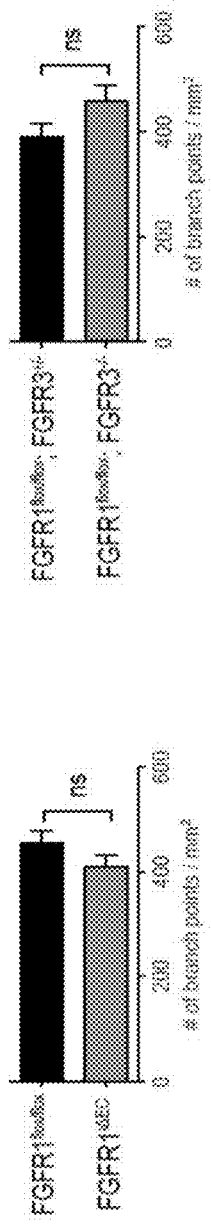

Given the observed effects of FGFR1/R3 deletion on lymphatic development, FGF signaling was next examined for a potential similar role in blood vessel development. Analysis of FGFR1$^{i\Delta EC}$; $FGFR3^{-/-}$ mice following Cre activation at E10.5 showed a significant reduction in the number of blood vessels, decrease in vessel branching and smaller blood vessel area in the skin at E15.5 (FIGS. 10A-10D). Examination of the arterial vasculature (Connexin 40 staining) also showed a reduction in branching (FIGS. 10F-10G). At the same time, there were no differences in capillary or arterial diameters (FIGS. 10E-10H).

Figure 2A:
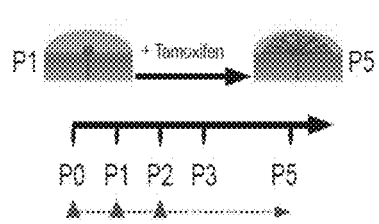
FIGS. 2A-2I are a series of images and graphs demonstrating that endothelial FGFR1/R3 are required for retinal angiogenesis.
Figure 2B:
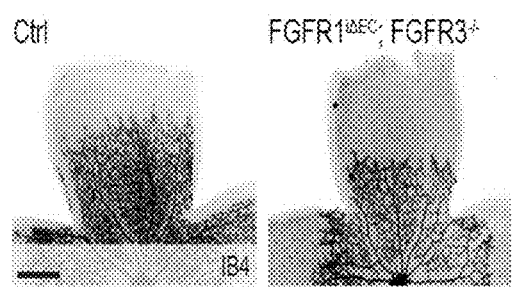
Figure 2C:
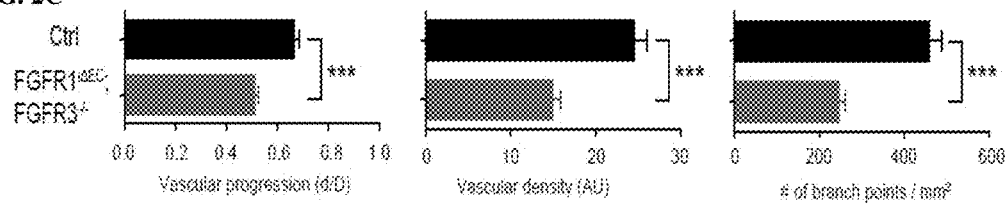
Figure 2D:
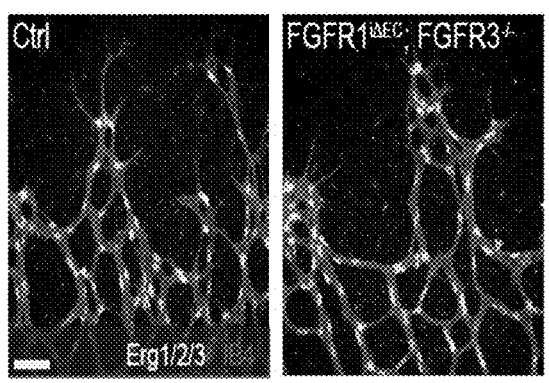
Figure 2E:
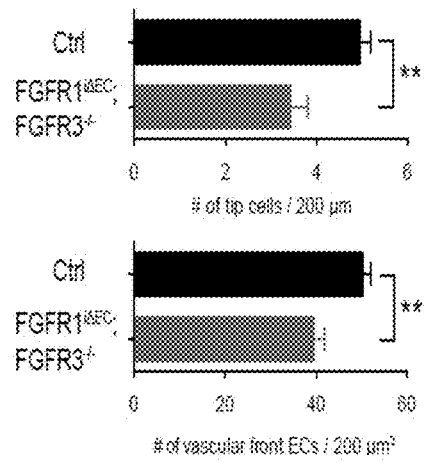
Figure 2F:
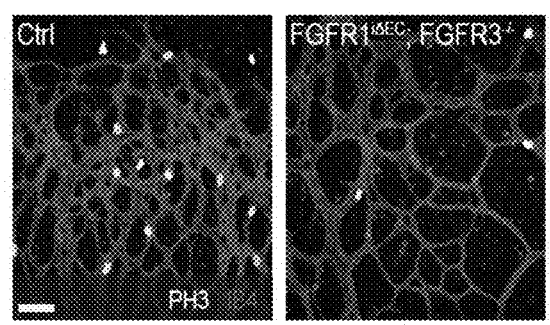
Figure 2G:
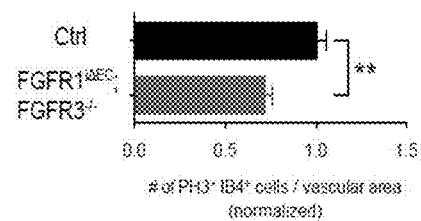
Figure 2H:
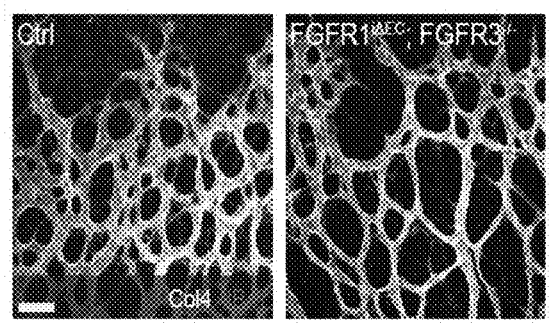
Figure 2I:
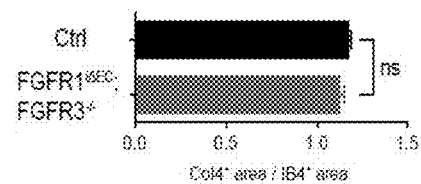

The role of FGF signaling in blood vascular development was further confirmed by examining retinal vascular development in FGFR1$^{i\Delta EC}$; $FGFR3^{-/-}$ mice after Cre activation at P0 (FIG. 2A). Endothelial deletion of both receptors resulted in a significant impairment of vascular growth and branching (FIGS. 2B-2C). In agreement with these observations, there was also a marked reduction in the number of tip cells (FIGS. 2D-2E) and extent of proliferation (FIGS. 2F-2G). No difference in vascular regression was observed (FIGS. 2H-2I). At the same time, no effects were observed in mice with single deletion of either FGFR1 or FGFR3 (FIGS. 11A-11D).

Figure 12A:
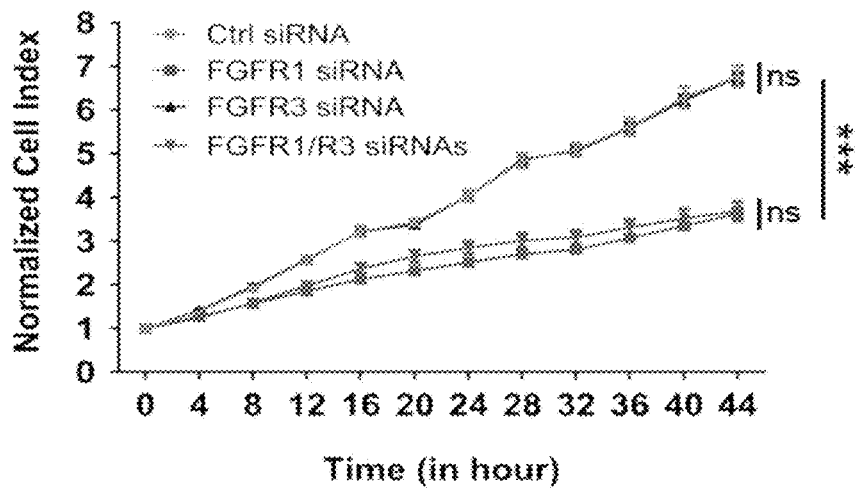
FIGS. 12A-12C are a series of images and graphs depicting the proliferation and migration of HDLECs with FGFR1 and/or FGFR3 knockdown.
Figure 12B:
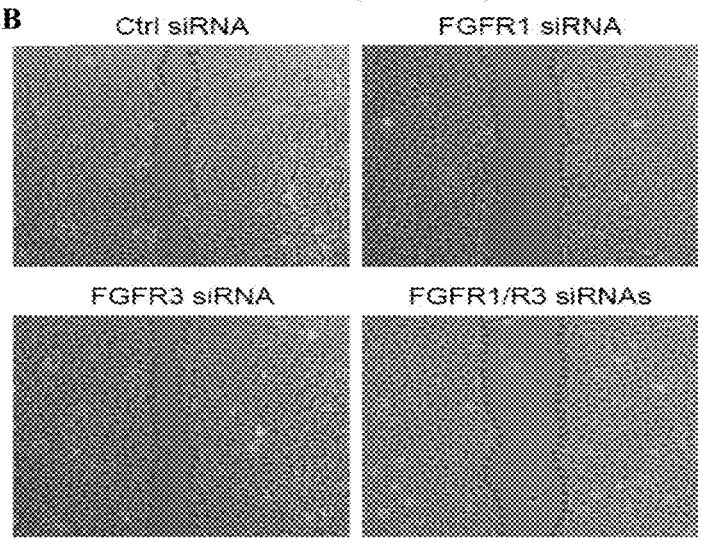
Figure 12C:
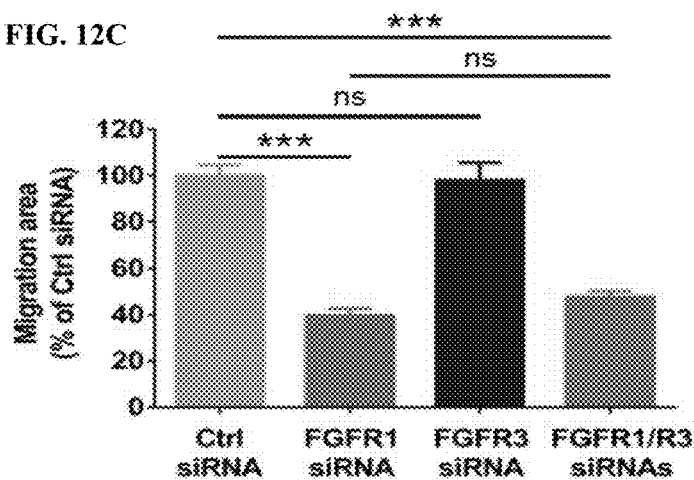

The effect of FGF signaling in LECs was examined next in vitro. Unlike in vivo, a knockdown of FGFR1 in HDLECs significantly reduced cell proliferation while FGFR3 downregulation had no effect (FIG. 12A). A double FGFR1/R3 knockdown was similar to FGFR1 knockdown in suppression of HDLEC proliferation (FIG. 12A). Similarly, FGFR1 knockdown inhibited HDLEC migration to the same extent of FGFR1/R3 double knockdown, but downregulation of FGFR3 did not affect this process (FIGS. 12B-12C).

Example 2

FGF Regulates Glycolysis in a Hexokinase 2-Dependent Manner

Figure 13A:
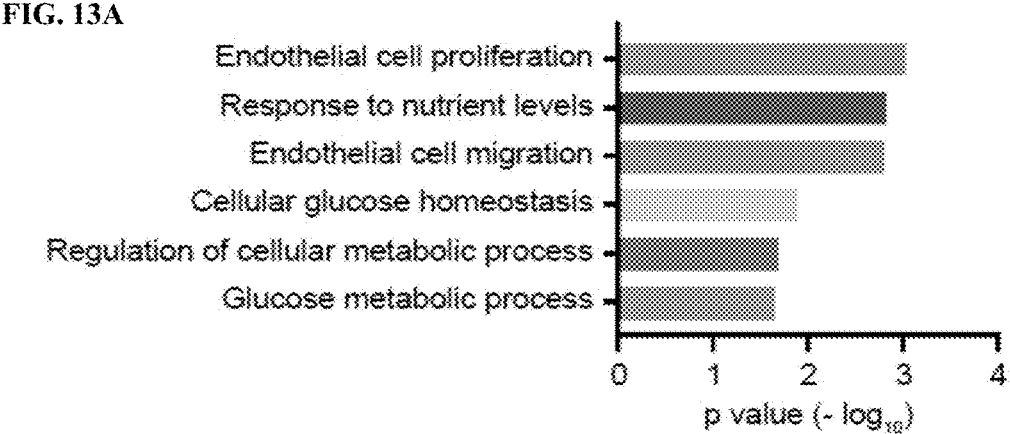
Figure 13B:
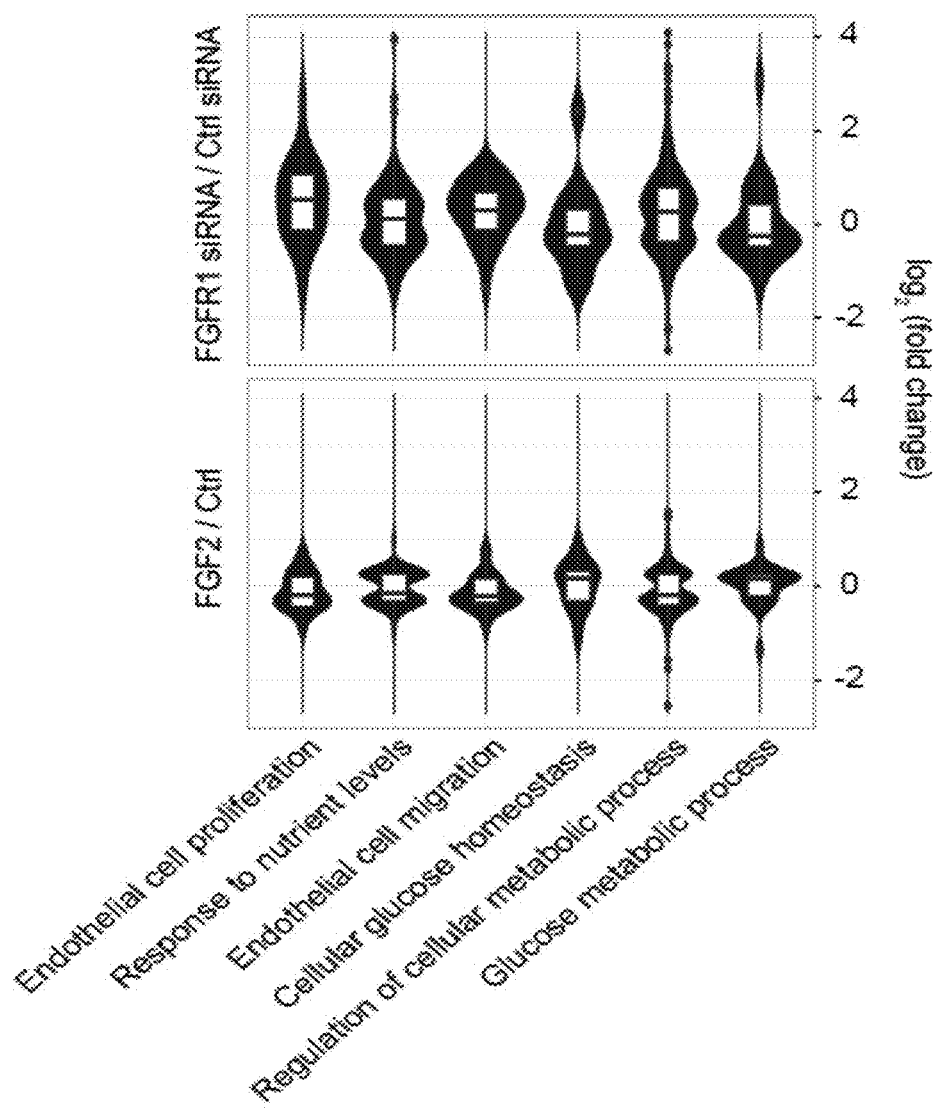

To establish the molecular basis of FGF-dependent regulation of vascular development, RNA sequencing (RNA-seq) analysis was carried out on LECs following stimulation with FGF2 or knockdown of FGFR1 expression (see Methods for details). Gene ontology analysis showed the expected statistical enrichment of molecular pathways related to endothelial cell proliferation and migration (FIGS. 13A-13B). Surprisingly, there also was enrichment among cellular metabolism processes (response to nutrient levels and regulation of cellular metabolic process) and, especially, glucose metabolism pathways (cellular glucose homeostasis and glucose metabolic process), suggesting that FGF signaling is involved in metabolic regulation (FIGS. 13A-13B).

Figure 3A:
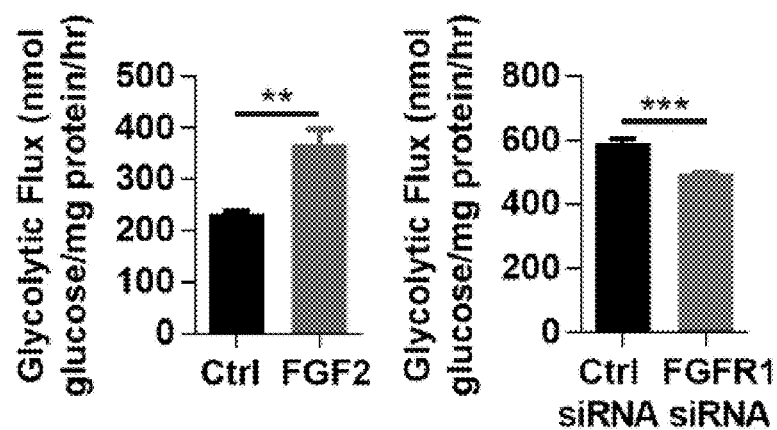
Figure 3B:
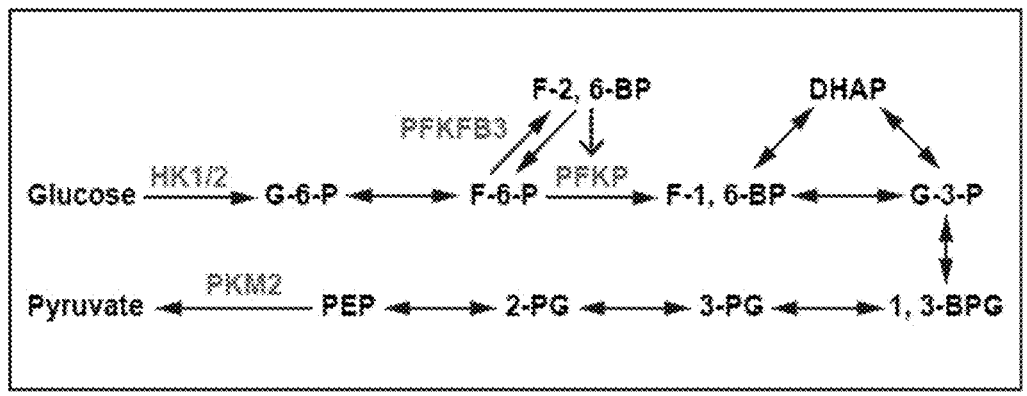
Figure 3C:
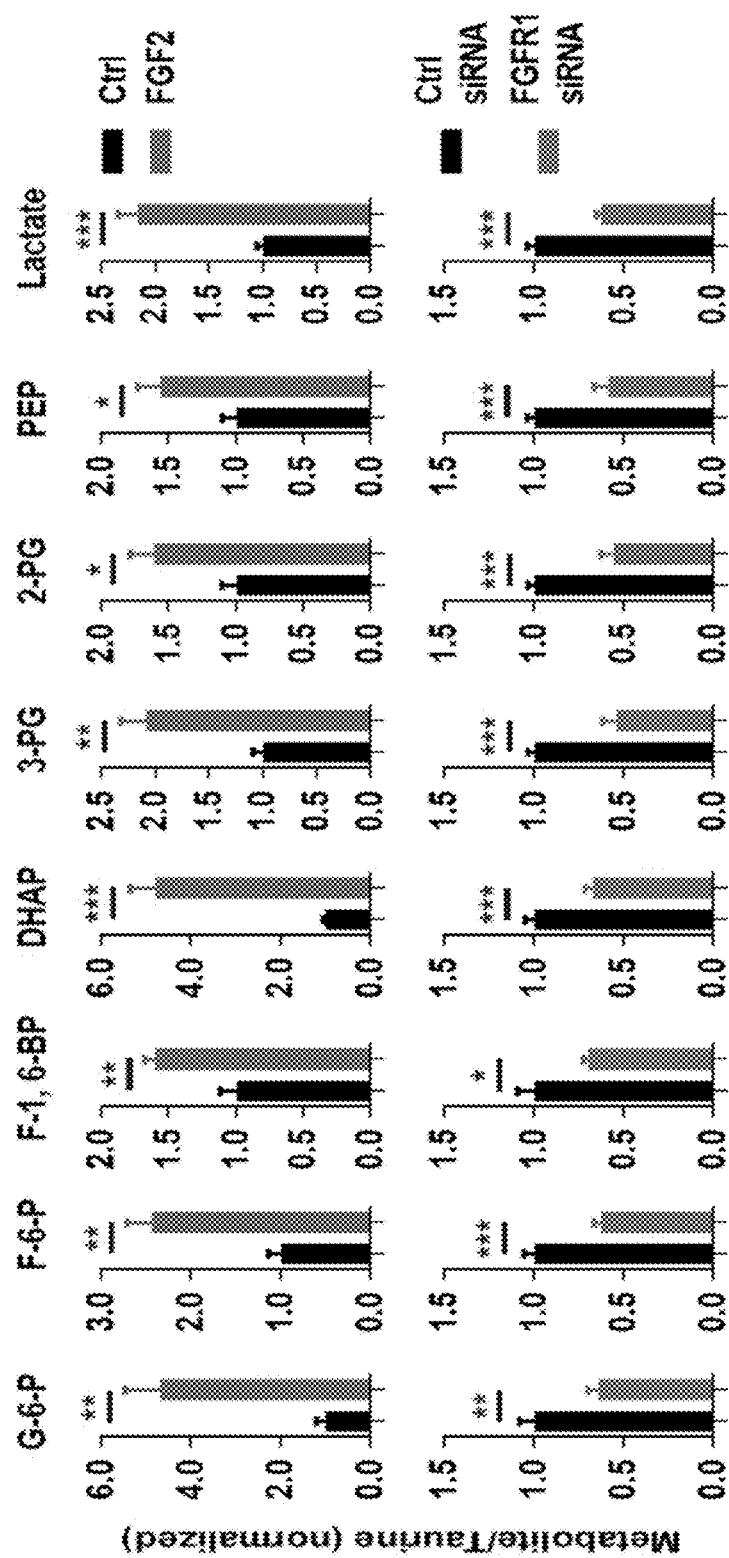

To assess the involvement of FGF in metabolic regulation, the contributions of major glucose metabolic pathways was examined first, including glycolysis and glucose oxidation, as well as glutamine oxidation and fatty acid oxidation to LECs energy generation. Flux analysis demonstrated that glycolysis was the most active process in LECs (FIG. 13C). Calculation of ATP generation based on the flux rate measurement showed that glycolysis contributed ~90% of the total ATP. HDLECs treatment with FGF2 doubled their glycolytic flux (FIG. 3A) and significantly increased glucose uptake (FIG. 13D). Conversely, knockdown of FGFR1 reduced the flux rate (FIG. 3A). Steady-state levels of glycolytic metabolites, including glucose-6-phosphate, fructose-6-phosphate, fructose-1,6-bisphosphate, dihydroxyacetone phosphate, 3-phosphoglycerate, 2-phosphoglycerate, phosphoenolpyruvate (FIG. 3B), and lactate, were all increased by FGF2 stimulation and decreased after FGFR1 knockdown (FIG. 3C). FGF signaling activation increased, while FGFR1 downregulation reduced, ATP production in HDLECs, consistent with the major contribution of glycolysis to energy generation (FIG. 3D).

To define the regulatory step involved in FGF-dependent control of LEC glycolysis, the expression of rate-limiting glycolytic enzymes was analyzed, including hexokinase (HK1 and HK2) (Wilson, J. E. The Journal of experimental biology 206, 2049-2057 (2003)), phosphofructokinase (PFK), and pyruvate kinase (PK). The focus with the latter two was on the isoforms most abundant in HDLECs (PFK-platelet (PFKP) and PK-muscle 2 (PKM2)) (FIGS. 13E-13F). 6-phosphofructo-2-kinase/fructose-2,6-bisphosphatase 3 (PFKFB3) which regulates blood vessel sprouting (De Bock, K. et al. Cell 154, 651-663, (2013)) was also assessed.

Figure 13G:
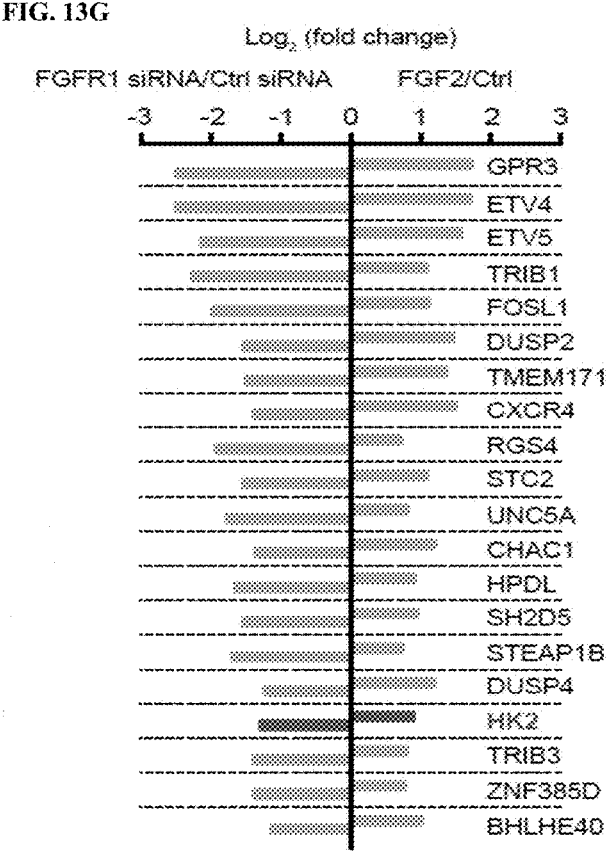

HDLEC stimulation with FGF2 induced a robust increase in HK2 expression, with minimal changes of other enzymes' expression (FIGS. 3E-3F). In agreement with these data, FGFR1 knockdown led to a significant reduction in HK2, but not of other enzymes' expression (FIGS. 3G-3H). The importance of HK2 was confirmed by analysis of RNA-seq data: it was the only glucose metabolic gene among the top twenty genes (ranked by fold change, see Methods for details) induced by FGF2 and downregulated by FGFR1 knockdown (FIG. 13G). Examination of skin LECs isolated from E15.5 FGFR1$^{i\Delta LEC(BAC)}$; FGFR3$^{-/-}$ embryos confirmed the reduction in HK2 expression (FIG. 3I).

Figure 13H:
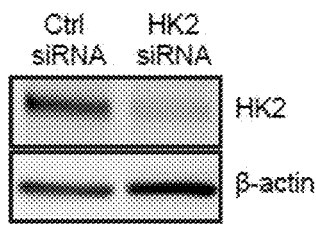
Figure 13I:
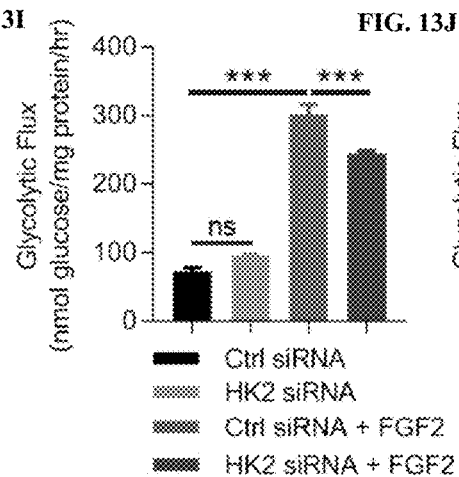
Figure 13J:
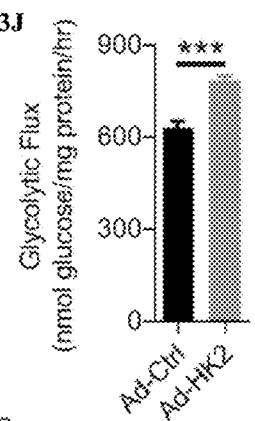

Importantly, HK2 knockdown significantly reduced FGF2 induction of the glycolytic flux (FIGS. 13H-13I) while adenoviral-mediated HK2 overexpression significantly increased glycolytic flux. Notably, the magnitude of this effect was comparable to that of FGF2 treatment (FIG. 13J), pointing to HK2 as a key target of FGF signaling in the regulation of glycolysis.

Since the knockout of FGFR1 and FGFR3 in the endothelium also reduced angiogenesis, it was examined whether FGF signaling regulates glycolysis and enzyme expression in blood endothelial cells. Similar to findings in LECs, treatment of human umbilical vein endothelial cells (HUVECs) with FGF2 enhanced glycolysis and selectively induced HK2 expression albeit to a lesser extent than in LECs (FIGS. 14A-14C), indicating that FGF regulation of angiogenesis and lymphangiogenesis share similar metabolic mechanisms.

Besides FGF2, several other growth factors including VEGFC, VEGFD, insulin-like growth factors 1 and 2 (IGF1 and IGF2), and platelet-derived growth factor-BB (PDGFBB) can regulate lymphangiogenesis (Tammela, T. et al., Cell 140, 460-476, (2010); Zheng, W., et al., The Journal of clinical investigation 124, 878-887, (2014)). It was further tested herein whether any of these growth factors were also tested for any influence glycolysis in HDLECs. VEGFC stimulation increased glycolytic flux, albeit to a lesser extent than FGF2, VEGFD and IGF1 had no effect, and IGF2 and PDGFBB reduced flux (FIG. 14D). Consistent with these findings, VEGFC, but not other growth factors, increased HK2 expression without affecting other enzymes (FIGS. 14E-14F).

Example 3

HK2 Role in the Lymphatic and Blood Endothelium

Figure 15A:
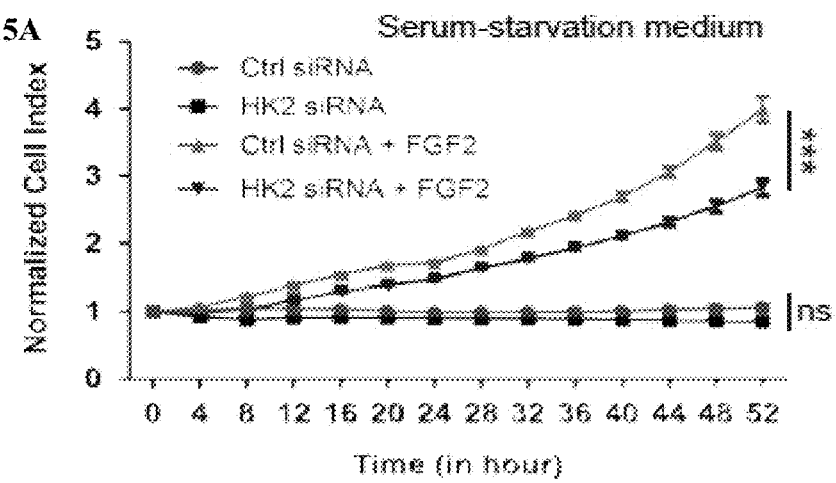
FIGS. 15A-15F are a series of images and graphs depicting the role of HK2 in FGF-dependent cellular behaviors.
Figure 15B:
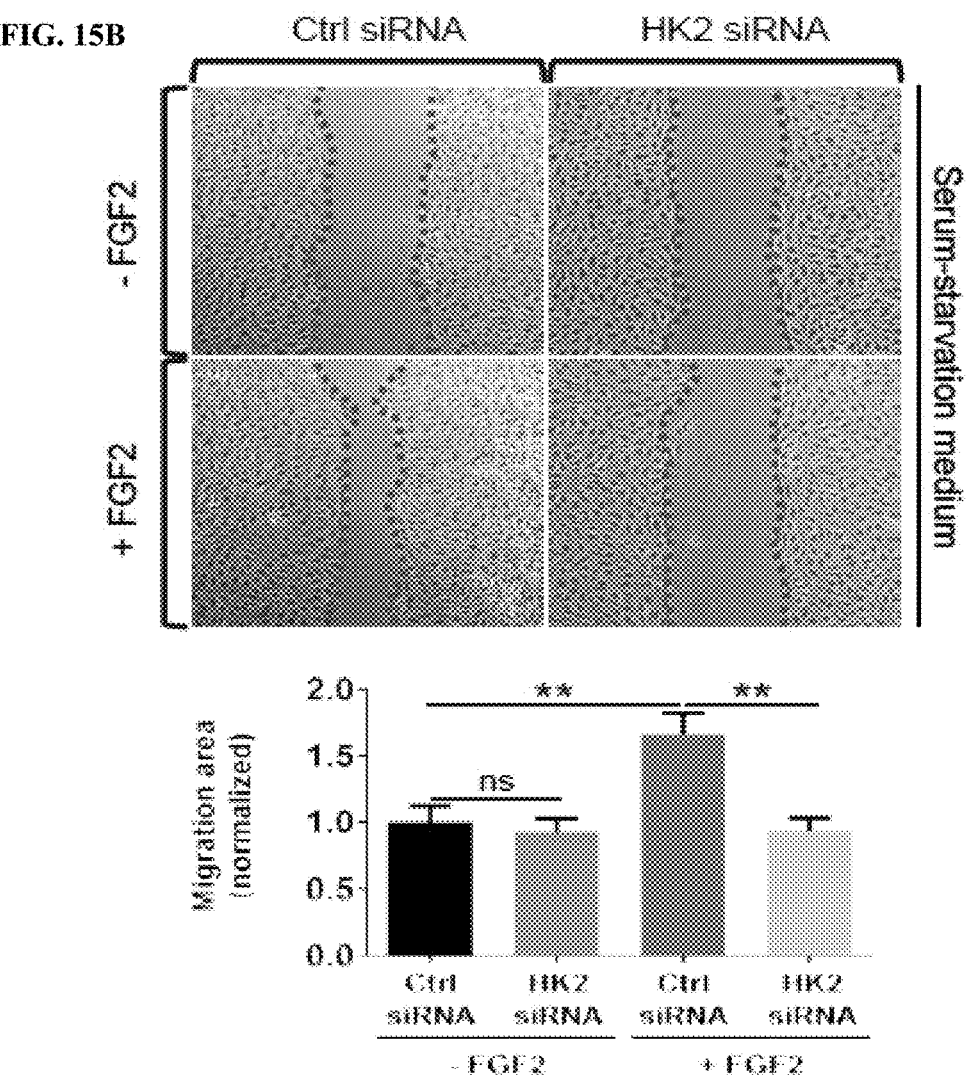
Figure 15C:
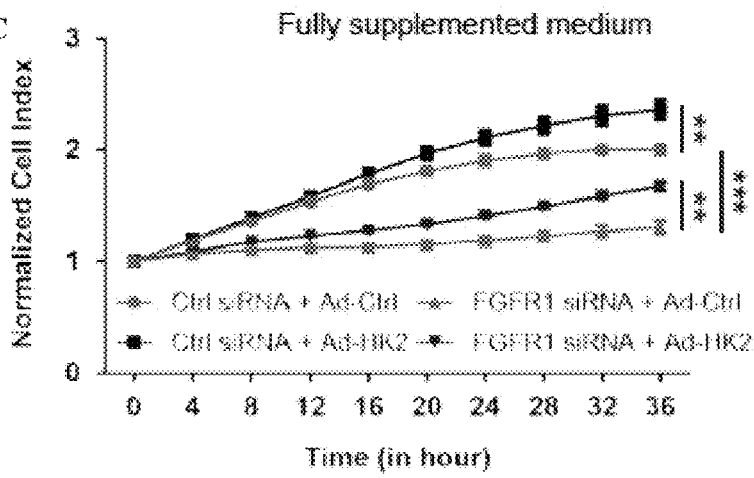
Figure 15D:
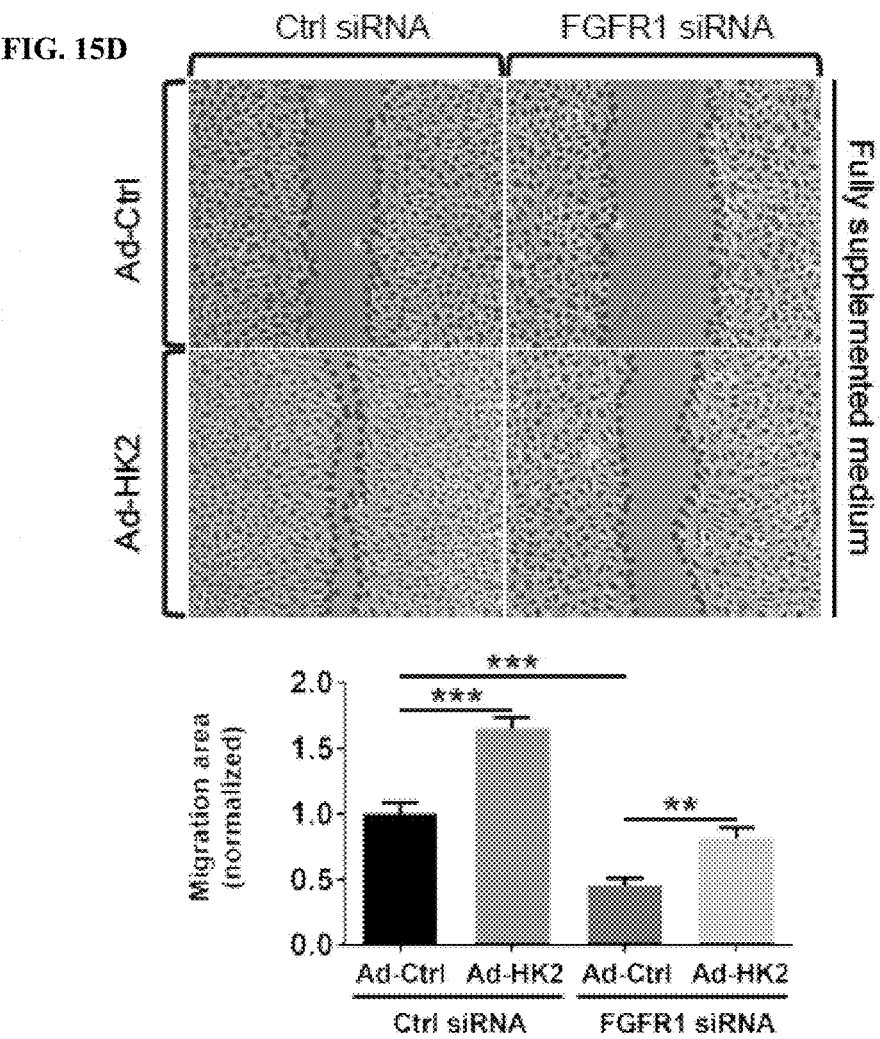

The above data point to an important role of HK2 in lymphatics. FGF2 stimulation of both HDLEC proliferation and migration was significantly reduced by HK2 knockdown (FIGS. 15A-15B). The FGFR1 knockdown-induced decrease in HDLEC proliferation and migration was rescued by adenoviral HK2 expression (FIGS. 15C-15D).

Figure 15E:
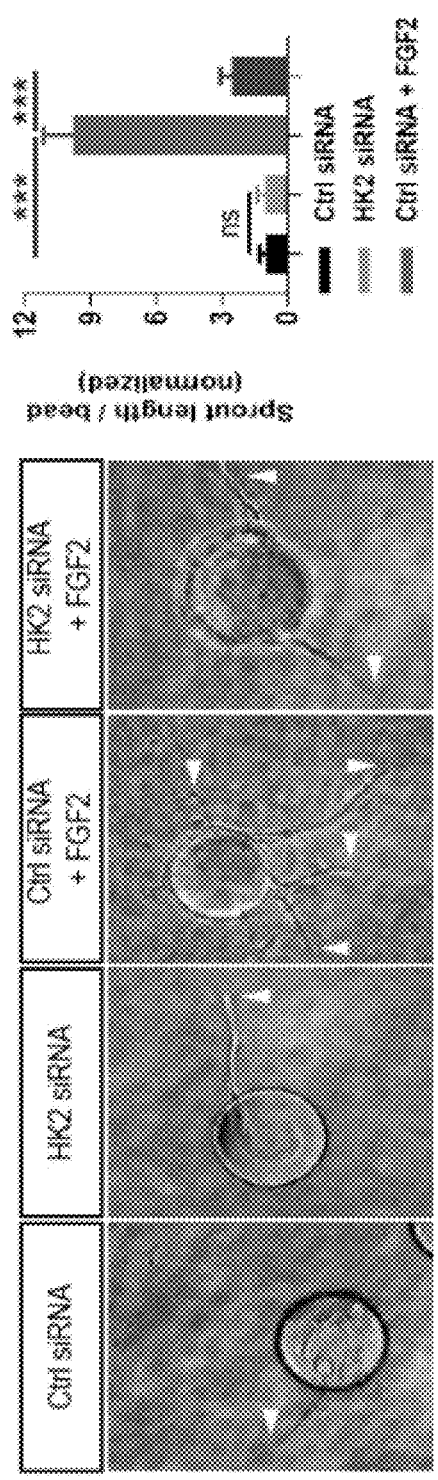
Figure 15F:
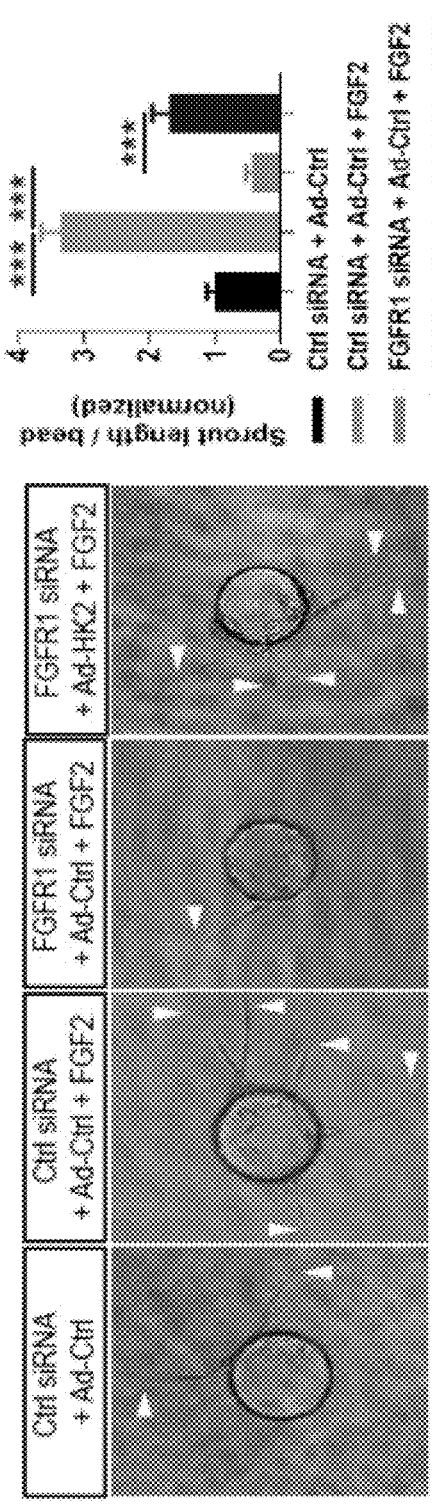

To examine LEC sprouting, beads coated with HDLECs treated with HK2 or control siRNAs were stimulated with FGF2. While FGF2 induced a strong sprouting response in control cells, HK2 knockdown almost completely blocked FGF2-induced sprouting (FIG. 15E). FGFR1 knockdown in HDLECs also fully blocked FGF2-induced sprouting; however, transduction of HK2 into HDLECs with FGFR1 knockdown partially restored their ability to sprout (FIG. 15F).

Next, a mouse line with an endothelial-specific deletion of HK2 (HK2$^{i\Delta EC}$) was generated by crossing HK2$^{flox/flox}$ mice (Patra, K. C. et al., Cancer cell 24, 213-228, (201)) with Cdh5-CreER$^{T2}$ (FIG. 4A). When examined at E15.5 after E12.5 Cre activation, HK2$^{i\Delta EC}$, but not littermate control embryos, had extensive lymphedema (FIGS. 16A-16B). Examination of the anterior dorsal skin lymphatics demonstrated a reduction in the extent of migration towards the midline and branching in HK2$^{i\Delta EC}$, compared to Cre$^-$ littermate controls (FIGS. 16C-16E) while blood vascular development was not affected (FIGS. 16F-16G).

Figure 16H:
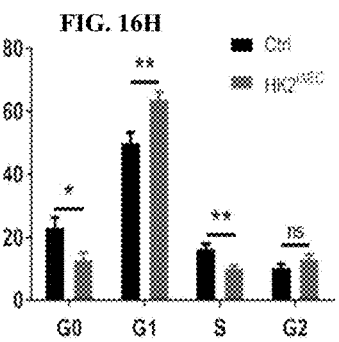
Figure 17A:
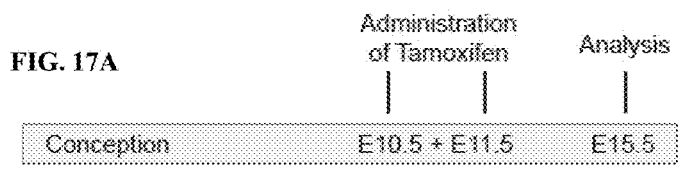
FIGS. 17A-17F are a series of images and graphs showing that the deletion of endothelial HK2 at early embryonic stage impairs blood vessel development in the embryonic skin.
Figure 17B:
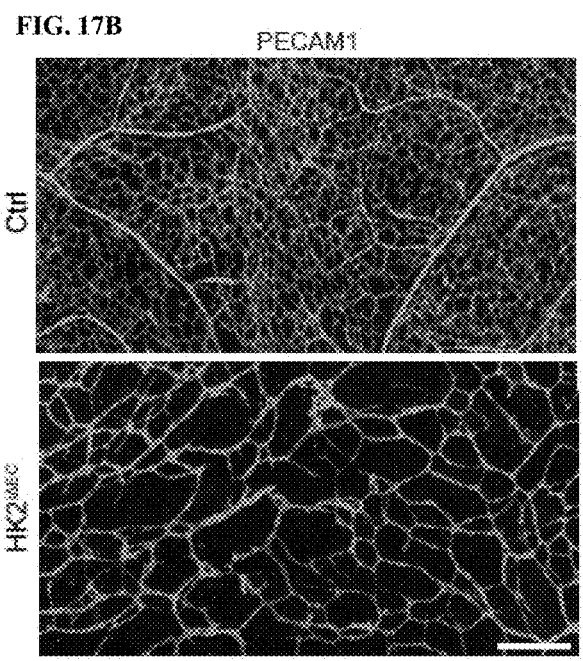
Figure 17C:
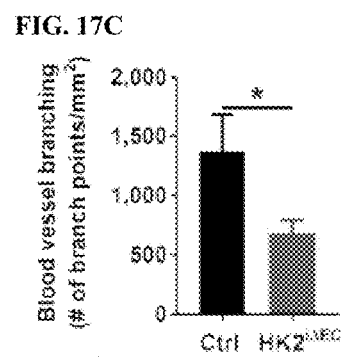
Figure 17D:
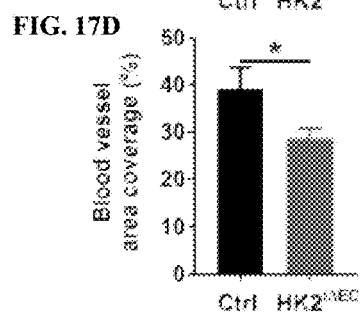
Figure 17E:
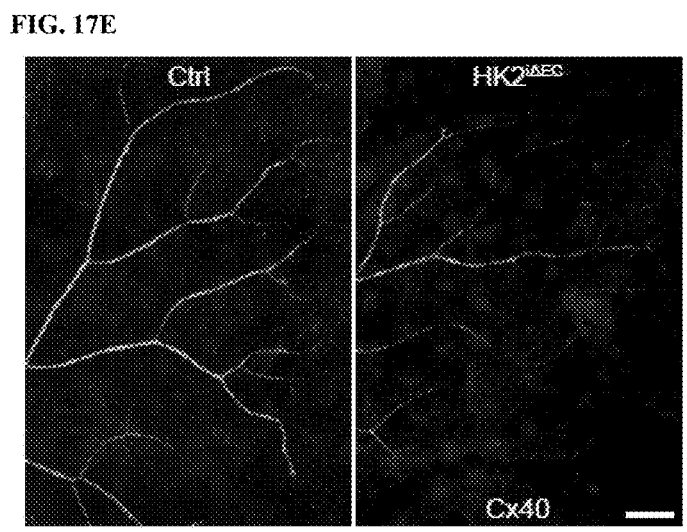
Figure 17F:
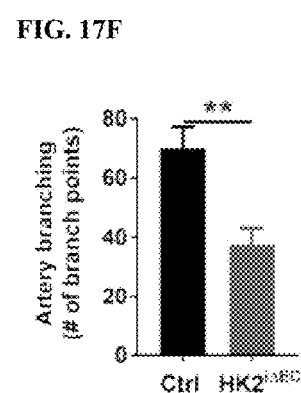

To determine if LEC proliferation is affected by HK2 deletion, flow cytometry was used to isolate LYVE1$^+$PE-CAM1$^+$ LECs from the embryonic skin of HK2$^{i\Delta EC}$ and littermate control mice. Analysis of cell cycle progression using Hoechst 33342 demonstrated a higher proportion of G1 and smaller proportion of S phase cells in LECs of HK2$^{i\Delta EC}$ compared to littermate control embryos (FIG. 16H).

Figure 4D:
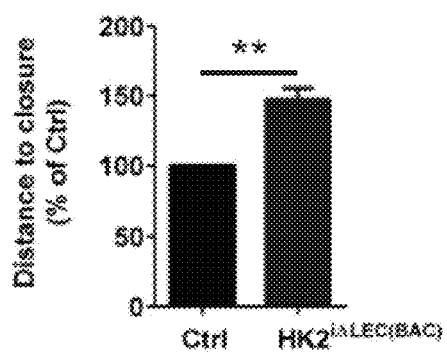
Figure 4E:
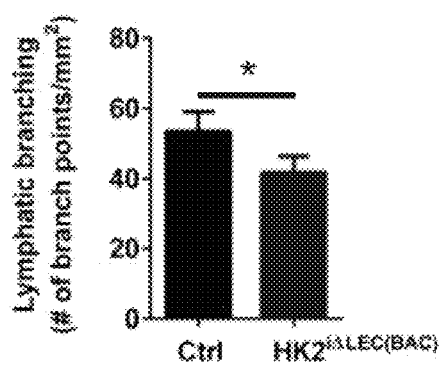

To confirm that these defects in lymphatic development were not secondary to any effects of HK2 deletion in the blood endothelium, HK2$^{flox/flox}$ ox ice were crossed with Prox1-CreER$^{T2(BAC)}$ (FIG. 4A). Immunostaining with anti-VEGFR3 antibody demonstrated a significant reduction in the skin lymphatic vessel development and branching at E15.5 after E12.5 Cre activation (FIGS. 4B-4E).

Figure 4F:
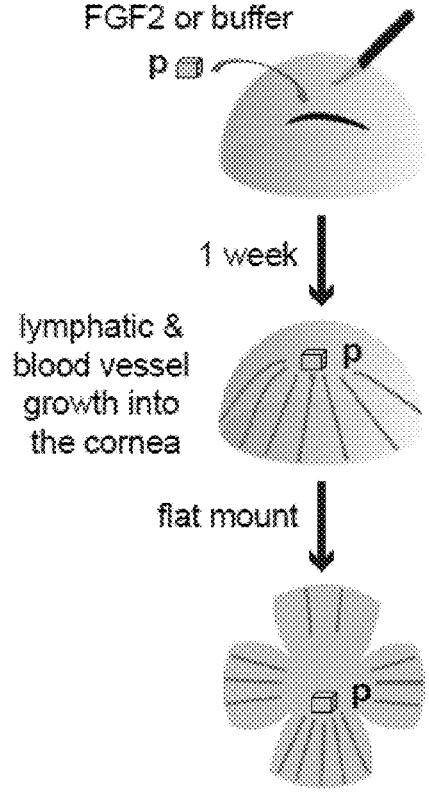
Figure 4G:
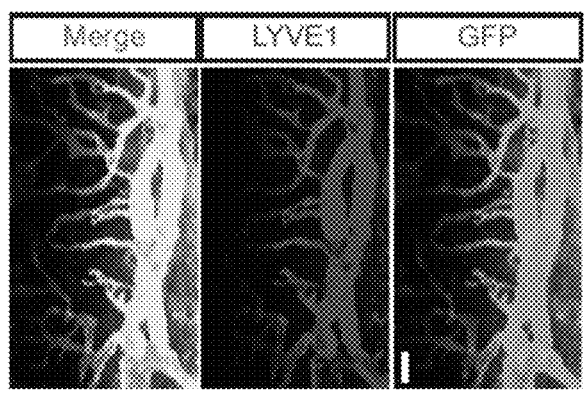
Figure 4H:
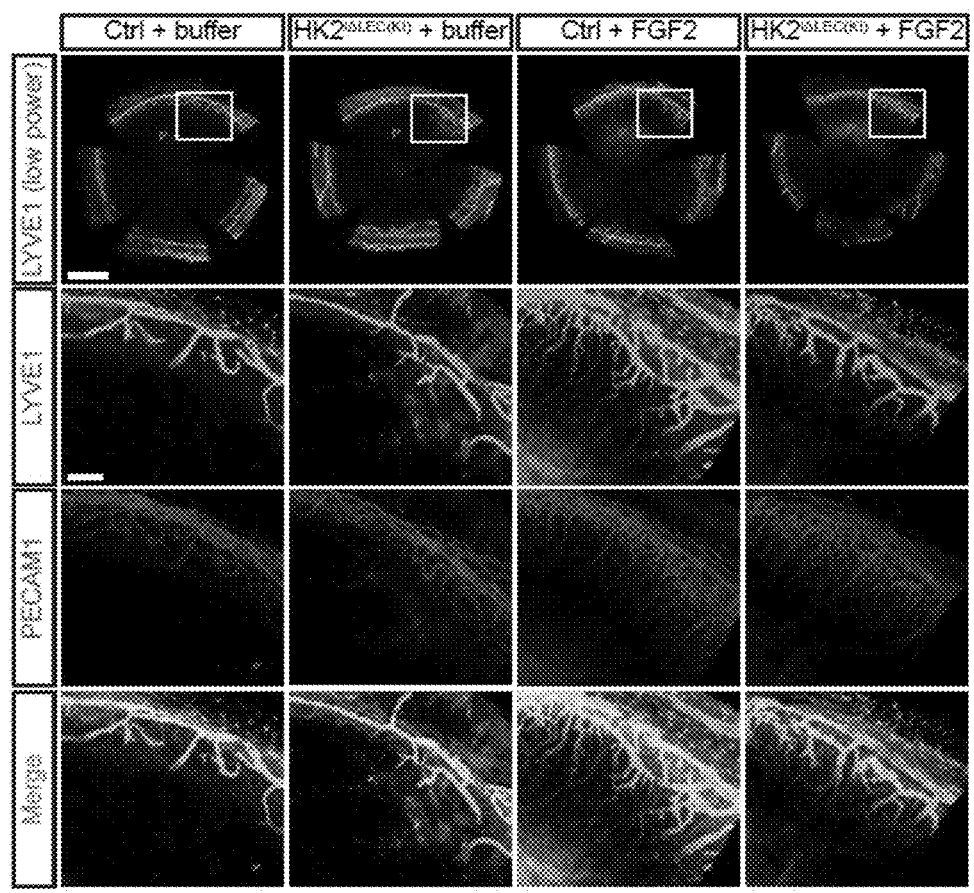
Figure 4I:
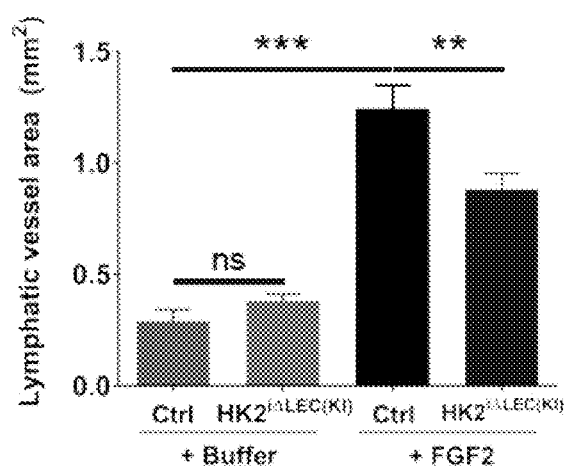

Next, the role played by HK2 in adult lymphangiogenesis was examined. Normal corneas in adult mice are devoid of both lymphatic and blood vasculature under normal conditions (Cao, R. et al. Nature protocols 6, 817-826, (2011)). Implantation of FGF2-containing pellets into the mouse cornea induced robust stimulation of lymphangiogenesis (FIGS. 4F-4H). Prox1-CreER$^{T2(KI)}$ (Srinivasan, R. S. et al., Genes Dev 21, 2422-2432, (2007)) is highly efficient in FGF2-induced corneal lymphatics as shown by analysis of Prox1-CreER$^{T2(KI)}$; mTmG reporter mice (FIG. 4G). Therefore, generated Prox1-CreER$^{T2(KI)}$; HK2$^{flox/flox}$ (referred to as HK2$^{i\Delta LEC(KI)}$) mice were generated and the Cre recombinase was activated in adult mice to bypass the early lymphatic defects caused by HK2 knockout. Examination of corneal lymphatics with staining for LYVE1 and PECAM1 showed that FGF2-induced lymphangiogenesis was significantly reduced in HK2$^{i\Delta LEC(KI)}$ compared with control mice (FIGS. 4H-4I).

Figure 18B:
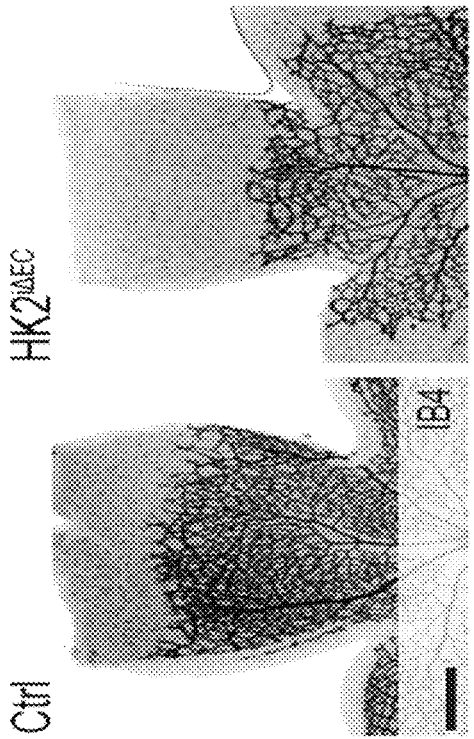
Figure 18A:
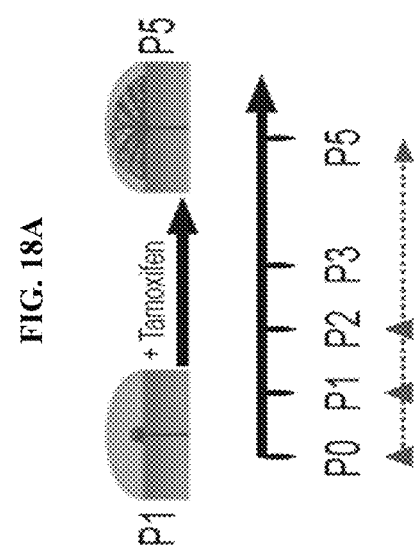
Figure 18C:
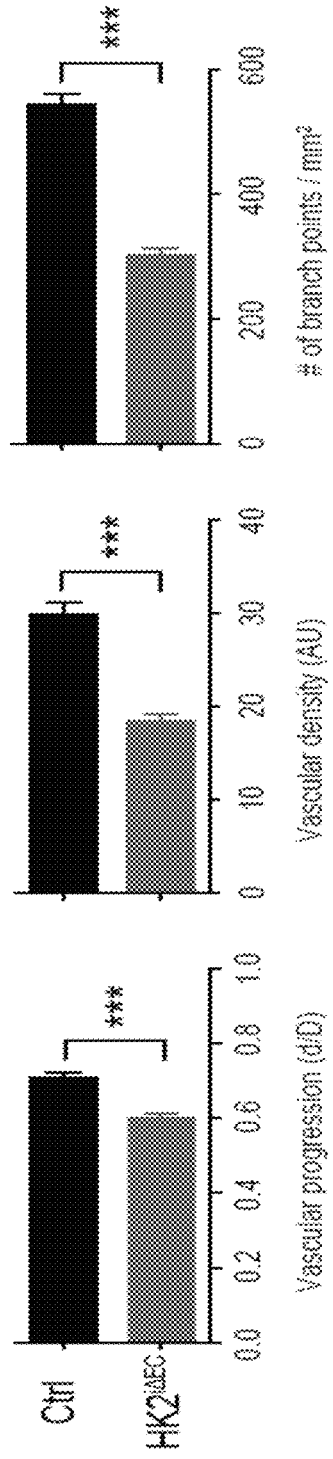

Similar to its role in the lymphatic development, pan-endothelial HK2 deletion at early developmental stage (E10.5) significantly reduced angiogenesis in the embryonic mouse skin (E15.5) (FIGS. 17A-17D). Arterial development and branching was also affected (FIGS. 12E-12F). Similar to the FGFR1/R3 data, activation of endothelial HK2 excision at P0 led to a significant reduction in the extent of development of the retinal vasculature including vascular progression, density and branching of the vascular tree (FIGS. 18A-18C). The number of tip cells was reduced (FIGS. 18D-18E) as was endothelial cell proliferation (FIGS. 18F-18G). No vascular regression defect was observed (FIGS. 13H-18I).

Example 4 c-Myc (Myc) Mediates FGF-Dependent Control of HK2 Expression

Given RNA-seq demonstration of FGF-dependent regulation of HK2 mRNA levels and a previous observation of Myc binding to the regulatory region of the HK2 gene in Burkitt's lymphoma cells (Kim, J. W. et al., Mol Cell Biol 27, 7381-7393, (2007)), it was examined whether Myc links FGF signaling to HK2 transcription in HDLECs. Chromatin Immunoprecipitation (ChIP) confirmed Myc binding to evolutionary conserved E-boxes in the first intron of the HK2 gene (FIGS. 19A-19B). Moreover, knockdown of Myc decreased, while its overexpression increased, HK2 mRNA levels (FIGS. 19C-19D). Importantly, Myc knockdown also decreased glycolysis, as evidenced by reduction in glycolytic flux (FIG. 19E) and extracellular acidification rate (ECAR) (FIG. 19F). Myc overexpression, on the other hand, increased glycolytic activity (FIG. 19G).

Figure 5A:
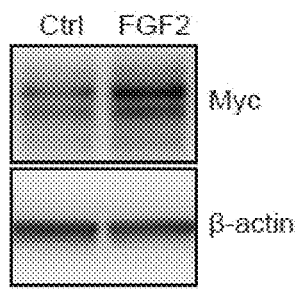
Figure 5B:
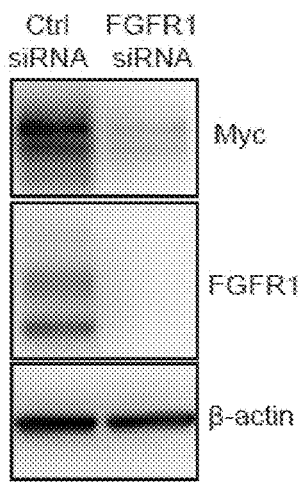
Figure 5C:
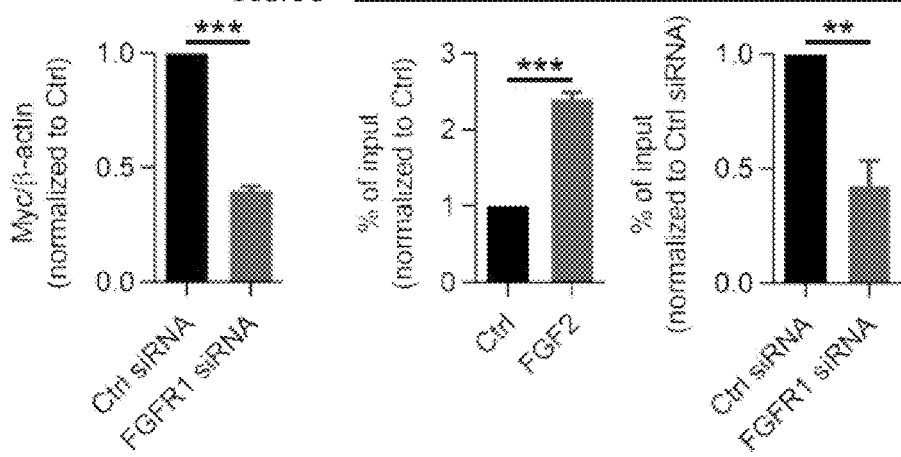
Figure 5D:
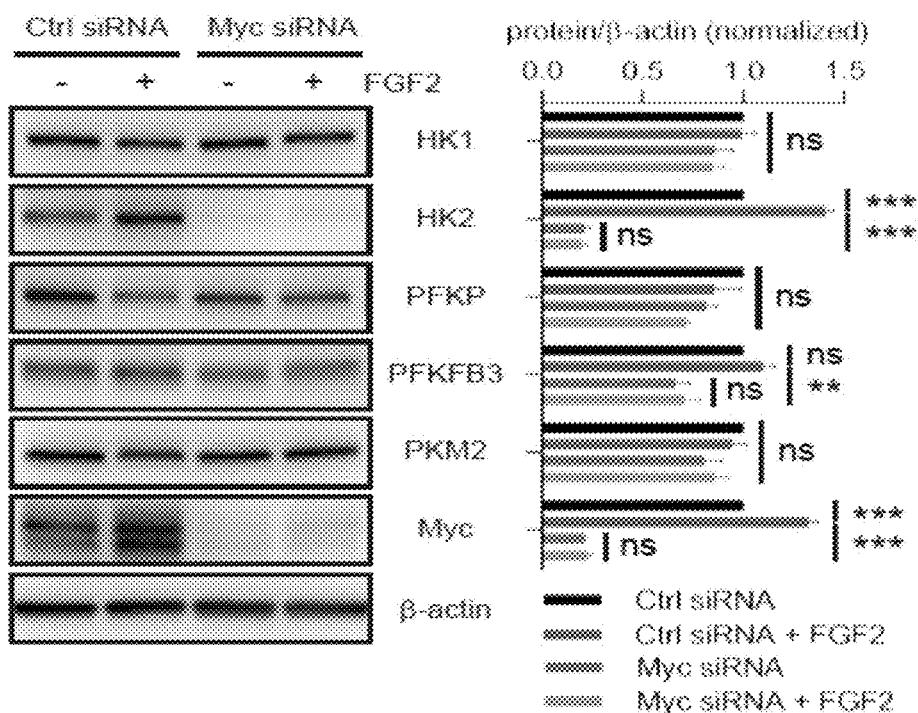
Figure 5E:
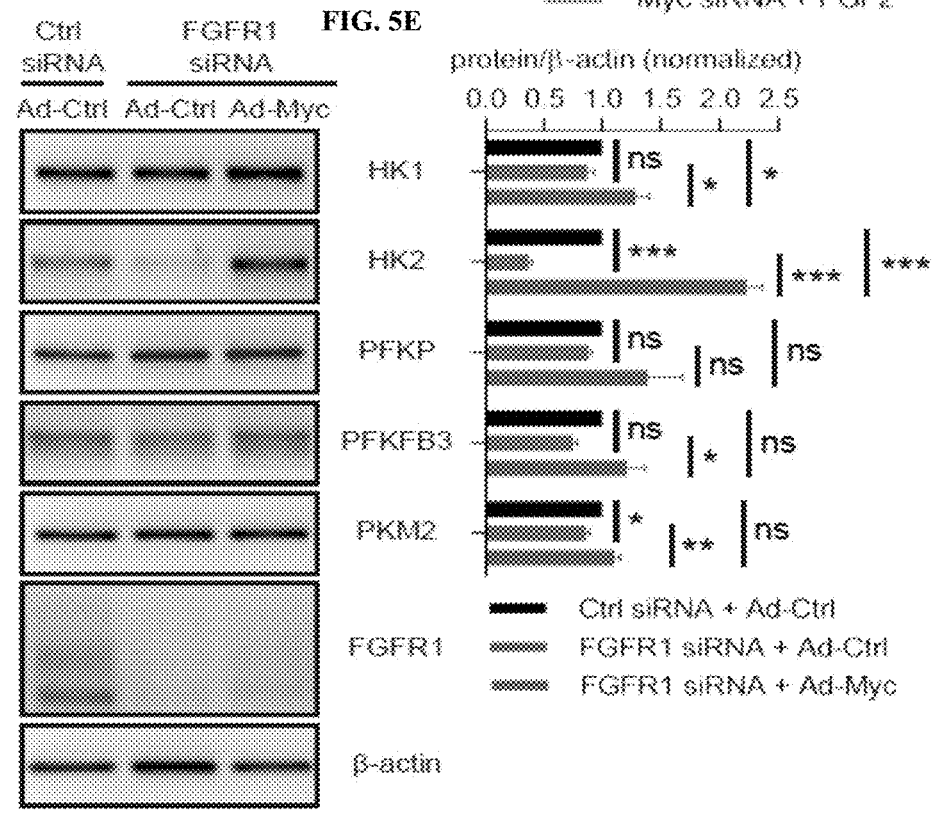

FGF2 treatment of HDLECs increased Myc protein expression (FIG. 5A) while FGFR1 knockdown reduced it (FIG. 5B). Furthermore, ChIP-quantitative PCR showed that the amount of Myc binding to the HK2 E-boxes was increased by FGF2 treatment and reduced by FGFR1 knockdown (FIG. 5C). Myc knockdown selectively reduced HK2 expression and prevented FGF2-induced increase in HK2 levels (FIG. 5D). Finally, the decrease in HK2 expression following FGFR1 knockdown was completely rescued by overexpression of Myc (FIG. 5E).

Figure 5F:
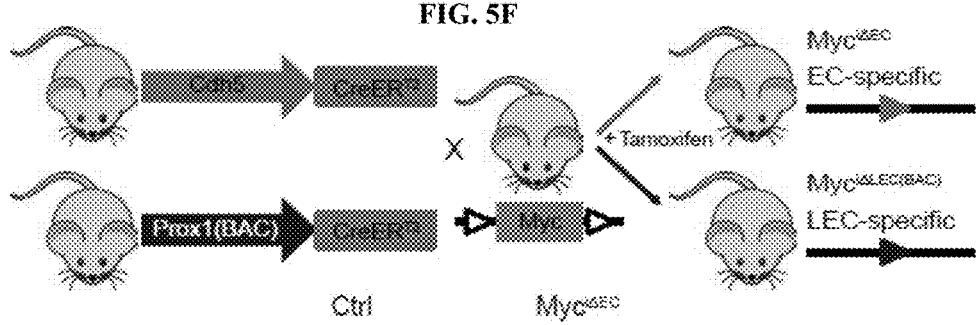
Figure 5G:
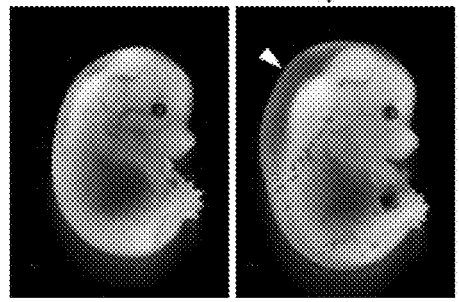
Figure 5H:
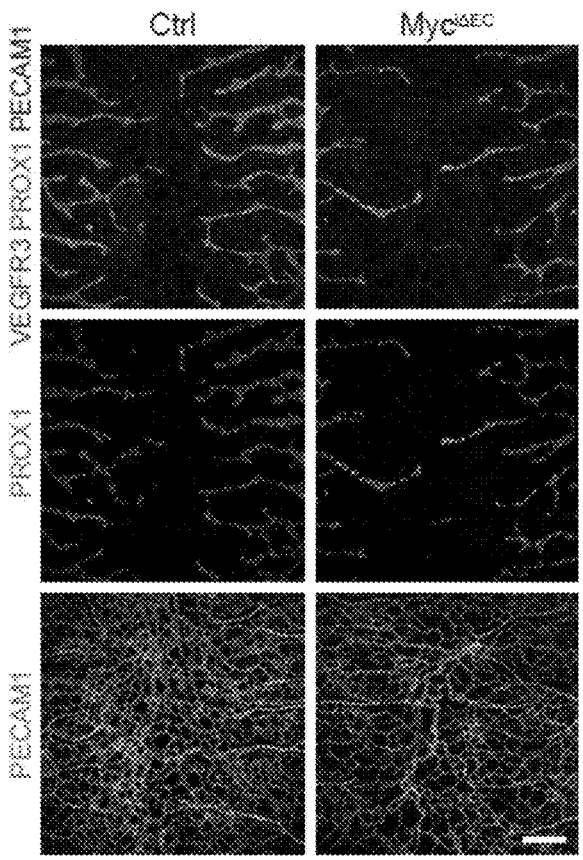

To confirm the role of Myc in lymphatic development, the lymphatic vasculature was examined in the anterior dorsal skin at E15.5 in Cdh5-CreER$^{T2}$; Myc$^{flox/flox}$ (Myc$^{i\Delta EC}$) mice following Cre activation at E11.5 (FIG. 5F). Similar to FGFR1/R3 and HK2 knockout mice, Myc$^{i\Delta EC}$ embryos exhibited significant edema (FIG. 5G) as well as a reduction in lymphatic vessels growth (FIGS. 5H-5J). Furthermore, LEC-specific Myc deletion using Prox1-CreER$^{T2(BAC)}$ (FIG. 5F) confirmed these findings (FIGS. 5K-5M).

Figure 20A:
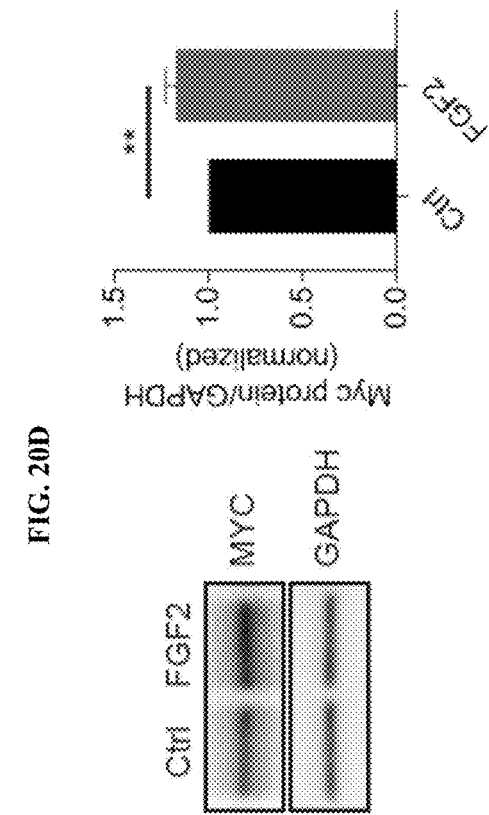
FIGS. 20A-20D are a series of images and graphs demonstrating that Myc regulates HK2 transcription and FGF2 treatment increases Myc expression in HUVECs.
Figure 20B:
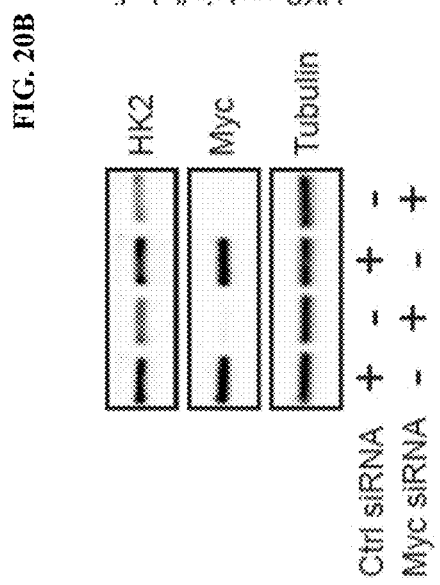
Figure 20C:
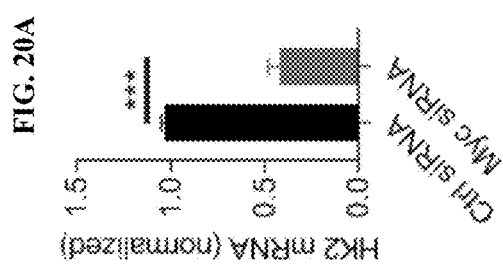
Figure 20D:
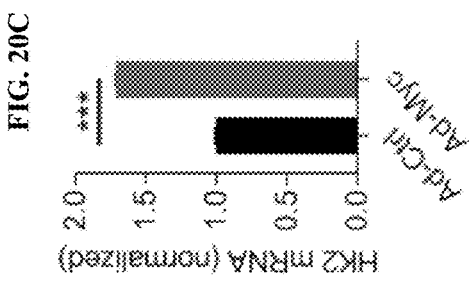
Figure 21A:
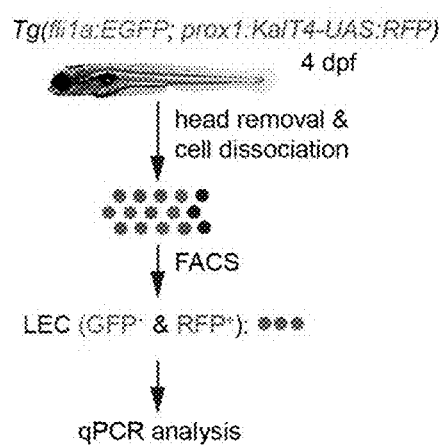
FIGS. 21A and 21B depict expression of FGFRs in zebrafish LECs.
Figure 21B:
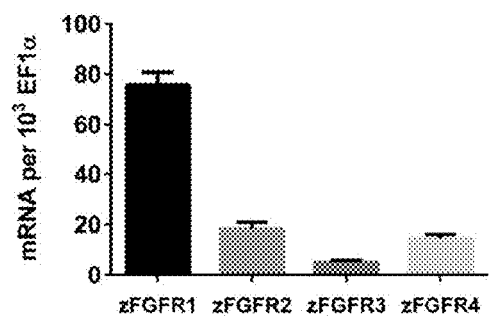
Figure 22A:
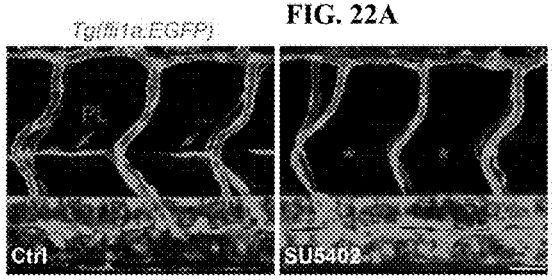
FIGS. 22A-22F depict chemical or genetic inhibition of FGF signaling impairs lymphatic development in zebrafish.
Figure 22B:
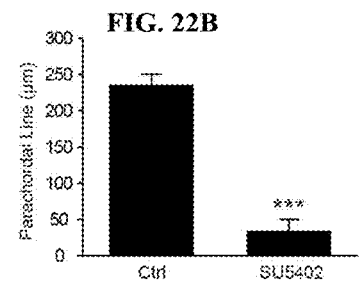
Figure 22C:
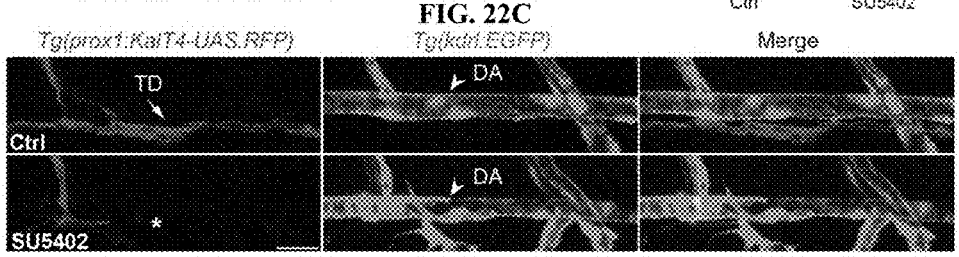
Figure 22D:
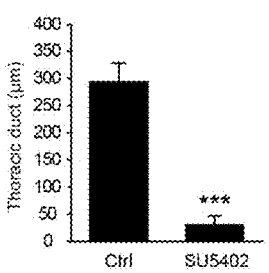
Figure 22E:
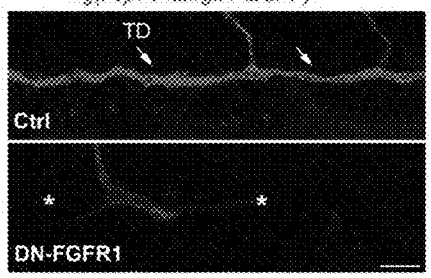
Figure 22F:
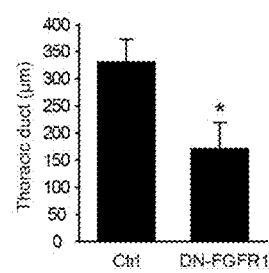
Figure 23A:
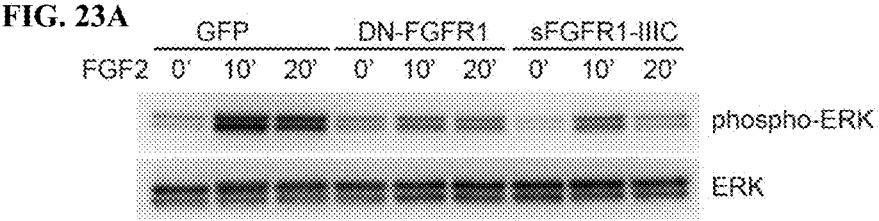
FIGS. 23A-23C depict FGF signaling blockade suppressing lymphatic development in the mouse tail skin.
Figure 23B:
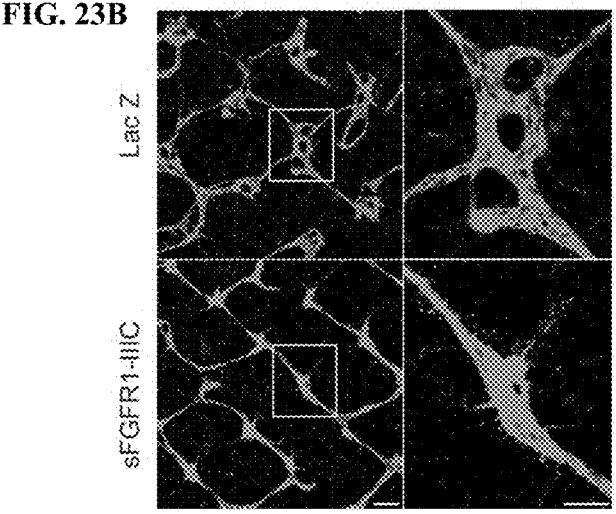
Figure 23C:
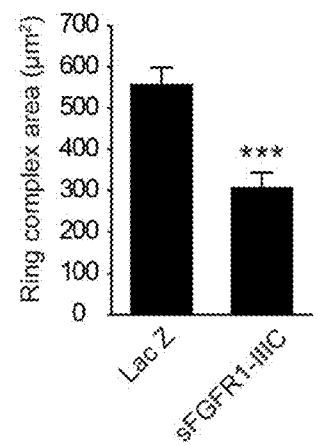

A previous study showed Myc involvement in blood vasculature development (Wilhelm, K. et al. Nature 529, 216-220, (2016)). In agreement with these findings, Myc knockdown in HUVECs reduced HK2 mRNA and protein expression (FIGS. 20A-20B). Furthermore, adenovirus-mediated overexpression of Myc enhanced HK2 expression (FIG. 20c). Finally, FGF2 treatment of HUVECs increased Myc expression (FIG. 20D). Collectively, these results suggest that FGF-dependent regulation of Myc expression underlies control of HK2 levels in LECs and BECs.

Example 5

These data indicate that FGF signaling plays a pivotal role in both blood and lymphatic vascular development by regulating events dependent on endothelial migration, sprouting and proliferation. Its loss in early embryonic development and neonatal stage affected blood vessel formation in the skin and in the retina, respectively. Pan-endothelial- and lymphatic-specific inhibition of FGF signaling led to similar lymphatic development defects. FGF signaling input was also required for lymphangiogenesis in adult tissues and tumors.

At the molecular level, FGFs control glycolysis via a Myc-dependent regulation of HK2 expression although additional regulation of the enzyme kinetics cannot be ruled out. FGF stimulation increased HK2 levels leading to induction of glycolysis and increased production of all key glycolytic metabolites, while its suppression had the opposite effect. The central role played by HK2 in this sequence of events is supported by several observations. First, among the key glycolytic enzymes only HK2 expression is affected by FGF signaling. Second, at the cellular level, effects of HK2 knockdown and overexpression mimicked those of FGF: increased HK2 expression, similar to FGF stimulation, increased LEC proliferation and migration while a HK2 knockdown, as well as FGFR1 knockdown, had the opposite effects. Third, HK2 overexpression partially rescued the effect of FGFR1 knockdown on LEC proliferation, migration and sprouting. Most importantly, mice with both pan-endothelial and LEC-specific knockouts of HK2 demonstrated vascular developmental defects very similar to those observed in FGFR1$^{i\Delta EC}$; $^{FGFR}3^{-/-}$ and FGFR1$^{i\Delta LEC(BAC)}$; FGFR3$^{-/-}$ mice. Finally, FGF2 was not able to induce lymphangiogenesis in HK2$^{i\Delta LEC(KI)}$ mice and an FGFR inhibitor blocked lymphatic growth in a mouse tumor model.

FGF achieves its control of HK2 expression in a Myc-dependent manner. The present data show that FGF regulates Myc expression in both blood and lymphatic endothelial cells. Furthermore, Myc directly binds to HK2 regulatory elements stimulating its transcription. Finally, pan-endothelium and lymphatic endothelium-specific knockout of Myc induces a phenotype closely resembling those seen in FGFR1$^{i\Delta EC}$; FGFR3$^{-/-}$, FGFR1$^{i\Delta LEC(BAC)}$; FGFR3$^{-/-}$, and HK2$^{i\Delta EC}$ as well as HK2$^{i\Delta LEC(BAC)}$ mice. This involvement of Myc in control of HK2 expression is in agreement with a recent report implicating it in regulation of vascular growth (Wilhelm, K. et al. Nature 529, 216-220, (2016)). These studies showed that Myc is highly expressed in sprouting blood vessels and that its deletion reduces glycolysis and proliferation. Thus, the FGF-Myc-HK2 axis is the crucial driver of glycolytic metabolism in the endothelium. The FGF/Myc/HK2-dependent regulation of vascular development is unexpected.

Vascular defects in FGFR1$^{i\Delta EC}$; FGFR3$^{-/-}$ mice were observed both in the systemic and lymphatic vasculatures. The two phenotypes are independent of each other as activation of a pan-endothelial Cdh5-CreER$^{T2}$ construct at later stages in development led to lymphatic development defects similar to those in lymphatic endothelium-specific knockout using Prox1-CreER$^{T2(BAC)}$. Yet the molecular mechanism is the same as FGF signaling input regulates HK2 expression in both blood and lymphatic endothelial cells and a pan-endothelial HK2 knockout affects both blood and lymphatic vasculatures.

In summary, FGF signaling regulates blood and lymphatic vascular development via control of endothelial metabolism driven by Myc-dependent regulation of HK2 expression. Therapeutic targeting of this FGF-Myc-HK2 pathway may open new possibilities for treatment of diseases associated with vascular growth.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating excessive vascular development associated with a cardiovascular disease in a subject in need thereof, the method comprising administering to the subject an effective amount of a hexokinase 2 (HK2) depleting agent that decreases the level of expression and/or activity of HK2 thereby decreasing the level of expression and/or activity of at least one selected from the group consisting of a fibroblast growth factor receptor (FGFR), a FGF ligand and FGF signaling, thereby treating the excessive vascular development in the subject, wherein the HK2 depleting agent targets an endothelial cell in the subject; and wherein the HK2 depleting agent directly targets HK2, wherein the HK2 depleting agent is selected from the group consisting of an antisense RNA, a siRNA, a shRNA, a ribozyme, an antisense molecule, an aptamer and any combination thereof.

2. The method of claim 1, wherein endothelial migration, sprouting and proliferation are reduced in the subject.

3. The method of claim 1, wherein the level or activity of the FGFR is decreased and the FGFR comprises FGFR1 and/or FGFR3.

4. The method of claim 1, wherein the vascular development comprises angiogenesis or lymphangiogenesis.

5. The method of claim 1, wherein the HK2 depleting agent is administered locally.

6. The method of claim 5, wherein the route of administration is selected from the group consisting of inhalation, oral, rectal, vaginal, parenteral, topical, transdermal, pulmonary, intranasal, buccal, ophthalmic, intrathecal, and any combination thereof.

7. The method of claim 1, wherein the excessive vascular development associated with a cardiovascular disease is associated with atherosclerosis.

8. A method for reducing or inhibiting vascular development associated with a cardiovascular disease in a subject in need thereof, the method comprising administering to the subject an effective amount of a hexokinase 2 (HK2) depleting agent in a pharmaceutical acceptable carrier, wherein the HK2 depleting agent targets an endothelial cell in the subject; and wherein the HK2 depleting agent directly targets HK2, wherein the HK2 depleting agent is selected from the group consisting of an antisense RNA, a siRNA, a shRNA, a ribozyme, an antisense molecule, an aptamer and any combination thereof.

9. The method of claim 8, wherein the HK2 depleting agent decreases the level of expression and/or activity of HK2.

10. The method of claim 8, wherein the HK2 depleting agent decreases the level of expression and/or activity of at least one selected from the group consisting of a fibroblast growth factor receptor (FGFR), a FGF ligand and FGF signaling, thereby treating or reducing vascular development.

11. The method of claim 10, wherein endothelial migration, sprouting and proliferation are reduced in the subject.

12. The method of claim 10, wherein the level or activity of the FGFR is decreased and the FGFR comprises FGFR1 and/or FGFR3.

13. The method of claim 8, wherein the HK2 depleting agent is administered locally.

14. The method of claim 8, wherein the route of administration is selected from the group consisting of inhalation, oral, rectal, vaginal, parenteral, topical, transdermal, pulmonary, intranasal, buccal, ophthalmic, intrathecal, and any combination thereof.

15. The method of claim 8, wherein the vascular development associated with a cardiovascular disease is associated with atherosclerosis.

* * * * *

```
SEQUENCE LISTING

<160> NUMBER OF SEQ ID NOS: 26

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
cggtacactc aatgacatcc ga                                              22

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ttcaccagga tgagtctgac c                                               21

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tgcaccacca actgcttagc                                                 20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
ggcatggact gtggtcatga g                                               21

<210> SEQ ID NO 5
<211> LENGTH: 21
<212> TYPE: DNA
<213> ORGANISM: Artificial Sequence
```

<220> FEATURE:
<223> OTHER INFORMATION: Primer

<400> SEQUENCE: 5
tggatgacaa gaggtttgac g                                              21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ggatggccag ggagaagtta g                                              21

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gtcaaactct cggagaacc                                                 19

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
tttctcagag gtgatgggt                                                 19

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
aggattggcc ttatccagg                                                 19

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
cagcttcctc tatctgccc                                                 19

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
gaggcagcca tgttccac                                                  18

```
<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tgccagactc cgtcagaact                                              20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
cagaggctgc catctaccac                                              20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ccagacttgg tgaggacgat                                              20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
tctgcattct cgcttcctgg                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
caggactcgt ttgtacccgt                                              20

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
gccccgcagg tagtcagg                                                18

<210> SEQ ID NO 18
<211> LENGTH: 19
<212> TYPE: DNA
<213> ORGANISM: Artificial Sequence
<220> FEATURE:
<223> OTHER INFORMATION: Primer
```

-continued

<400> SEQUENCE: 18
agccacgatt ctctccacg                                                    19

<210> SEQ ID NO 19
<211> LENGTH: 288
<212> TYPE: PRT
<213> ORGANISM: Homo sapiens

<400> SEQUENCE: 19

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 20
<211> LENGTH: 6774
<212> TYPE: DNA
<213> ORGANISM: Homo sapiens

<400> SEQUENCE: 20
cggccccaga aaacccgagc gagtaggggg cggcgcgcag gagggaggag aactgggggc      60
gcgggaggct ggtgggtgtg ggggtggag atgtagaaga tgtgacgccg cggcccggcg     120

-continued

```
ggtgccagat tagcggacgc ggtgcccgcg gttgcaacgg gatcccgggc gctgcagctt      180
gggaggcggc tctccccagg cggcgtccgc ggagacaccc atccgtgaac cccaggtccc      240
gggccgccgg ctcgccgcgc accaggggcc ggcggacaga gagcggccg agcggctcga       300 ggctggggga ccgcgggcgc ggccgcgcgc tgccgggcgg gaggctgggg ggccggggcc      360
ggggccgtgc cccggagcgg gtcggaggcc ggggccgggg ccggggacg gcggctcccc       420 gcgcggctcc agcggctcgg ggatcccggc cgggccccgc agggaccatg gcagccggga      480
gcatcaccac gctgcccgcc ttgcccgagg atggcggcag cggcgccttc ccgcccggcc      540
acttcaagga ccccaagcgg ctgtactgca aaaacggggg cttcttcctg cgcatccacc      600
ccgacggccg agttgacggg gtccgggaga gagcgaccc tcacatcaag ctacaacttc       660
aagcagaaga gagaggagtt gtgtctatca aggagtgtg tgctaaccgt tacctggcta       720
tgaaggaaga tggaagatta ctggcttcta aatgtgttac ggatgagtgt ttcttttttg      780
aacgattgga atctaataac tacaatactt accggtcaag gaaatacacc agttggtatg      840
tggcactgaa acgaactggg cagtataaac ttggatccaa acaggacct gggcagaaag       900 ctatacttt tcttccaatg tctgctaaga gctgatttta atggccacat ctaatctcat       960
ttcacatgaa agaagaagta tattttagaa atttgttaat gagagtaaaa gaaataaat     1020 gtgtatagct cagtttggat aattggtcaa acaatttttt atccagtagt aaaatatgta     1080
accattgtcc cagtaaagaa aaataacaaa agttgtaaaa tgtatattct ccctttata      1140 ttgcatctgc tgttacccag tgaagcttac ctagagcaat gatcttttc acgcatttgc      1200 tttattcgaa aagaggcttt taaaatgtgc atgtttagaa acaaaattc ttcatggaaa     1260 tcatatacat tagaaaatca cagtcagatg tttaatcaat ccaaaatgtc cactatttct     1320
tatgtcattc gttagtctac atgtttctaa acatataaat gtgaatttaa tcaattcctt     1380
tcatagtttt ataattctct ggcagttcct tatgatagag tttataaaac agtcctgtgt     1440
aaactgctgg aagttcttcc acagtcaggt caatttttgtc aaacccttct ctgtacccat    1500
acagcagcag cctagcaact ctgctggtga tgggagttgt attttcagtc ttcgccaggt     1560
cattgagatc catccactca catcttaagc attcttcctg gcaaaaattt atggtgaatg     1620
aatatggctt taggcggcag atgatataca tatctgactt cccaaaagct ccaggatttg     1680
tgtgctgttg ccgaatactc aggacggacc tgaattctga ttttatacca gtctcttcaa    1740
aaacttctcg aaccgctgtg tctcctacgt aaaaaaagag atgtacaaat caataataat     1800 tacacttta gaaactgtat catcaaagat tttcagttaa agtagcatta tgtaaaggct      1860
caaaacatta ccctaacaaa gtaaagtttt caatacaaat tctttgcctt gtggatatca     1920
agaaatccca aaatattttc ttaccactgt aaattcaaga agcttttgaa atgctgaata     1980
tttctttggc tgctacttgg aggcttatct acctgtacat ttttggggtc agctcttttt     2040
aacttcttgc tgctcttttt cccaaaaggt aaaaatatag attgaaaagt taaaacattt     2100
tgcatggctg cagttccttt gtttcttgag ataagattcc aaagaactta gattcatttc     2160
ttcaacaccg aaatgctgga ggtgtttgat cagttttcaa gaaacttgga atataaataa     2220
ttttataatt caacaaaggt tttcacattt tataaggttg attttcaat taaatgcaaa     2280 tttgtgtggc aggattttta ttgccattaa catatttttg tggctgcttt ttctacacat     2340
ccagatggtc cctctaactg ggctttctct aattttgtga tgttctgtca ttgtctccca     2400
aagtatttag gagaagccct ttaaaaagct gccttcctct accactttgc tggaaagctt    2460
cacaattgtc acagacaaag attttttgttc caatactcgt tttgcctcta ttttttcttgt   2520
```

```
ttgtcaaata gtaaatgata tttgcccttg cagtaattct actggtgaaa aacatgcaaa    2580
gaagaggaag tcacagaaac atgtctcaat tcccatgtgc tgtgactgta gactgtctta    2640
ccatagactg tcttacccat ccctggata tgctcttgtt ttttccctct aatagctatg     2700
gaaagatgca tagaaagagt ataatgtttt aaaacataag gcattcgtct gccattttttc   2760 aattacatgc tgacttccct tacaattgag atttgcccat aggttaaaca tggttagaaa    2820
caactgaaag cataaaagaa aaatctaggc cgggtgcagt ggctcatgcc tatattccct    2880
gcactttggg aggccaaagc aggaggatcg cttgagccca ggagttcaag accaacctgg    2940
tgaaaccccg tctctacaaa aaaacacaaa aaatagccag gcatggtggc gtgtacatgt    3000
ggtctcagat acttgggagg ctgaggtggg agggttgatc acttgaggct gagaggtcaa    3060
ggttgcagtg agccataatc gtgccactgc agtccagcct aggcaacaga gtgagacttt    3120
gtctcaaaaa aagagaaatt tccttaata agaaaagtaa ttttactct gatgtgcaat      3180 acatttgtta ttaaatttat tatttaagat ggtagcacta gtcttaaatt gtataaaata    3240 tccctaaca tgtttaaatg tccattttta ttcattatgc tttgaaaaat aattatgggg     3300
aaatacatgt ttgttattaa atttattatt aaagatagta gcactagtct taaatttgat    3360
ataacatctc ctaacttgtt taaatgtcca tttttattct ttatgtttga aaataaatta    3420
tggggatcct atttagctct tagtaccact aatcaaaagt tcggcatgta gctcatgatc    3480
tatgctgttt ctatgtcgtg gaagcaccgg atgggggtag tgagcaaatc tgccctgctc    3540
agcagtcacc atagcagctg actgaaaatc agcactgcct gagtagtttt gatcagttta    3600
acttgaatca ctaactgact gaaaattgaa tgggcaaata agtgcttttg tctccagagt    3660
atgcgggaga cccttccacc tcaagatgga tatttcttcc ccaaggattt caagatgaat    3720
tgaaattttt aatcaagata gtgtgctttta ttctgttgta ttttttatta ttttaatata   3780
ctgtaagcca aactgaaata acatttgctg tttataggt ttgaagaaca taggaaaaac    3840
taagaggttt tgttttattt tttgctgatg aagagatatg tttaaatatg ttgtattgtt   3900
ttgtttagtt acaggacaat aatgaaatgg agtttatatt tgttatttct attttgttat    3960
atttaataat agaattagat tgaaataaaa tataatggga aataatctgc agaatgtggg    4020
ttttcctggt gtttccctct gactctagtg cactgatgat ctctgataag gctcagctgc    4080
tttatagttc tctggctaat gcagcagata ctcttcctgc cagtggtaat acgatttttt    4140
aagaaggcag tttgtcaatt ttaatcttgt ggatacctttt atactcttag ggtattattt    4200
tatacaaaag ccttgaggat tgcattctat tttctatatg acccctcttga tatttaaaaa    4260 acactatgga taacaattct tcatttacct agtattatga agaatgaag gagttcaaac    4320 aaatgtgttt cccagttaac tagggtttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt ttcatttcta    4560
gctgctttca gggttttatg aatttttcagg caaagcttta atttatacta agcttaggaa    4620
gtatggctaa tgccaacggc agttttttttc ttccttaattc cacatgactg aggcatatat    4680
gatctctggg taggtgagtt gttgtgacaa ccacaagcac tttttttttt tttaagaaa    4740 aaaaggtagt gaatttttaa tcatctggac tttaagaagg attctggagt atacttaggc    4800
ctgaaattat atatatttgg cttggaaatg tgttttcctt caattacatc tacaagtaag    4860
```

| | | |
|---|---|---|
| tacagctgaa attcagagga cccataagag ttcacatgaa aaaaatcaat ttatttgaaa | 4920 |
| aggcaagatg caggagagag gaagccttgc aaacctgcag actgcttttt gcccaatata | 4980 |
| gattgggtaa ggctgcaaaa cataagctta attagctcac atgctctgct ctcacgtggc | 5040 |
| accagtggat agtgtgagag aattaggctg tagaacaaat ggccttctct ttcagcattc | 5100 |
| acaccactac aaaatcatct tttatatcaa cagaagaata agcataaact aagcaaaagg | 5160 |
| tcaataagta cctgaaacca agattggcta gagatatatc ttaatgcaat ccattttctg | 5220 |
| atggattgtt acgagttggc tatataatgt atgtatggta ttttgatttg tgtaaaagtt | 5280 |
| ttaaaaatca agctttaagt acatggacat ttttaaataa aatatttaaa gacaatttag | 5340 |
| aaaattgcct taatatcatt gttggctaaa tagaatagg gacatgcata ttaaggaaaa | 5400 |
| ggtcatggag aaataatatt ggtatcaaac aaatacattg atttgtcatg atacacattg | 5460 |
| aatttgatcc aatagtttaa ggaataggta ggaaaatttg gtttctattt ttcgatttcc | 5520 |
| tgtaaatcag tgacataaat aattcttagc ttattttata tttccttgtc ttaaatactg | 5580 |
| agctcagtaa gttgtgttag gggattattt ctcagttgag actttcttat atgacatttt | 5640 |
| actatgtttt gacttcctga ctattaaaaa taaatagtag atacaatttt cataaagtga | 5700 |
| agaattatat aatcactgct ttataactga ctttattata tttatttcaa agttcattta | 5760 |
| aaggctacta ttcatcctct gtgatggaat ggtcaggaat ttgttttctc atagtttaat | 5820 |
| tccaacaaca atattagtcg tatccaaaat aacctttaat gctaaacttt actgatgtat | 5880 |
| atccaaagct tctcattttc agacagatta atccagaagc agtcataaac agaagaatag | 5940 |
| gtggtatgtt cctaatgata ttatttctac taatggaata aactgtaata ttagaaatta | 6000 |
| tgctgctaat tatatcagct ctgaggtaat ttctgaaatg ttcagactca gtcggaacaa | 6060 |
| attggaaaat ttaaatttt attcttagct ataaagcaag aaagtaaaca cattaatttc | 6120 |
| ctcaacattt ttaagccaat taaaaatata aagatacac accaatatct tcttcaggct | 6180 |
| ctgacaggcc tcctggaaac ttccacatat ttttcaactg cagtataaag tcagaaaata | 6240 |
| aagttaacat aactttcact aacacacaca tatgtagatt tcacaaaatc cacctataat | 6300 |
| tggtcaaagt ggttgagaat atattttta gtaattgcat gcaaaatttt tctagcttcc | 6360 |
| atcctttctc cctcgtttct tctttttttg ggggagctgg taactgatga aatcttttcc | 6420 |
| caccttttct cttcaggaaa tataagtggt tttgttggt taacgtgata cattctgtat | 6480 |
| gaatgaaaca ttggagggaa acatctactg aatttctgta atttaaaata ttttgctgct | 6540 |
| agttaactat gaacagatag aagaatctta cagatgctgc tataaataag tagaaaatat | 6600 |
| aaatttcatc actaaaatat gctatttaa aatctatttc ctatattgta tttctaatca | 6660 |
| gatgtattac tcttattatt tctattgtat gtgttaatga ttttatgtaa aaatgtaatt | 6720 |
| gcttttcatg agtagtatga ataaaattga ttagtttgtg ttttcttgtc tccc | 6774 |

<210> SEQ ID NO 21
<211> LENGTH: 820
<212> TYPE: PRT
<213> ORGANISM: Homo sapiens

<400> SEQUENCE: 21

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly

```
                35                  40                  45
Asp Leu Leu Gln Leu Arg Cys Arg Leu Arg Asp Asp Val Gln Ser Ile
 50                  55                  60

Asn Trp Leu Arg Asp Gly Val Gln Leu Ala Glu Ser Asn Arg Thr Arg
 65                  70                  75                  80

Ile Thr Gly Glu Glu Val Glu Val Gln Asp Ser Val Pro Ala Asp Ser
                 85                  90                  95

Gly Leu Tyr Ala Cys Val Thr Ser Ser Pro Ser Gly Ser Asp Thr Thr
                100                 105                 110

Tyr Phe Ser Val Asn Val Ser Asp Ala Leu Pro Ser Ser Glu Asp Asp
                115                 120                 125

Asp Asp Asp Asp Asp Ser Ser Ser Glu Glu Lys Glu Thr Asp Asn Thr
                130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
                180                 185                 190

Asn Gly Lys Glu Phe Lys Pro Asp His Arg Ile Gly Gly Tyr Lys Val
                195                 200                 205

Arg Tyr Ala Thr Trp Ser Ile Ile Met Asp Ser Val Val Pro Ser Asp
                210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
                260                 265                 270

Val Glu Phe Met Cys Lys Val Tyr Ser Asp Pro Gln Pro His Ile Gln
                275                 280                 285

Trp Leu Lys His Ile Glu Val Asn Gly Ser Lys Ile Gly Pro Asp Asn
                290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
                340                 345                 350

Ser Ala Trp Leu Thr Val Leu Glu Ala Leu Glu Glu Arg Pro Ala Val
                355                 360                 365

Met Thr Ser Pro Leu Tyr Leu Glu Ile Ile Ile Tyr Cys Thr Gly Ala
                370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Ser Ala Asp Ser Ser
                420                 425                 430

Ala Ser Met Asn Ser Gly Val Leu Leu Val Arg Pro Ser Arg Leu Ser
                435                 440                 445

Ser Ser Gly Thr Pro Met Leu Ala Gly Val Ser Glu Tyr Glu Leu Pro
                450                 455                 460
```

```
Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
            485                 490                 495

Gly Leu Asp Lys Asp Lys Pro Asn Arg Val Thr Lys Val Ala Val Lys
        500                 505                 510

Met Leu Lys Ser Asp Ala Thr Glu Lys Asp Leu Ser Asp Leu Ile Ser
    515                 520                 525

Glu Met Glu Met Met Lys Met Ile Gly Lys His Lys Asn Ile Ile Asn
530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
        595                 600                 605

Met Glu Tyr Leu Ala Ser Lys Lys Cys Ile His Arg Asp Leu Ala Ala
610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
        675                 680                 685

Trp Glu Ile Phe Thr Leu Gly Gly Ser Pro Tyr Pro Gly Val Pro Val
690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
        755                 760                 765

Met Pro Leu Asp Gln Tyr Ser Pro Ser Phe Pro Asp Thr Arg Ser Ser
    770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 22
<211> LENGTH: 5895
<212> TYPE: DNA
<213> ORGANISM: Homo sapiens

<400> SEQUENCE: 22
agatgcaggg gcgcaaacgc caaaggagac caggctgtag gaagagaagg gcagagcgcc      60
```

```
ggacagctcg gcccgctccc cgtcctttgg ggccgcggct ggggaactac aaggcccagc      120
aggcagctgc aggggggcgga ggcggaggag ggaccagcgc gggtgggagt gagagagcga      180
gccctcgcgc cccgccggcg catagcgctc ggagcgctct tgcggccaca ggcgcggcgt      240
cctcggcggg gggcggcagc tagcgggagc cgggacgccg gtgcagccgc agcgcgcgga      300
ggaacccggg tgtgccggga gctgggcggc cacgtccgga cgggaccgag accctcgta       360 gcgcattgcg gcgacctcgc cttccccggc cgcgagcgcg ccgctgcttg aaaagccgcg      420
gaacccaagg acttttctcc ggtccgagct cggggcgccc cgcagggcgc acggtacccg      480
tgctgcagtc gggcacgccg cggcgccggg gcctccgcag ggcgatggag cccggtctgc      540
aaggaaagtg aggcgccgcc gctgcgttct ggaggagggg ggcacaaggt ctggagaccc      600
cgggtggcgg acgggagccc tccccccgcc ccgcctccgg ggcaccagct ccggctccat      660
tgttcccgcc cgggctggag gcgccgagca ccgagcgccg ccgggagtcg agcgccggcc      720
gcggagctct tgcgaccccg ccaggacccg aacagagccc gggggcggcg ggccggagcc      780
ggggacgcgg gcacacgccc gctcgcacaa gccacggcgg actctcccga ggcggaacct      840
ccacgccgag cgagggtcag tttgaaaagg aggatcgagc tcactgtgga gtatccatgg      900
agatgtggag ccttgtcacc aacctctaac tgcagaactg ggatgtggag ctggaagtgc      960
ctcctcttct gggctgtgct ggtcacagcc acactctgca ccgctaggcc gtccccgacc     1020
ttgcctgaac aagcccagcc ctggggagcc cctgtggaag tggagtcctt cctggtccac     1080
cccggtgacc tgctgcagct tcgctgtcgg ctgcgggacg atgtgcagag catcaactgg     1140
ctgcgggacg gggtgcagct ggcggaaagc aaccgcaccc gcatcacagg ggaggaggtg     1200
gaggtgcagg actccgtgcc cgcagactcc ggcctctatg cttgcgtaac cagcagcccc     1260
tcgggcagtg acaccaccta cttctccgtc aatgtttcag atgctctccc ctcctcggag     1320
gatgatgatg atgatgatga ctcctcttca gaggagaaag aaacagataa caccaaacca     1380
aaccgtatgc ccgtagctcc atattggaca tccccagaaa agatggaaaa gaaattgcat     1440
gcagtgccgg ctgccaagac agtgaagttc aaatgcccct tccagtgggac cccaaacccc     1500 acactgcgct ggttgaaaaa tggcaaagaa ttcaaacctg accacagaat tggaggctac     1560
aaggtccgtt atgccacctg gagcatcata atggactctg tggtgccctc tgacaagggc     1620
aactacacct gcattgtgga gaatgagtac ggcagcatca ccacacata ccagctggat      1680 gtcgtggagc ggtcccctca ccggcccatc ctgcaagcag ggttgcccgc caacaaaaca     1740
gtggccctgg gtagcaacgt ggagttcatg tgtaaggtgt acagtgaccc gcagccgcac     1800
atccagtggc taaagcacat cgaggtgaat gggagcaaga ttggcccaga caacctgcct     1860
tatgtccaga tcttgaagac tgctggagtt aataccaccg acaaagagat ggaggtgctt     1920
cacttaagaa atgtctcctt tgaggacgca ggggagtata cgtgcttggc gggtaactct     1980
atcggactct cccatcactc tgcatggttg accgttctgg aagccctgga agagaggccg     2040
gcagtgatga cctcgcccct gtacctggag atcatcatct attgcacagg ggccttcctc     2100
atctcctgca tggtggggtc ggtcatcgtc tacaagatga agagtggtac caagaagagt     2160
gacttccaca gccagatggc tgtgcacaag ctggccaaga gcatccctct gcgcagacag     2220
gtgtctgctg actccagtgc atccatgaac tctgggttc ttctggttcg gccatcacgg     2280
ctctcctcca gtgggactcc catgctagca ggggtctctg agtatgagct tcccgaagac     2340
cctcgctggg agctgcctcg ggacagactg gtcttaggca aacccctggg agagggctgc     2400
```

```
tttgggcagg tggtgttggc agaggctatc gggctggaca aggacaaacc caaccgtgtg    2460
accaaagtgg ctgtgaagat gttgaagtcg gacgcaacag agaaagactt gtcagacctg    2520
atctcagaaa tggagatgat gaagatgatc gggaagcata agaatatcat caacctgctg    2580
ggggcctgca cgcaggatgg tcccttgtat gtcatcgtgg agtatgcctc caagggcaac    2640
ctgcgggagt acctgcaggc ccggaggccc ccagggctgg aatactgcta caaccccagc    2700
cacaacccag aggagcagct ctcctccaag gacctggtgt cctgcgccta ccaggtggcc    2760
cgaggcatgg agtatctggc ctccaagaag tgcatacacc gagacctggc agccaggaat    2820
gtcctggtga cagaggacaa tgtgatgaag atagcagact ttggcctcgc acgggacatt    2880
caccacatcg actactataa aaagacaacc aacggccgac tgcctgtgaa gtggatggca    2940
cccgaggcat tatttgaccg gatctacacc accagagtg atgtgtggtc tttcggggtg    3000
ctcctgtggg agatcttcac tctgggcggc tccccatacc ccggtgtgcc tgtggaggaa    3060
cttttcaagc tgctgaagga gggtcaccgc atggacaagc ccagtaactg caccaacgag    3120
ctgtacatga tgatgcggga ctgctggcat gcagtgccct cacagagacc caccttcaag    3180
cagctggtgg aagacctgga ccgcatcgtg gccttgacct ccaaccagga gtacctggac    3240
ctgtccatgc cctggaccca gtactccccc agctttcccg acaccggag ctctacgtgc    3300 tcctcagggg aggattccgt cttctctcat gagccgctgc ccgaggagcc ctgcctgccc    3360
cgacacccag cccagcttgc caatggcgga ctcaaacgcc gctgactgcc acccacacgc    3420
cctccccaga ctccaccgtc agctgtaacc ctcacccaca gcccctgctg ggcccaccac    3480
ctgtccgtcc ctgtccccctt tcctgctggc aggagccggc tgcctaccag gggccttcct    3540
gtgtggcctg ccttcacccc actcagctca cctctccctc cacctcctct ccacctgctg    3600
gtgagaggtg caaagaggca gatctttgct gccagccact tcatcccctc ccagatgttg    3660
gaccaacacc cctccctgcc accaggcact gcctggaggg cagggagtgg gagccaatga    3720
acaggcatgc aagtgagagc ttcctgagct ttctcctgtc ggtttggtct gttttgcctt    3780 caccccataag cccctcgcac tctggtggca ggtgccttgt cctcagggct acagcagtag    3840
ggaggtcagt gcttcgtgcc tcgattgaag gtgacctctg ccccagatag gtggtgccag    3900
tggcttatta attccgatac tagtttgctt tgctgaccaa atgcctggta ccagaggatg    3960
gtgaggcgaa ggccaggttg ggggcagtgt tgtggccctg gggcccagcc ccaaactggg    4020
ggctctgtat atagctatga agaaaacaca aagtgtataa atctgagtat atatttacat    4080 gtcttttaa aagggtcgtt accagagatt tacccatcgg gtaagatgct cctggtggct    4140
gggaggcatc agttgctata tattaaaaac aaaaaagaaa aaaaggaaa atgttttaa    4200 aaaggtcata tattttttgc tacttttgct gttttatttt tttaaattat gttctaaacc    4260 tatttttcagt ttaggtccct caataaaaat tgctgctgct tcatttatct atgggctgta    4320
tgaaaagggt gggaatgtcc actggaaaga agggacaccc acgggccctg ggctaggtc    4380 tgtcccgagg gcaccgcatg ctcccggcgc aggttccttg taacctcttc ttcctaggtc    4440
ctgcacccag acctcacgac gcacctcctg cctctccgct gcttttggaa agtcagaaaa    4500
agaagatgtc tgcttcgagg gcaggaaccc catccatgca gtagaggcgc tgggcagaga    4560
gtcaaggccc agcagccatc gaccatggat ggtttcctcc aaggaaaccg gtggggttgg    4620
gctggggagg gggcacctac ctaggaatag ccacggggta gagctacagt gattaagagg    4680
aaagcaaggg cgcggttgct cacgcctgta atcccagcac tttgggacac cgaggtgggc    4740
agatcacttc aggtcaggag tttgagacca gcctggccaa cttagtgaaa ccccatctct    4800
```

-continued

```
actaaaaatg caaaaattat ccaggcatgg tggcacacgc ctgtaatccc agctccacag   4860
gaggctgagg cagaatccct tgaagctggg aggcggaggt tgcagtgagc cgagattgcg   4920
ccattgcact ccagcctggg caacagagaa acaaaaagg aaacaaatg atgaaggtct     4980 gcagaaactg aaacccagac atgtgtctgc cccctctatg tgggcatggt tttgccagtg   5040
cttctaagtg caggagaaca tgtcacctga ggctagtttt gcattcaggt ccctggcttc   5100
gtttcttgtt ggtatgcctc cccagatcgt ccttcctgta tccatgtgac cagactgtat   5160
ttgttgggac tgtcgcagat cttggcttct tacagttctt cctgtccaaa ctccatcctg   5220
tccctcagga acgggggaa aattctccga atgttttttgg ttttttggct gcttggaatt   5280
tacttctgcc acctgctggt catcactgtc ctcactaagt ggattctggc tccccgtac    5340 ctcatggctc aaactaccac tcctcagtcg ctatattaaa gcttatattt tgctggatta   5400
ctgctaaata caaagaaag ttcaatatgt tttcatttct gtagggaaaa tgggattgct    5460
gctttaaatt tctgagctag ggattttttg gcagctgcag tgttggcgac tattgtaaaa   5520
ttctctttgt ttctctctgt aaatagcacc tgctaacatt acaatttgta tttatgttta   5580
aagaaggcat catttggtga acagaactag gaaatgaatt tttagctctt aaaagcattt    5640
gctttgagac cgcacaggag tgtctttcct tgtaaaacag tgatgataat ttctgccttg   5700
gccctacctt gaagcaatgt tgtgtgaagg gatgaagaat ctaaaagtct tcataagtcc   5760
ttgggagagg tgctagaaaa atataaggca ctatcataat tacagtgatg tccttgctgt   5820
tactactcaa atcacccaca aatttcccca aagactgcgc tagctgtcaa ataaaagaca   5880
gtgaaattga cctga                                                    5895
```

<210> SEQ ID NO 23
<211> LENGTH: 806
<212> TYPE: PRT
<213> ORGANISM: Homo sapiens

<400> SEQUENCE: 23

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175
```

```
Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
                275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
            370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
                420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
            450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
            530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
                580                 585                 590
```

Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 24
<211> LENGTH: 4304
<212> TYPE: DNA
<213> ORGANISM: Homo sapiens

<400> SEQUENCE: 24
gtcgcgggca gctggcgccg cgcggtcctg ctctgccggt cgcacggacg caccggcggg     60
ccgccggccg gagggacggg gcgggagctg ggcccgcgga cagcgagccg gagcgggagc    120
cgcgcgtagc gagccgggct ccggcgctcg ccagtctccc gagcggcgcc cgcctcccgc    180
cggtgcccgc gccgggccgt gggggggcagc atgcccgcgc gcgctgcctg aggacgccgc    240
ggcccccgcc ccgccatggc gcgccctgc ctgcgccctc gcgctctgcg tggccgtggc    300
catcgtggcc ggcgcctcct cggagtcctt ggggacggag cagcgcgtcg tggggcgagc    360
ggcagaagtc ccgggcccag agcccggcca gcaggagcag ttggtcttcg gcagcgggga    420
tgctgtggag ctgagctgtc cccgccggg ggtggtccc atgggggccca ctgtctgggt    480 caaggatggc acagggctgg tgccctcgga gcgtgtcctg gtgggccccc agcggctgca    540
ggtgctgaat gcctcccacg aggactccgg ggcctacagc tgccggcagc ggctcacgca    600
gcgcgtactg tgccacttca gtgtgcgggt gacagacgct ccatcctcgg agatgacga    660 agacggggag gacgaggctg aggacacagg tgtggacaca ggggccccctt actggacacg    720 gcccgagcgg atggacaaga agctgctggc cgtgccggcc gccaacaccg tccgcttccg    780
ctgcccagcc gctggcaacc ccactccctc catctcctgg ctgaagaacg cagggagtt    840 ccgcggcgag caccgcattg gaggcatcaa gctgcggcat cagcagtgga gcctggtcat    900

```
ggaaagcgtg gtgccctcgg accgcggcaa ctacacctgc gtcgtggaga acaagtttgg    960
cagcatccgg cagacgtaca cgctggacgt gctggacgc tccccgcacc ggcccatcct   1020
gcaggcgggg ctgccggcca accagacggc ggtgctgggc agcgacgtgg agttccactg   1080
caaggtgtac agtgacgcac agccccacat ccagtggctc aagcacgtgg aggtgaatgg   1140
cagcaaggtg ggcccggacg gcacacccta cgttaccgtg ctcaagacgg cgggcgctaa   1200
caccaccgac aaggagctag aggttctctc cttgcacaac gtcacctttg aggacgccgg   1260
ggagtacacc tgcctggcgg gcaattctat tgggttttct catcactctg cgtggctggt   1320
ggtgctgcca gccgaggagg agctggtgga ggctgacgag gcgggcagtg tgtatgcagg   1380
catcctcagc tacggggtgg gcttcttcct gttcatcctg gtggtggcgg ctgtgacgct   1440
ctgccgcctg cgcagccccc ccaagaaagg cctgggctcc ccaccgtgc acaagatctc   1500
ccgcttcccg ctcaagcgac aggtgtccct ggagtccaac gcgtccatga gctccaacac   1560
accactggtg cgcatcgcaa ggctgtcctc aggggagggc cccacgctgg ccaatgtctc   1620
cgagctcgag ctgcctgccg accccaaatg ggagctgtct cgggcccggc tgaccctggg   1680
caagcccctt ggggagggct gcttcggcca ggtggtcatg gcggaggcca tcggcattga   1740
caaggaccgg gccgccaagc ctgtcaccgt agccgtgaag atgctgaaag acgatgccac   1800
tgacaaggac ctgtcggacc tggtgtctga gatggagatg atgaagatga tcgggaaaca   1860
caaaaacatc atcaacctgc tgggcgcctg cacgcagggc gggcccctgt acgtgctggt   1920
ggagtacgcg gccaagggta acctgcggga gtttctgcgg gcgcggcggc ccccgggcct   1980
ggactactcc ttcgacacct gcaagccgcc cgaggagcag ctcaccttca aggacctggt   2040
gtcctgtgcc taccaggtgg cccgggggcat ggagtacttg gcctcccaga agtgcatcca   2100
cagggacctg gctgcccgca atgtgctggt gaccgaggac aacgtgatga agatcgcaga   2160
cttcgggctg gccgggacg tgcacaacct cgactactac aagaagacaa ccaacggccg   2220
gctgccgtg aagtggatgg cgcctgaggc cttgtttgac cgagtctaca ctcaccagag   2280
tgacgtctgg tcctttgggg tcctgctctg ggagatcttc acgctggggg gctccccgta   2340
ccccggcatc cctgtggagg agctcttcaa gctgctgaag gagggccacc gcatggacaa   2400
gcccgccaac tgcacacacg acctgtacat gatcatgcgg gagtgctggc atgccgcgcc   2460
ctcccagagg cccaccttca gcagctggt ggaggacctg accgtgtcc ttaccgtgac   2520
gtccaccgac gagtacctgg acctgtcggc gcctttcgag cagtactccc cgggtggcca   2580
ggacaccccc agctccagct cctcagggga cgactccgtg tttgcccacg acctgctgcc   2640
cccggcccca cccagcagtg ggggctcgcg gacgtgaagg gccactggtc cccaacaatg   2700
tgagggtcc ctagcagccc accctgctgc tggtgcacag ccactccccg gcatgagact   2760
cagtgcagat ggagagacag ctacacagag cttggtctg tgtgtgtgtg tgtgcgtgtg   2820
tgtgtgtgtg tgtgcacatc cgcgtgtgcc tgtgtgcgtg cgcatcttgc ctccaggtgc   2880
agaggtaccc tgggtgtccc cgctgctgtg caacggtctc ctgactggtg ctgcagcacc   2940
gaggggcctt tgttctgggg ggacccagtg cagaatgtaa gtgggcccac ccggtgggac   3000
ccccgtgggg cagggagctg ggcccgacat ggctccggcc tctgcctttg caccacggga   3060
catcacaggg tgggcctcgg cccctcccac acccaaagct gagcctgcag ggaagcccca   3120
catgtccagc accttgtgcc tggggtgtta gtggcaccgc ctccccacct ccaggctttc   3180
ccacttccca ccctgcccct cagagactga aattacgggt acctgaagat gggagccttt   3240
```

-continued

```
accttttatg caaaaggttt attccggaaa ctagtgtaca tttctataaa tagatgctgt    3300
gtatatggta tatatacata tatatatata acatatatgg aagaggaaaa ggctggtaca    3360
acggaggcct gcgaccctgg gggcacagga ggcaggcatg gccctgggcg gggcgtgggg    3420
gggcgtggag ggaggcccca gggggtctca cccatgcaag cagaggacca gggccttttc    3480
tggcaccgca gttttgtttt aaaactggac ctgtatattt gtaaagctat ttatgggccc    3540
ctggcactct tgttcccaca ccccaacact tccagcattt agctggccac atggcggaga    3600
gttttaattt ttaacttatt gacaaccgag aaggtttatc ccgccgatag agggacggcc    3660
aagaatgtac gtccagcctg ccccggagct ggaggatccc ctccaagcct aaaaggttgt    3720
taatagttgg aggtgattcc agtgaagata ttttatttcc tttgtccttt ttcaggagaa    3780
ttagatttct ataggatttt tctttaggag atttattttt tggacttcaa agcaagctgg    3840
tattttcata caaattcttc taattgctgt gtgtcccagg cagggagacg gtttccaggg    3900
aggggccggc cctgtgtgca ggttccgatg ttattagatg ttacaagttt atatatatct    3960
atatatataa tttattgagt ttttacaaga tgtatttgtt gtagacttaa cacttcttac    4020
gcaatgcttc tagagtttta tagcctggac tgctaccttt caaagcttgg agggaagccg    4080
tgaattcagt tggttcgttc tgtactgtta ctgggccctg agtctgggca gctgtccctt    4140
gcttgcctgc agggccatgg ctcagggtgg tctcttcttg gggcccagtg catggtggcc    4200
agaggtgtca cccaaaccgg caggtgcgat tttgttaacc cagcgacgaa ctttccgaaa    4260
aataaagaca cctggttgct aacctggaaa aaaaaaaaa aaaa                      4304
```

<210> SEQ ID NO 25
<211> LENGTH: 917
<212> TYPE: PRT
<213> ORGANISM: Homo sapiens

<400> SEQUENCE: 25

```
Met Ile Ala Ser His Leu Leu Ala Tyr Phe Phe Thr Glu Leu Asn His
1               5                   10                  15

Asp Gln Val Gln Lys Val Asp Gln Tyr Leu Tyr His Met Arg Leu Ser
                20                  25                  30

Asp Glu Thr Leu Leu Glu Ile Ser Lys Arg Phe Arg Lys Glu Met Glu
            35                  40                  45

Lys Gly Leu Gly Ala Thr Thr His Pro Thr Ala Ala Val Lys Met Leu
        50                  55                  60

Pro Thr Phe Val Arg Ser Thr Pro Asp Gly Thr Glu His Gly Glu Phe
65                  70                  75                  80

Leu Ala Leu Asp Leu Gly Gly Thr Asn Phe Arg Val Leu Trp Val Lys
                85                  90                  95

Val Thr Asp Asn Gly Leu Gln Lys Val Glu Met Glu Asn Gln Ile Tyr
            100                 105                 110

Ala Ile Pro Glu Asp Ile Met Arg Gly Ser Gly Thr Gln Leu Phe Asp
        115                 120                 125

His Ile Ala Glu Cys Leu Ala Asn Phe Met Asp Lys Leu Gln Ile Lys
    130                 135                 140

Asp Lys Lys Leu Pro Leu Gly Phe Thr Phe Ser Phe Pro Cys His Gln
145                 150                 155                 160

Thr Lys Leu Asp Glu Ser Phe Leu Val Ser Trp Thr Lys Gly Phe Lys
                165                 170                 175

Ser Ser Gly Val Glu Gly Arg Asp Val Val Ala Leu Ile Arg Lys Ala
            180                 185                 190
```

```
Ile Gln Arg Arg Gly Asp Phe Asp Ile Asp Ile Val Ala Val Val Asn
        195                 200                 205

Asp Thr Val Gly Thr Met Met Thr Cys Gly Tyr Asp Asp His Asn Cys
    210                 215                 220

Glu Ile Gly Leu Ile Val Gly Thr Gly Ser Asn Ala Cys Tyr Met Glu
225                 230                 235                 240

Glu Met Arg His Ile Asp Met Val Glu Gly Asp Glu Gly Arg Met Cys
                245                 250                 255

Ile Asn Met Glu Trp Gly Ala Phe Gly Asp Asp Gly Ser Leu Asn Asp
                260                 265                 270

Ile Arg Thr Glu Phe Asp Gln Glu Ile Asp Met Gly Ser Leu Asn Pro
            275                 280                 285

Gly Lys Gln Leu Phe Glu Lys Met Ile Ser Gly Met Tyr Met Gly Glu
        290                 295                 300

Leu Val Arg Leu Ile Leu Val Lys Met Ala Lys Glu Glu Leu Leu Phe
305                 310                 315                 320

Gly Gly Lys Leu Ser Pro Glu Leu Leu Asn Thr Gly Arg Phe Glu Thr
                325                 330                 335

Lys Asp Ile Ser Asp Ile Glu Gly Glu Lys Asp Gly Ile Arg Lys Ala
                340                 345                 350

Arg Glu Val Leu Met Arg Leu Gly Leu Asp Pro Thr Gln Glu Asp Cys
            355                 360                 365

Val Ala Thr His Arg Ile Cys Gln Ile Val Ser Thr Arg Ser Ala Ser
        370                 375                 380

Leu Cys Ala Ala Thr Leu Ala Ala Val Leu Gln Arg Ile Lys Glu Asn
385                 390                 395                 400

Lys Gly Glu Glu Arg Leu Arg Ser Thr Ile Gly Val Asp Gly Ser Val
                405                 410                 415

Tyr Lys Lys His Pro His Phe Ala Lys Arg Leu His Lys Thr Val Arg
                420                 425                 430

Arg Leu Val Pro Gly Cys Asp Val Arg Phe Leu Arg Ser Glu Asp Gly
            435                 440                 445

Ser Gly Lys Gly Ala Ala Met Val Thr Ala Val Ala Tyr Arg Leu Ala
        450                 455                 460

Asp Gln His Arg Ala Arg Gln Lys Thr Leu Glu His Leu Gln Leu Ser
465                 470                 475                 480

His Asp Gln Leu Leu Glu Val Lys Arg Arg Met Lys Val Glu Met Glu
                485                 490                 495

Arg Gly Leu Ser Lys Glu Thr His Ala Ser Ala Pro Val Lys Met Leu
                500                 505                 510

Pro Thr Tyr Val Cys Ala Thr Pro Asp Gly Thr Glu Lys Gly Asp Phe
            515                 520                 525

Leu Ala Leu Asp Leu Gly Gly Thr Asn Phe Arg Val Leu Leu Val Arg
530                 535                 540

Val Arg Asn Gly Lys Trp Gly Gly Val Glu Met His Asn Lys Ile Tyr
545                 550                 555                 560

Ala Ile Pro Gln Glu Val Met His Gly Thr Gly Asp Glu Leu Phe Asp
                565                 570                 575

His Ile Val Gln Cys Ile Ala Asp Phe Leu Glu Tyr Met Gly Met Lys
                580                 585                 590

Gly Val Ser Leu Pro Leu Gly Phe Thr Phe Ser Phe Pro Cys Gln Gln
            595                 600                 605
```

Asn Ser Leu Asp Glu Ser Ile Leu Leu Lys Trp Thr Lys Gly Phe Lys
610                 615                 620

Ala Ser Gly Cys Glu Gly Glu Asp Val Val Thr Leu Leu Lys Glu Ala
625                 630                 635                 640

Ile His Arg Arg Glu Glu Phe Asp Leu Asp Val Val Ala Val Val Asn
            645                 650                 655

Asp Thr Val Gly Thr Met Met Thr Cys Gly Phe Glu Asp Pro His Cys
            660                 665                 670

Glu Val Gly Leu Ile Val Gly Thr Gly Ser Asn Ala Cys Tyr Met Glu
            675                 680                 685

Glu Met Arg Asn Val Glu Leu Val Glu Gly Glu Glu Gly Arg Met Cys
690                 695                 700

Val Asn Met Glu Trp Gly Ala Phe Gly Asp Asn Gly Cys Leu Asp Asp
705                 710                 715                 720

Phe Arg Thr Glu Phe Asp Val Ala Val Asp Glu Leu Ser Leu Asn Pro
                725                 730                 735

Gly Lys Gln Arg Phe Glu Lys Met Ile Ser Gly Met Tyr Leu Gly Glu
                740                 745                 750

Ile Val Arg Asn Ile Leu Ile Asp Phe Thr Lys Arg Gly Leu Leu Phe
            755                 760                 765

Arg Gly Arg Ile Ser Glu Arg Leu Lys Thr Arg Gly Ile Phe Glu Thr
770                 775                 780

Lys Phe Leu Ser Gln Ile Glu Ser Asp Cys Leu Ala Leu Leu Gln Val
785                 790                 795                 800

Arg Ala Ile Leu Gln His Leu Gly Leu Glu Ser Thr Cys Asp Asp Ser
                805                 810                 815

Ile Ile Val Lys Glu Val Cys Thr Val Val Ala Arg Arg Ala Ala Gln
                820                 825                 830

Leu Cys Gly Ala Gly Met Ala Ala Val Val Asp Arg Ile Arg Glu Asn
            835                 840                 845

Arg Gly Leu Asp Ala Leu Lys Val Thr Val Gly Val Asp Gly Thr Leu
850                 855                 860

Tyr Lys Leu His Pro His Phe Ala Lys Val Met His Glu Thr Val Lys
865                 870                 875                 880

Asp Leu Ala Pro Lys Cys Asp Val Ser Phe Leu Gln Ser Glu Asp Gly
                885                 890                 895

Ser Gly Lys Gly Ala Ala Leu Ile Thr Ala Val Ala Cys Arg Ile Arg
                900                 905                 910

Glu Ala Gly Gln Arg
        915

<210> SEQ ID NO 26
<211> LENGTH: 7109
<212> TYPE: DNA
<213> ORGANISM: Homo sapiens

<400> SEQUENCE: 26
tggattatga tttttgttta tttttcctgt ttatccatat attattttc aacaatgagt      60 attgattact tatataataa ttttaaggct gtacacattg cagacagcac cccactgttt     120
gaaaaactcc tcctcagtag aacatggcag accttcatct tccttccctg aacctttcc     180 aaccttaggc ttgccattct ccaccagtgc taatgtcatg tctcttgaaa tctgtattga     240
agtcagtatt tcattcttgc cagtttccac tgtgtgttta aatttggagt ctggtgtcta     300
gcattagctg gggttggagc ttccactcct ctcagcattg gtaagcctcc tcacccaccc     360

| | | | | | |
|---|---|---|---|---|---|
| catcccatgt | ccaagatcac | ccagttacac | acttaccatc | tacccagttc | attcacatca | 420 |
| tcagtcccag | agctgcagag | atgctctttt | tctacctcct | acttctctgg | ctcttagaga | 480 |
| ggcagcatgg | gataatgggg | caagcgaata | gggccttaaa | gtagagggac | aagggttctc | 540 |
| ttccctatct | gccacttatt | agctatgtga | cctcgtgtaa | gtctcttttc | tttttgagac | 600 |
| agggtctccc | tctgtcacct | aggctggagt | acagtggtat | gatcatagct | cactgcagcc | 660 |
| tcgaactcct | gggctcaagc | tatccttcca | ccttagcctt | ctgagcagca | ggactacag | 720 |
| gcacatgcca | ccatgtccgg | ctgatttatt | tatttttatt | tgggaagatg | ggggtctcac | 780 |
| tatgtcgccc | aggctggtca | tgaactcctg | gtctcaagca | accctccaac | cttggactcc | 840 |
| caaagtgctg | ggattacagg | tgtgagccct | ggccttgcct | caatttcctc | atctgtaaaa | 900 |
| cggggttagt | gaaactcaca | tcctatcagt | ggttttgagg | atgggccgac | tcttgtattg | 960 |
| cctgctctag | tacaatcagc | agctaaggcg | gctcactttc | cggccgtgct | acaataggta | 1020 |
| agaactagga | tgctttagac | gtgtgactgg | gcagtgggag | cccctcacat | gatcccgaga | 1080 |
| tgccagacag | tgtctctccg | cacagggcgt | gtgctggtcc | agaggcccgt | ttttccagtc | 1140 |
| gccccacacc | ccgggtccgc | gatcacgctc | cccccaccca | tagccgagcc | tgacgcggcg | 1200 |
| gtggctcatg | cgcctttccg | tcccagcctt | tagccacgga | ccacacgtcc | catctcaggc | 1260 |
| gccccgcccc | tccccgccc | ccgcccccg | gcgcgcctcc | ccaggctgcc | ggctccggtg | 1320 |
| tctgagcggc | cgcgcccgcg | agccgtgagc | gatgattggc | tgcgccacgg | cggcgggcgg | 1380 |
| tccgtgggcg | cacacaccct | ccccgcgcag | ccaatgggcg | tgcgcacgtc | actgatccgg | 1440 |
| aggcccgcgg | gccggcagcc | cctcaataag | ccacattgtt | gcatgaaact | ccggcgcagg | 1500 |
| agtcccgggc | tgccgctggc | aacatcgtgt | cacccagcta | agaaaatccg | cgggcccgag | 1560 |
| ccacgcgcct | gtgaatcgga | gaggtcccac | tgcccgagtg | gagccgggct | gagattcttc | 1620 |
| tcaagttgag | cctcagtgat | cctgtggccg | aagttagcgc | cttgacgtgg | gacaaccgga | 1680 |
| cacgtcgcca | ggagagaact | gaggcgcctt | ctagcagttg | tgacgccaaa | atcacgtctc | 1740 |
| cggagacccg | cgcccctccgc | cagccgggcg | caccctcgcc | ggtagccttc | tttgtgcgcc | 1800 |
| gtccggactc | ccagctcccg | gcccggcagc | cgagccccag | cacaaagcag | tcggaccgcg | 1860 |
| ccgcccgcct | cccctctcgc | gtctccgcct | cggtttccca | actctgcgcc | gtcgggccgc | 1920 |
| ggcaggatga | ttgcctcgca | tctgcttgcc | tacttcttca | cggagctcaa | ccatgaccaa | 1980 |
| gtgcagaagg | ttgaccagta | tctctaccac | atgcgcctct | ctgatgagac | cctcttggag | 2040 |
| atctctaagc | ggttccgcaa | ggagatggag | aaagggcttg | gagccaccac | tcaccctact | 2100 |
| gcagcagtga | agatgctgcc | cacctttgtg | aggtccactc | cagatgggac | agaacacgga | 2160 |
| gagttcctgg | ctctggatct | tggagggacc | aacttccgtg | tgctttgggt | gaaagtaacg | 2220 |
| gacaatgggc | tccagaaggt | ggagatggag | aatcagatct | atgccatccc | tgaggacatc | 2280 |
| atgcgaggca | gtggcaccca | gctgtttgac | cacattgccg | aatgcctggc | taacttcatg | 2340 |
| gataagctac | aaatcaaaga | caagaagctc | ccactgggtt | ttaccttctc | gttcccctgc | 2400 |
| caccagacta | aactagacga | gagtttcctg | gtctcatgga | ccaagggatt | caagtccagt | 2460 |
| ggagtggaag | gcagagacgt | tgtggctctg | atccggaagg | ccatccagag | gagagggac | 2520 |
| tttgatatcg | acattgtggc | tgtggtgaat | gacacagttg | gaccatgat | gacctgtggt | 2580 |
| tatgatgacc | acaactgtga | gattggtctc | attgtgggca | cgggcagcaa | cgcctgctac | 2640 |
| atggaagaga | tgcgccacat | cgacatggtg | gaaggcgatg | aggggcggat | gtgtatcaat | 2700 |

```
atggagtggg gggccttcgg ggacgatggc tcgctcaacg acattcgcac tgagtttgac    2760
caggagattg acatgggctc actgaacccg ggaaagcaac tgtttgagaa gatgatcagt    2820
gggatgtaca tgggggagct ggtgaggctt atcctggtga agatggccaa ggaggagctg    2880
ctctttgggg ggaagctcag cccagagctt ctcaacaccg gtcgctttga gaccaaagac    2940
atctcagaca ttgaagggga aaggatggc atccggaagg cccgtgaggt cctgatgcgg     3000
ttgggcctgg acccgactca ggaggactgc gtggccactc accggatctg ccagatcgtg    3060
tccacacgct ccgccagcct gtgcgcagcc accctggccg ccgtgctgca gcgcatcaag    3120
gagaacaaag gcgaggagcg gctgcgctct actattgggg tcgacggttc cgtctacaag    3180
aaacaccccc attttgccaa gcgtctacat aagaccgtgc ggcggctggt gcccggctgc    3240
gatgtccgct cctccgctc cgaggatggc agtggcaaag gtgcagccat ggtgacagca    3300
gtggcttacc ggctggccga tcaacaccgt gcccgccaga agacattaga gcatctgcag    3360
ctgagccatg accagctgct ggaggtcaag aggaggatga aggtagaaat ggagcgaggt    3420
ctgagcaagg agactcatgc cagtgccccc gtcaagatgc tgcccaccta cgtgtgtgct    3480
accccggacg gcacagagaa aggggacttc ttggccttgg accttggagg aacaaatttc    3540
cgggtcctgc tggtccgtgt tcggaatggg aagtggggtg gagtggagat gcacaacaag    3600
atctacgcca tcccgcagga ggtcatgcac ggcaccgggg acgagctctt tgaccacatt    3660
gtccagtgca tcgcggactt cctcgagtac atgggcatga agggcgtgtc cctgcctctg    3720
ggttttacct tctccttccc ctgccagcag aacagcctgg acgagagcat cctcctcaag    3780
tggacaaaag gcttcaaggc atctggctgc gagggcgagg acgtggtgac cctgctgaag    3840
gaagcgatcc accggcgaga ggagtttgac ctggatgtgg ttgctgtggt gaacgacaca    3900 gtcgaacta tgatgacctg tggctttgaa gaccctcact gtgaagttgg cctcattgtt    3960
ggcacgggca gcaatgcctg ctacatggag gagatgcgca acgtggaact ggtggaagga    4020 gaagagggc ggatgtgtgt gaacatggaa tgggggggcct tcggggacaa tggatgccta    4080
gatgacttcc gcacagaatt tgatgtggct gtggatgagc tttcactcaa ccccggcaag    4140
cagaggttcg agaaaatgat cagtggaatg tacctgggtg agattgtccg taacattctc    4200
atcgatttca ccaagcgtgg actactcttc cgaggccgca tctcagagcg gctcaagaca    4260 agggcatct ttgaaaccaa gttcttgtct cagattgaga gtgactgcct ggccctgctg    4320
caagtccgag ccatcctgca acacttaggg cttgagagca cctgtgacga cagcatcatt    4380
gttaaggagg tgtgcactgt ggtggcccgg cgggcagccc agctctgtgg cgcaggcatg    4440
gccgctgtgg tggacaggat acgagaaaac cgtgggctgg acgctctcaa agtgacagtg    4500
ggtgtggatg ggacccctca caagctacat cctcactttg ccaaagtcat gcatgagaca    4560
gtgaaggacc tggctccgaa atgtgatgtg tctttcctgc agtcagagga tggcagcggg    4620 aaggggcgg cgctcatcac tgctgtggcc tgccgcatcc gtgaggctgg acagcgatag    4680 aaccccctgaa atcggaaggg acttcctctt tctctccttc ttccctgttt taaattataa    4740
gatgtcatcc ccttgtgtca gagacagacc ccttggcttt tgcttggcag agaggacccc    4800 actgactgg gttttgtctc tgcatctcat tgtagagctt ggtggctgag cttgccctc     4860 ttaagataaa tagagttcca aataaggatt tgttcacatg catcataacc attcccattg    4920
gttctcctaa aacatgaaaa ttatctccct tagtaatccc ccttgccaaa ttccatgtcc    4980
ctgtataatt ctacaggatg gggacactaa tgaagatacg gttgcttcac cttggagcct    5040
gaacatgaca tttctaagtg gggtgcatcc cccagcactg atgttgttac tgattctcct    5100
```

```
gtcagagatc tgggaggtct ccactgagga tgtgagcctg attatcctat aggcagacgt    5160
ggggagggtg gaggggtgac agtggaggaa aatccatgga tatccacgca gcagcccctc    5220
tttaacctca tctacaagca tttgccctgt ggattccagc atttgccatt cctggaatca    5280
aggaatcctg agtctgggca atgaaaccaa agccaggagt tgacgcatcc tgcagttggg    5340
ccagctgtcg catctcagcg gggcgcacat gttatccaca agcaatggac ctttggggaa    5400
ggggagttt ttagtttgtt ttacaaattt ttcctgcaaa agtggaatca ctgtattttc     5460
attttaattt atatttgaaa ttttatttag ttcttgagta gatctgcttc ttcatcttga    5520
catgtaatga atggtcagtt gtacgtaatg tatttatatg ttaatttgtt atgtatatag    5580
atgtgcaagt cttgtcagaa ttggcctcag tgtagttaaa gggcagaagg ggaagatact    5640
gactagtcat agaaatacct cattcgcctg tgggaagaga agggaagcct cttcagggtg    5700
agtgaatggc aaagcggttg cttctggctc ctccttcccc tgtggtcttg gaagtgtgtg    5760
gaaggcaggg acagagatgg aggccgagcc aatagactga agagaccaca gcaattggct    5820
cctccatcta gagattttct tggcagtatt ccatgggatg ttaagcaaag gaaaccaaag    5880
gaatcgtttc aaatggactc atggcttaga aatctttatt cttagggcag tcagtagtat    5940
tctaaagctt tctgacaaga taaaggaagt caccaaaatt tctttttta aattgtatct     6000
aatcctcaac aacaaaccaa aacagaacaa ttaaacagcc aaataaaacc tcagggacaa    6060
cattttggt gtatttgagc cctcccagca agtttcacct tgggtttgta ttttaaatgt     6120
tttacaagaa ttgtccatgt gcttccctag gctgagctgg cattggtctg ctgacctgtt    6180
tttgtgtttt tcttttttt atacacaaca tttatttcaa actattggga gggatgagag     6240
tggcttaaaa acttccatcc ctacttttca agagtgcagt tgattctgaa tctgaaagcc    6300
cgcctctgtc ctaaaataca aacaagcaca gacattaaac ctggatacta tatgataaag    6360
agggatgtaa ctattgaatt ggatacaagg atcagaatgg aaagaaactc acgatgaaat    6420
tgaacctggt ttttgtatat ttatcaaact tgtgctgaga atagtgtctg attatacgac    6480
ttttaagcaa agttgggtgt aattaggtga aaacagccca ggtcctcccg ggagcacaga    6540
ggggctaggg gctggtcctt ctcgtttgct ctagtcttgc tttgctgtct ggtgtagctc    6600
ctctgctgct cccatctgca ctaattgacc caaaacgtgg gtatttcctg ctacacaaaa    6660
gccaaaaggt ttcatgtaga ttttagttca ctaaagggtg cccacaaaat agagattaat    6720
tttaacttaa attttaagct tgaagattag gtactatctg tgaagttaca ctttttttt     6780
ttttttaaa ggtagagatg tgtgtgtgtg taggtattaa agatgtgttg ttggtttcca     6840
aaaaggaaca ctggaaaata aattttgaat gtttatgttc tcagaatcag gttgacagtc    6900
ccttgctgac atggctttgc tttgtgtaaa tacagtggat ctcaatcttc ggggtgtgat    6960
gaatagcgaa tcatctcaaa tccttgagca ctcagtctag tgaagatgtt gtcattatgt    7020
acaatacata actagtttaa ttaactatgt gatgttaact attattaata aattttaaca    7080
ttttccaaaa taaaaaaaaa aaaaaaaa                                       7109
```